(12) United States Patent
Lin et al.

(10) Patent No.: US 12,290,565 B2
(45) Date of Patent: May 6, 2025

(54) METHODS OF USING ANTI-PSGL-1 ANTIBODIES IN COMBINATION WITH JAK INHIBITORS TO TREAT T-CELL MEDIATED INFLAMMATORY DISEASES OR CANCERS

(71) Applicant: AltruBio Inc., Wilmington, DE (US)

(72) Inventors: Shih-Yao Lin, Taipei (TW); Feng-Lin Chiang, Taipei (TW); You-Chia Yeh, Taipei (TW)

(73) Assignee: AltruBio Inc., Wilmington, DE (US)

( * ) Notice: Subject to any disclaimer, the term of this patent is extended or adjusted under 35 U.S.C. 154(b) by 0 days.

(21) Appl. No.: 18/056,166

(22) Filed: Nov. 16, 2022

(65) Prior Publication Data

US 2023/0149544 A1    May 18, 2023

Related U.S. Application Data

(60) Provisional application No. 63/280,463, filed on Nov. 17, 2021.

(51) Int. Cl.
| | | |
|---|---|---|
| A61K 39/395 | (2006.01) | |
| A61K 31/519 | (2006.01) | |
| A61K 39/00 | (2006.01) | |
| A61P 37/06 | (2006.01) | |
| C07K 16/28 | (2006.01) | |

(52) U.S. Cl.
CPC ........ *A61K 39/3955* (2013.01); *A61K 31/519* (2013.01); *A61P 37/06* (2018.01); *C07K 16/2896* (2013.01); *A61K 2039/505* (2013.01); *A61K 2039/545* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 4,683,195 A | 7/1987 | Mullis et al. |
| 4,683,202 A | 7/1987 | Mullis et al. |
| 4,754,065 A | 6/1988 | Levenson et al. |
| 4,800,159 A | 1/1989 | Mullis et al. |
| 4,816,567 A | 3/1989 | Cabilly |
| 5,047,335 A | 9/1991 | Paulson |
| 5,278,299 A | 1/1994 | Wong |
| 5,314,995 A | 5/1994 | Fell, Jr. |
| 5,510,261 A | 4/1996 | Goochee |
| 5,545,806 A | 8/1996 | Lonberg |
| 5,545,807 A | 8/1996 | Surani |
| 5,569,825 A | 10/1996 | Lonberg |
| 5,591,828 A | 1/1997 | Bosslet |
| 5,625,126 A | 4/1997 | Lonberg |
| 5,633,425 A | 5/1997 | Lonberg |
| 5,661,016 A | 8/1997 | Lonberg |
| 5,750,373 A | 5/1998 | Garrard |
| 7,604,800 B2 | 10/2009 | Lin et al. |
| 7,674,605 B2 | 3/2010 | Lin et al. |
| 7,982,017 B2 | 7/2011 | Lin et al. |
| 8,361,472 B2 | 1/2013 | Lin et al. |
| 8,568,718 B2 | 10/2013 | Lin et al. |
| 9,089,614 B2 | 7/2015 | Lin et al. |
| 9,334,329 B2 | 5/2016 | Lin et al. |
| 9,408,923 B2 | 8/2016 | Lin et al. |
| 9,943,610 B2 | 4/2018 | Lin et al. |
| 10,472,422 B2 | 11/2019 | Lin et al. |
| 2008/0171043 A1 | 7/2008 | Lin et al. |
| 2009/0191221 A1 | 7/2009 | Lin et al. |
| 2010/0124551 A1 | 5/2010 | Lin et al. |
| 2011/0165161 A1 | 7/2011 | Lin et al. |
| 2011/0280888 A1 | 11/2011 | Lin et al. |
| 2013/0011391 A1 | 1/2013 | Bassarab et al. |
| 2013/0177579 A1 | 7/2013 | Lin et al. |
| 2013/0209449 A9 | 8/2013 | Bassarab et al. |
| 2014/0105899 A1 | 4/2014 | Lin et al. |
| 2014/0193437 A1 | 7/2014 | Lin et al. |
| 2014/0303180 A1 | 10/2014 | Tyner et al. |
| 2015/0352222 A1 | 12/2015 | Lin et al. |
| 2016/0015830 A1 | 1/2016 | Lin et al. |

(Continued)

FOREIGN PATENT DOCUMENTS

| | | |
|---|---|---|
| EP | 0396387 A2 | 11/1990 |
| EP | 0404097 A2 | 12/1990 |

(Continued)

OTHER PUBLICATIONS

Abedin et al (Ruxolitinib: a potential treatment for corticosteroid refractory acute graft-versus-host disease, Expert Opinion on Investigational Drugs, vol. 29, pp. 423-427, Published: Apr. 19, 2020). (Year: 2020).*

Abedin, S. et al. (2020). "EP1406—Neihulizumab (ABGN-168H) in Patients with Steroid Refractory Acute Graft-Versus-Hose-Disease (SR-AGVHD): Preliminary Results of A Phase I Study," Abstract Book—25th Congress of the European Hematology Association, pp. 657-658, 2 pages.

Al-Lazikani, B. et al. (Nov. 7, 1997). "Standard Conformations for the Canonical Structures of Immunoglobulins," Journal of Molecular Biology 273(4):927-948.

Azab, A.K. et al. (Feb. 9, 2012). "P-Selectin Glycoprotein Ligand Regulates the Interaction of Multiple Myeloma Cells with the Bone Marrow Microenvironment," Blood 119(6):1468-1478.

(Continued)

*Primary Examiner* — Peter J Reddig
*Assistant Examiner* — Sarah A Alsomairy
(74) *Attorney, Agent, or Firm* — Morrison & Foerster LLP

(57) ABSTRACT

Provided herein are methods of treating or preventing a T-cell mediated inflammatory disease or cancer in a subject in need thereof comprising administering to the subject a therapeutically effective amount of an antibody that specifically binds to human PSGL-1 in combination with a Janus kinase (JAK) inhibitor. In some embodiments, the T-cell mediated inflammatory disease is GVHD, e.g., acute GVHD or chronic GVHD.

23 Claims, 12 Drawing Sheets

Specification includes a Sequence Listing.

(56) References Cited

U.S. PATENT DOCUMENTS

| | | |
|---|---|---|
| 2016/0015831 A1 | 1/2016 | Lin et al. |
| 2016/0139131 A1 | 5/2016 | Lin et al. |
| 2017/0198052 A1 | 7/2017 | Lin et al. |
| 2018/0238895 A1 | 8/2018 | Lin et al. |
| 2018/0264131 A1 | 9/2018 | Lin et al. |
| 2020/0277395 A1 | 9/2020 | Lin et al. |
| 2021/0113710 A1 | 4/2021 | Lin et al. |
| 2022/0112302 A1 | 4/2022 | Lin et al. |

FOREIGN PATENT DOCUMENTS

| | | | |
|---|---|---|---|
| WO | 198704462 A1 | 7/1987 | |
| WO | 198912624 A2 | 12/1989 | |
| WO | 198912624 A3 | 4/1990 | |
| WO | 199114438 A1 | 10/1991 | |
| WO | 199208495 A1 | 5/1992 | |
| WO | 199311161 A1 | 6/1993 | |
| WO | 199958572 A1 | 11/1999 | |
| WO | 2005110475 A2 | 11/2005 | |
| WO | 2005110475 A3 | 2/2006 | |
| WO | 2007070514 A1 | 6/2007 | |
| WO | 2007146172 A2 | 12/2007 | |
| WO | 2007146172 A3 | 5/2008 | |
| WO | 2008157208 A2 | 12/2008 | |
| WO | 2008157208 A3 | 2/2009 | |
| WO | 2007146172 A8 | 4/2009 | |
| WO | 2009079649 A1 | 6/2009 | |
| WO | 2011079283 A1 | 6/2011 | |
| WO | WO-2012174001 A1 * | 12/2012 | ........... A61K 39/395 |
| WO | 2013103800 A1 | 7/2013 | |
| WO | 2014100762 A1 | 6/2014 | |
| WO | 2015196089 A1 | 12/2015 | |
| WO | 2015196167 A1 | 12/2015 | |
| WO | 2017120534 A1 | 7/2017 | |
| WO | WO-2019171326 A1 * | 9/2019 | ......... A61K 31/4439 |

OTHER PUBLICATIONS

Belmonte, B. et al. (Jun. 12, 2021). "Constitutive PSGL-1 Correlates with CD30 and TCR Pathways and Represents a Potential Target for Immunotherapy in Anaplastic Large T-Cell Lymphoma," Cancers 13(12):2958-2973.

Bijnsdorp, I.V. et al. (2011). "Analysis of Drug Interactions," Methods Mol. Biol. 731:421-434.

Boerner, P. et al. (Jul. 1, 1991). "Production of a Antigen-Specific Human Monoclonal Antibodies from In Vitro-Primed Human Splenocytes," J. Immunol. 147(1):86-95.

Boyd, P.N. et al. (Dec. 1995). "The Effect of the Removal of Sialic Acid, Galactose and Total Carbohydrate on the Functional Activity of Campath-1H," Mol. Immunol. 32(17/18):1311-1318.

Cabilly, S. et al. (1984). "Generation of Antibody Activity from Immunoglobulin Polypeptide Chains Produced in *Escherichia coli*," Proc. Nat'l. Acad. Sci. USA 81(11):3273-3277.

Chen, S.-C. et al. (Nov. 15, 2004, e-pub. Jun. 15, 2004). "Cross-Linking of P-Selectin Glycoprotein Ligand-1 Induces Death of Activated T Cells," Blood 104(10):3233-3242.

Chothia, C. et al. (Aug. 20, 1987). "Canonical Structures for the Hypervariable Regions of Immunoglobulins," J. Mol. Biol. 196(4):901-917.

Chou, T.-C. (Jan. 15, 2010, e-pub. Jan. 12, 2010). "Drug Combination Studies and Their Synergy Quantification Using the Chou-Talalay Method," Cancer Res. 70(2):440-446.

Chu, G. et al. (1987). "Electroporation for the Efficient Transfection of Mammalian Cells with DNA," Nucleic Acid Res. 15(3):1311-1325.

clinicaltrials.gov (Aug. 26, 2016). "NCT02881138—A Study of RC48-ADC in Subjects with HER2-Positive Advanced Malignant Solid Tumors," 7 pages.

clinicaltrials.gov (Feb. 14, 2017). "NCT03052634—A Study of RC48-ADC in Subjects with Advance Breast Cancer," 8 pages.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Damsky, W. et al. (Mar. 2021, e-pub. Oct. 28, 2020). "The Emerging Role of Janus Kinase Inhibitors in the Treatment of Autoimmune and Inflammatory Diseases," Journal of Allergy and Clinical Immunology 147(3):814-826.

Edelman, G.M. et al. (1969). "The Covalent Structure of an Entire γG Immunoglobulin Molecule," Proc. Natl. Acad. Sci. USA 63:78-85.

GenBank Accession No. (Jun. 10, 2016). "AAA74577.1—P-selectin glycoprotein ligand [*Homo sapiens*]," 1 page.

GenBankTM Accession No. (Mar. 12, 2015). "XP_005269133—Predicted: P-selectin glycoprotein ligand 1 isoform X1 [*Homo sapiens*]," 2 pages.

Hollinger, P. et al. (Jul. 1993). "Diabodies": Small Bivalent And Bispecific Antibody Fragments, Proc. Natl. Acad. Sci. USA 90:6444-6448.

Holt, L.J. et al. (Nov. 2003). "Domain Antibodies: Proteins For Therapy," Trends in Biotechnology 21(11): 484-490.

Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.

Hosseini, A. et al. (2020). "Janus Kinase Inhibitors: A Therapeutic Strategy for Cancer and Autoimmune Diseases," J. Cell Physiol. 235(9):5903-5924.

Hsu, T.-A. et al. (Apr. 4, 1997). "Differential N-Glycan Patterns of Secreted and Intracellular IgG Produced in Trichoplusia ni Cells," J. Biol. Chem. 272(14): 9062-9070.

Huang, C.-C. et al. (2005). "A novel Apoptosis-Inducing Anti-PSGL-1 Antibody for T Cell-Mediated Diseases," Eur. J. Immunol. 35(7):2239-2249.

Iliades, P. et al. (1997). "Triabodies: Single Chain Fv Fragments Without a Linker Form Trivalent Trimers," FEBS Letters 409:437-441.

International Search Report, and Written Opinion, mailed on Feb. 28, 2023, for PCT Application No. PCT/US2022/079976, filed Nov. 16, 2022, 19 pages.

Jagasia, M. et al. (May 14, 2020, e-pub. Mar. 5, 2020). "Ruxolitinib for the Treatment of Steroid-Refractory Acute GVHD (REACH1): A Multicenter, Open-Label Phase 2 Trial," Blood 135(20):1739-1749.

Jefferis, R. et al. (1997). "Glycosylation Of Antibody Molecules: Structural and Functional Significance," Chem. Immunol. 65:111-128.

Karagianni, F. et al. (Mar. 11, 2021). "Ruxolitinib with Resminostat Exert Synergistic Antitumor Effects in Cutaneous T-Cell Lymphoma," PLoS ONE 16(3):e0248298, 14 pages.

Kortt, A.A. et al. (Apr. 1997). "Single-Chain Fv Fragments of Anti-Neuraminidase Antibody NC10 Containing Five-and Ten-Residue Linkers Form Dimers and with Zero-Residue Linker a Trimer," Protein Engineering 10(4):423-433.

Köhler, G. et al. (Aug. 7, 1975). "Continuous Cultures of Fused Cells Secreting Antibody of Predefined Specificity," Nature 256:495-497.

Levine, J.E. et al. (2010). "Graft-Versus-Host Disease Treatment: Predictors of Survival," BBMT 16(12):1693-1699.

Marks, J.D. et al. (1991). "By-Passing Immunization. Human Antibodies From V-Gene Libraries Displayed on Phage," J. Mol. Biol. 222:581-597.

McCafferty, J. et al. (Dec. 6, 1990). "Phage Antibodies: Filamentous Phage Displaying Antibody Variable Domains," Nature 348:552-554.

Mothy, M. et al. (Oct. 22, 2020). "Refractory acute Graft-Versus-Host Disease: A New Working Definition Beyond Corticosteroid Refractoriness," Blood 136(17):1903-1906.

Mullis, K.B. et al. (1994). PCR: The Polymerase Chain Reaction, Mullis et al. eds., Birkauswer Press, Boston, 5 pages.

Muyldermans, S. (Jun. 2001). "Single Domain Camel Antibodies: Current Status," Reviews in Molecular Biotechnology 74(4):277-302.

(56) References Cited

OTHER PUBLICATIONS

NCBI RefSeq Gene ID No. (Apr. 4, 2018). "SELPLG Selectin P Ligand [ *Homo sapiens* (human)]," Gene ID: 6404, 6 pages.
Nisonoff, A. et al. (Aug. 1960). "Separation of Univalent Fragments from the Bivalent Rabbit Antibody Molecule by Reduction of Disulfide Bonds," Arch Biochem. Biophys. 89(2):230-244.
O'Shea, J.J. et al. (Jan. 10, 2013). "JAKs and STATs in Immunity, Immunodeficiency, and Cancer," N. Engl. J. Med. 368(2):161-170, 17 pages.
Oi, V.T. et al. (Feb. 1983). "Immunoglobulin Gene Expression in Transformed Lymphoid Cells," Proc. Natl. Acad. Sci. USA 80:825-829.
Okiyama, N. et al. (2014, e-pub. Dec. 12, 2013). "Reversal of CD8 T-cell-Mediated Mucocutaneous Graft-Versus-Host-Like Disease by the JAK inhibitor Tofacitinib," Journal of Investigative Dermatology 134:992-1000.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Porter, R.R. (1959). "The Hydrolysis of Rabbit γ-Globulin and Antibodies with Crystalline Papain," Biochem. J. 73: 119-127.
Presta, L.G. et al. (2002). "Engineering Therapeutic Antibodies for Improved Function," Biochemical Society Transactions 30(4):487-490.
Przepiorka, D. et al. (2020, e-pub. Oct. 22, 2019). "FDS Approval Summary: Ruxolitinib for Treatment of Steroid-Refractory Acute Graft-Versus-Host Disease," The Oncologist 25:e328-e334.
Qureshy, Z. et al. (2020). "Targeting the JAK/STAT Pathway in Solid Tumours," J. Cancer Metastasis Treat. 6:27-44, 26 pages.
Rice, D. et al. (Dec. 1982). "Regulated Expression of an Immunoglobulin κ Gene Introduced Into a Mouse Lymphoid Cell Line," Proc. Natl. Acad. Sci. USA 79:7862-7865.
Rousseaux. J. et al. (1986). "Optimal Conditions for the Preparation of Proteolytic Fragments from Monoclonal IgG of Different Rat IgG Subclasses," Methods Enzymol. 121:663-669.
Sambrook, J. et al. (1989). Molecular Cloning: A Laboratory Manual, 3rd Ed., 29 pages.
Sheets, M.D. et al. (May 26, 1998). "Efficient Construction of a Large Nonimmune Phage Antibody Library: The Production of High-Affinity Human Single-Chain Antibodies to Protein Antigens," Proc. Nat'l. Acad. Sci. USA 95 (11):6157-6162.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

Smyth, D.G. (1967). "Use of Papain, Pepsin, and Subtilisin in Sequence Determination," Methods in Enzymology 11:421-426.
Thomas, S.J. et al. (2015, e-pub. Jul. 7, 2015). "The Role of JAK/STAT Signalling in the Pathogenesis, Prognosis and Treatment of Solid Tumours," Br. J. Cancer 113:365-371.
Toneguzzo, F. et al. (Feb. 1986). "Electric Field-Mediated DNA Transfer: Transient and Stable Gene Expression in Human and Mouse Lymphoid Cells," Mol. Cell. Biol. 6(2):703-706.
Tripodo, C. et al. (2009)."P-Selectin Glycoprotein Ligand-1 as a Potential Target for Humoral Immunotherapy of Multiple Myeloma," Curr Cancer Drug Targets 9(5):617-625.
U.S. Appl. No. 18/183,066, filed Mar. 13, 2023, Lin et al. (Copy not submitted herewith pursuant to the waiver of 37 C.F.R. 1.98(a)(2)(iii) issued by the Office on Sep. 21, 2004).
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
Vainchenker, W. et al. (May 23, 2013, e-pub. Aug. 6, 2012). "JAK/STAT Signaling in Hematological Malignancies," Oncogene 32(21):2601-2613.
Vaughan, T.J. et al. (Mar. 1996). "Human Antibodies with Sub-Nanomolar Affinities Isolated from a Large Non-Immunized Phage Display Library," Nature Biotechnology 14(3):309-314.
Verstovsek, S. et al. (Mar. 1, 2012). "A Double-Blind, Placebo-Controlled Trial of Ruxolitinib for Myelofibrosis," The New England Journal of Medicine 366(9):799-807.
Villarino, A.V. et al. (Apr. 2017, e-pub. Mar. 22, 2017). "Mechanisms and Consequences of JAK-STAT Signaling in the Immune System," Nat Immunol. 18(4):374-384.
Waldmann, T.A. et al. (2017, e-pub. Feb. 9, 2017). "Disorders of the JAK/STAT Pathway in T Cell Lymphoma Pathogenesis: Implications for Immunotherapy," Annu. Rev. Immunol 35:533-550.
Wittwer, A.J. et al. (May 1, 1990). "Glycosylation at Asn-184 Inhibits the Conversion of Single-Chain to Two-Chain Tissue-Type Plasminogen Activator by Plasmin," Biochemistry 29(17):4175-4180.
Wright, A. et al. (Jan. 1997). "Effect of Glycosylation on Antibody Function: Implications for Genetic Engineering," Trends Biotech. 15:26-32.
Wyss, D.F. et al. (1996). "The Structural Role of Sugars in Glycoproteins," Current Opin. Biotech. 7:409-416.
Zeiser, R. et al. (May 7, 2020). "Ruxolitinib for Glucocoticoid-Refractory Acute Graft-versus-Host Disease," The New England Journal of Medicine 382(19):1800-1810.
International Preliminary Report on Patentability, issued May 2, 2024, for PCT Application No. PCT/US2022/079976, filed Nov. 16, 2022, 11 pages.

\* cited by examiner

Fixed ratio of 3.3:1
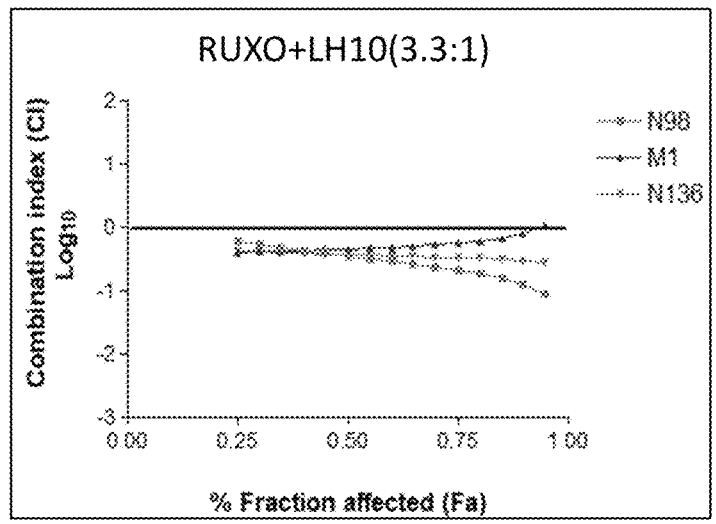
Fixed ratio of 1.1:1
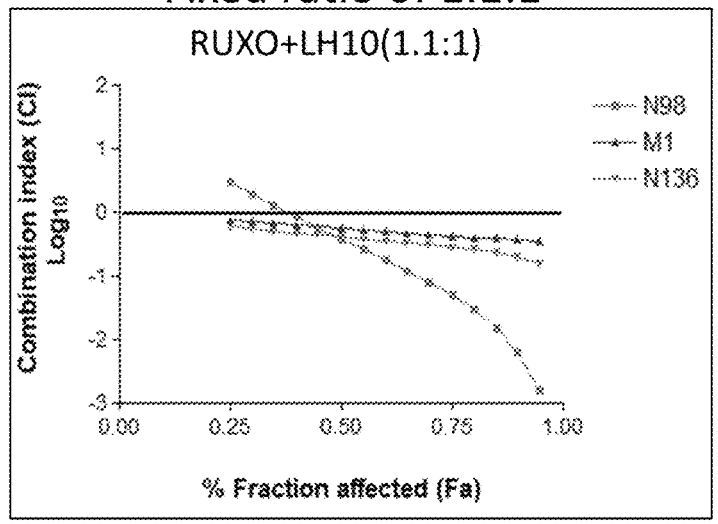
FIG. 4A
Fixed ratio of 0.37:1
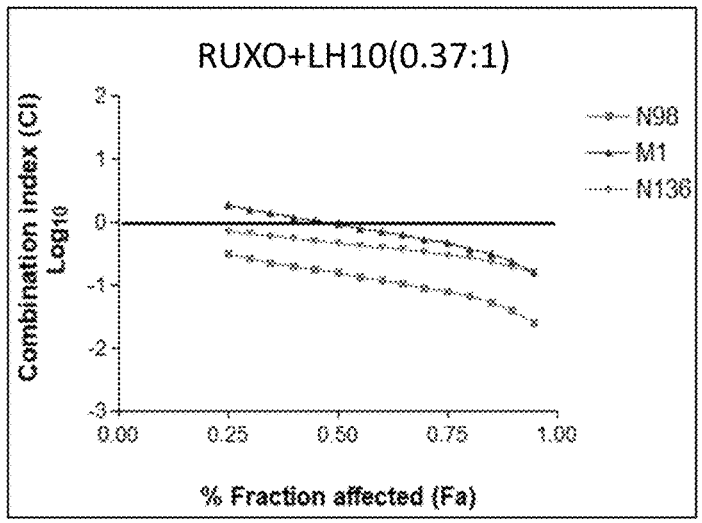

Fixed ratio of 3.3:1
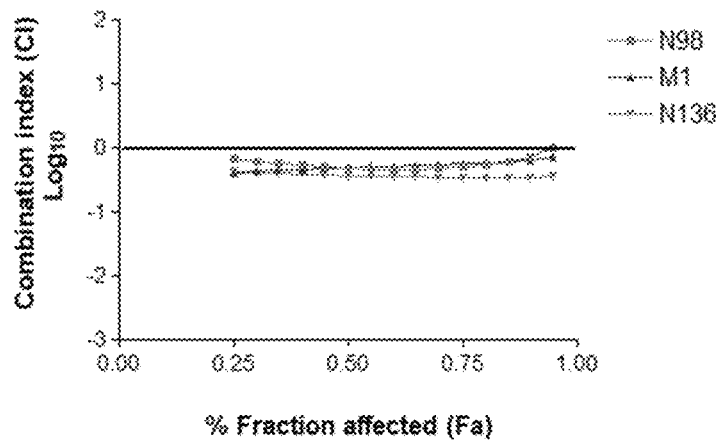
Fixed ratio of 1.1:1
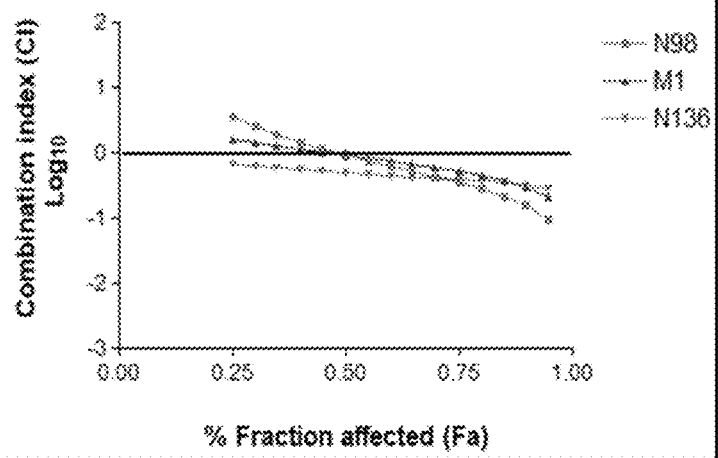
FIG. 4B
Fixed ratio of 0.37:1
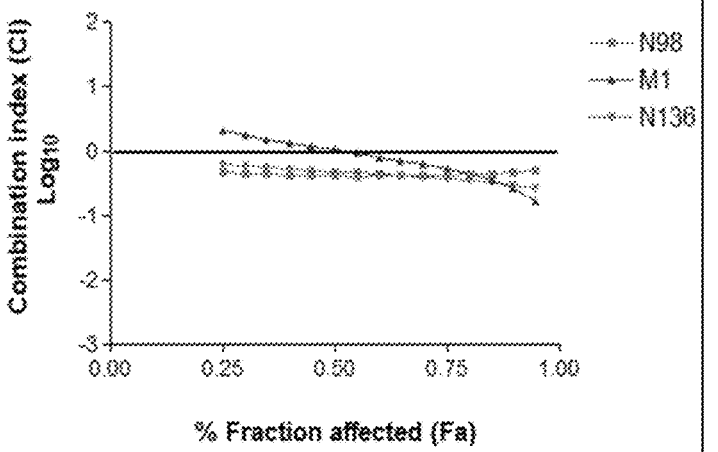

Fixed ratio of 3.3:1
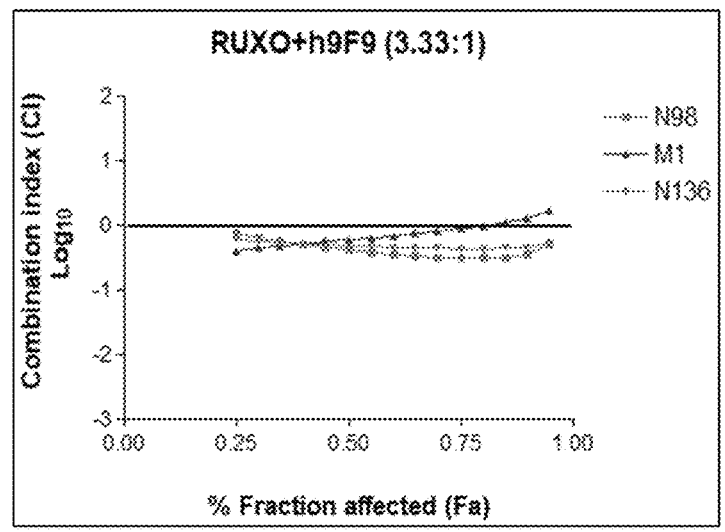
Fixed ratio of 1.1:1
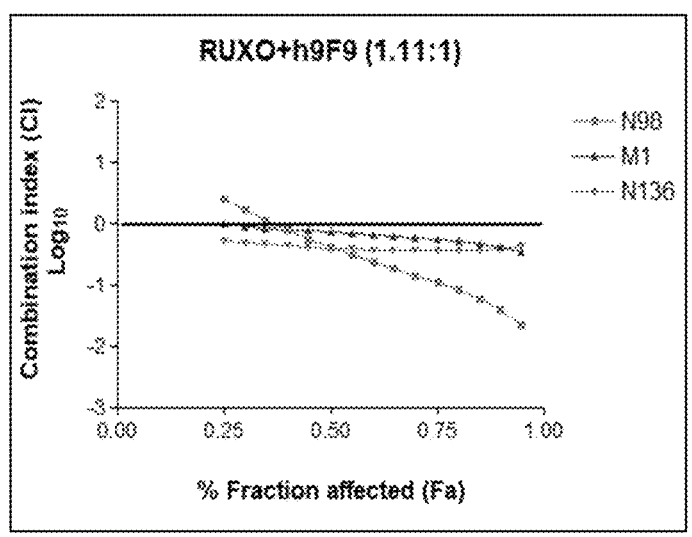
FIG. 4C
Fixed ratio of 0.37:1
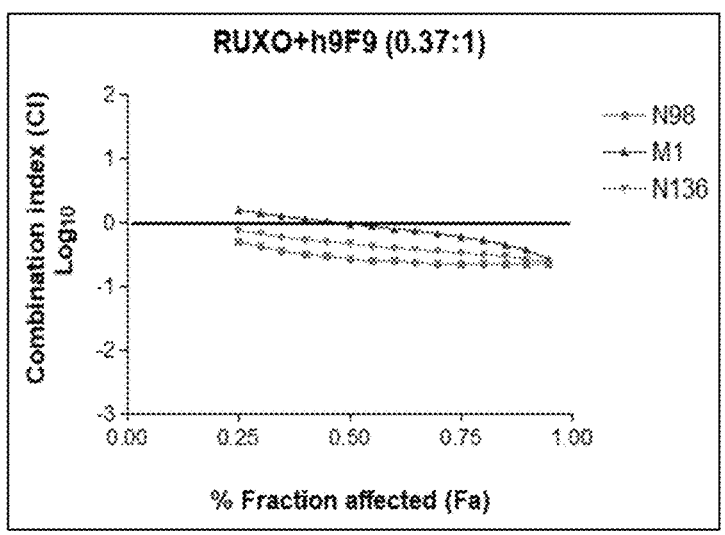

METHODS OF USING ANTI-PSGL-1 ANTIBODIES IN COMBINATION WITH JAK INHIBITORS TO TREAT T-CELL MEDIATED INFLAMMATORY DISEASES OR CANCERS

CROSS-REFERENCE TO RELATED APPLICATIONS

This application claims the benefit of U.S. Provisional Application No. 63/280,463, filed Nov. 17, 2021, which is hereby incorporated by reference in its entirety.

REFERENCE TO AN ELECTRONIC SEQUENCE LISTING

The contents of the electronic sequence listing (606592001600seqlist.xml; Size: 38,629 bytes; and Date of Creation: Nov. 15, 2022) are incorporated herein by reference in their entirety.

FIELD

Provided herein are methods of treating or preventing a T-cell mediated inflammatory disease or cancer in a subject in need thereof comprising administering to the subject a therapeutically effective amount of an antibody that specifically binds to human PSGL-1 in combination with a Janus kinase (JAK) inhibitor.

BACKGROUND

T-cell mediated inflammatory diseases, such as graft-versus-host diseases (GVHD), skin disorders, multiple sclerosis, rheumatoid arthritis, juvenile arthritis, type I diabetes, lupus, inflammatory bowel disease, Crohn's disease, myasthenia gravis, immunoglobulin nephropathies, myocarditis, and autoimmune thyroid disorders, as well as cancers such as leukemias and lymphomas represent serious health conditions. As one example, acute GvHD (aGvHD) is a major complication of hematopoietic cell transplantation (HCT) that accounts for most non-relapse mortality. Standard first-line treatment for aGvHD consists of steroids at a dose of 1-2 mg/kg of prednisone or equivalent, with complete response (CR) rates ranging from 25-41%. Patients who (a) progressed after 3 days of treatment with methylprednisolone (MP) 2 mg/kg/day equivalent, (b) did not improve after 7 days of treatment with MP 2 mg/kg/day equivalent, (c) progressed to a new organ after treatment with MP 1 mg/kg/day equivalent for skin and upper gastro-intestinal GVHD, or (d) recurred during or after a steroid taper are considered steroid-refractory (Przepiorka et al., (2019) The oncologist, 24:1-7).

The Janus kinase/signal transducer and activator of transcription (JAK/STAT) signaling pathway is known to be associated with the development and progression of many hematological and solid cancers [Waldmann and Chen (2017) Annu Rev Immunol 35:533-550; Vainchenker and Constantinescu (2013) Oncogene 32(21):2601-2613; Thomas et al., (2015) Br J Cancer, 113:365-71; O'Shea et al., (2013) N Engl J Med 368:161-70], and also be integral to the effects of inflammatory cytokines on the immune system (Villarino et al., (2017) Nat Immunol, 18:374-384). STATs and their upstream activators, JAKs, are being extensively explored as targets for cancer and inflammatory disease therapy (Qureshy et al., (2020) J Cancer Metastasis Treat 6:27-44; Hosseini et al., (2020) J Cell Physiol. 235 (9):5903-5924). Many JAK inhibitors have been or are actively being tested in clinical trials as monotherapy or in combination with other agents in patients with inflammatory diseases or cancers; at least five of these inhibitors are already Food and Drug Administration (FDA) approved for the treatment of inflammatory diseases or cancers including rheumatoid arthritis, ulcerative colitis, GvHD (Qureshy et al., (2020) J Cancer Metastasis Treat 6:27-44; Damsky et al., (2021) Journal of Allergy and Clinical Immunology 147(3): 814-826) and myelofibrosis.

Ruxolitinib is a JAK 1/2 inhibitor and is recently approved for the treatment of steroid-refractory acute GVHD (sr-aGvHD) and chronic GVHD (cGVHD). Despite the approval of ruxolitinib, together with several types of secondary therapies, the long-term outcome of sr-aGvHD is very poor with the mortality rate ranging between 70-80% (Levine et al., (2010) BBMT, 16(12): 1693-1699). The outcome of subjects who failed second line therapy (treatment-refractory) is even more dismal.

Acute GvHD is caused by donor-derived alloreactive T cells that recognize and destroy patient tissue including the skin, GI track and liver. Targeting and controlling or eliminating highly proliferative and highly activated alloreactive T cells is a fundamental strategy to treat GvHD.

PSGL-1, long known to be an adhesion molecules involved in leukocyte trafficking, has been recognized as an immune checkpoint regulator that down-regulates chronic proliferated/activated T-cells (Chen et al., (2004) Blood, 104(10): 3233-3242; Huang et al., (2005) Eur J Immunol, 35(7): 2239-2249). Neihulizumab (AbGn-168H), a humanized IgG4κ monoclonal antibody (mAb) directed against PSGL-1, preferentially induces apoptosis (programmed cell death) of late stage activated T cells upon binding to PSG1-1. Neihulizumab has been tested in GVHD with encouraging clinical outcomes.

Several studies identified that PSGL-1 can be a potential target for immunotherapy treatment of several hematological malignancies. For example, gene expression profiling revealed that PSGL-1 is strongly expressed by the cells of multiple myeloma and anaplastic large T-cell lymphoma, and further evaluation of the effects elicited by in vitro treatment also indicated a promising candidate for humoral immunotherapy in these malignancies (Tripodo et al., (2009) Curr Cancer Drug Targets, 9(5):617-625; Azab et al., (2012) Blood, 119(6):1468-1478; Belmonte et al., (2021) Cancers, 13(12):2958-2973).

There remains a need for more effective treatments for T-cell mediated inflammatory diseases and cancers.

All publications, patents, and patent applications cited herein are hereby incorporated by reference in their entirety for all purposes.

BRIEF SUMMARY

To meet this need, provided herein are methods for using anti-PSGL-1 antibodies in combination with JAK inhibitors to treat or prevent T-cell mediated inflammatory diseases or cancers. These methods are based at least in part on the demonstration herein that anti-PSGL-1 antibodies were found to act synergistically in combination with JAK inhibitors to promote induction of apoptosis in activated T cells and improve outcomes in patients with GVHD.

Accordingly, in one aspect, provided herein is a method of treating or preventing a T-cell mediated inflammatory disease, the method comprising administering to a subject in need thereof a therapeutically effective amount of an antibody that specifically binds to human PSGL-1 in combination with a Janus kinase (JAK) inhibitor. In another aspect, provided herein is a method of treating or preventing a cancer (e.g., a T-cell mediated cancer such as T-cell leukemia or T-cell lymphoma), the method comprising administering to a subject in need thereof a therapeutically effective amount of an antibody that specifically binds to human PSGL-1 in combination with a Janus kinase (JAK) inhibitor. In some embodiments, the antibody that specifically binds to human PSGL-1 comprises a heavy chain comprising a heavy chain variable (VH) domain and a light chain comprising a light chain variable (VL) domain. In some embodiments, the VH domain comprises a CDR-H1 comprising the amino acid sequence SFGMH (SEQ ID NO:8), a CDR-H2 comprising the amino acid sequence YINGGSSTIFYANAVKG (SEQ ID NO:9), and a CDR-H3 comprising the amino acid sequence YASYGGGAMDY (SEQ ID NO:10); and the VL domain comprises a CDR-L1 comprising the amino acid sequence RSSQSIVHNDGNTYFE (SEQ ID NO:5), a CDR-L2 comprising the amino acid sequence KVSNRFS (SEQ ID NO:6), and a CDR-L3 comprising the amino acid sequence FQGSYVPLT (SEQ ID NO:7). In some embodiments, the VH domain comprises a CDR-H1 comprising the amino acid sequence AYYIH (SEQ ID NO:24), a CDR-H2 comprising the amino acid sequence RVNPNTGGTSYN-PKFKG (SEQ ID NO:25), and a CDR-H3 comprising the amino acid sequence SGSPYYRYDD (SEQ ID NO:26); and the VL domain comprises a CDR-L1 comprising the amino acid sequence RASSTVNSTYLH (SEQ ID NO:28), a CDR-L2 comprising the amino acid sequence GSSNLAS (SEQ ID NO:29), and a CDR-L3 comprising the amino acid sequence QQYSGYPLT (SEQ ID NO:30). In some embodiments, the VH domain comprises a CDR-H1 comprising the amino acid sequence TNAMN (SEQ ID NO:32), a CDR-H2 comprising the amino acid sequence RIRSKSNNYATYY-ADSVKD (SEQ ID NO:33), and a CDR-H3 comprising the amino acid sequence GGSYWYFDV (SEQ ID NO:34); and the VL domain comprises a CDR-L1 comprising the amino acid sequence RSSQSIVNSNGNTYLE (SEQ ID NO:36), a CDR-L2 comprising the amino acid sequence KVSNRFS (SEQ ID NO:37), and a CDR-L3 comprising the amino acid sequence FQGSHVPWT (SEQ ID NO:38).

In some embodiments, the JAK inhibitor inhibits JAK1 and/or JAK2. In some embodiments, the JAK inhibitor inhibits JAK1 and/or JAK3. In some embodiments, the JAK inhibitor is ruxolitinib or tofacitinib. In some embodiments, the antibody is a humanized antibody. In some embodiments, the VH domain comprises the amino acid sequence EVQLVESGGGLVQPGGSLRLS-CAASGFTFSSFGMHWVRQAPGKGLEWVAYINGGSS-TIFYA NAVKGRFTISRDNAKNTLYLQMNSLRAEDTA-VYYCARYASYGGGAMDYWGQGTLVTVSS (SEQ ID NO:4). In some embodiments, the VL domain comprises the amino acid sequence DIQMTQSPSSLSASVGDRVTIT-CRSSQSIVHNDGNTYFEWYQQKPGKAPKLLIYKVS-NRFS GVPSRFSGSGSGTHETLTISSLQPEDFATYYCF-QGSYVPLTEGQGTKVEIK (SEQ ID NO:3). In some embodiments, the heavy chain further comprises an antibody constant domain. In some embodiments, the constant domain is a human IgG4 constant domain. In some embodiments, the constant domain is a human IgG4 constant domain comprising an S228P amino acid substitution at position 228, wherein the numbering is according to EU numbering. In some embodiments, the light chain is a human kappa or lambda light chain. In some embodiments, the heavy chain comprises the amino acid sequence of SEQ ID NO:2. In some embodiments, the VH domain comprises a VH domain sequence of the amino acid sequence of SEQ ID NO:27 and/or the VL domain comprises a VL domain sequence of the amino acid sequence of SEQ ID NO:31. In some embodiments, the heavy chain comprises the amino acid sequence of SEQ ID NO:27 and/or the light chain comprises the amino acid sequence of SEQ ID NO:31. In some embodiments, the VH domain comprises a VH domain sequence of the amino acid sequence of SEQ ID NO:35 and/or the VL domain comprises a VL domain sequence of the amino acid sequence of SEQ ID NO:39. In some embodiments, the heavy chain comprises the amino acid sequence of SEQ ID NO:35 and/or the light chain comprises the amino acid sequence of SEQ ID NO:39. In some embodiments, the antibody that specifically binds to human PSGL-1 comprises the amino acid sequence of SEQ ID NO:23. In some embodiments, the light chain comprises the amino acid sequence of SEQ ID NO:1.

In some embodiments, the T-cell mediated inflammatory disease is graft-versus-host disease (GVHD). In some embodiments, the T-cell mediated inflammatory disease is acute GVHD or chronic GVHD. In some embodiments, the T-cell mediated inflammatory disease is steroid-refractory acute GVHD (SR-aGVHD) or treatment-refractory acute GVHD (TR-aGVHD). In some embodiments, the T-cell mediated inflammatory disease is selected from the group consisting of: a skin disorder, multiple sclerosis, rheumatoid arthritis, juvenile arthritis, type I diabetes, lupus, inflammatory bowel disease, Crohn's disease, myasthenia gravis, immunoglobulin nephropathies, myocarditis, and autoimmune thyroid disorder. In some embodiments, the cancer is a T-cell mediated cancer. In some embodiments, the cancer is a T-cell leukemia or T-cell lymphoma. In some embodiments, human PSGL-1 comprises the amino acid sequence of SEQ ID NO:11 or SEQ ID NO:22. In some embodiments, the subject is a human. In some embodiments, the antibody is administered by intravenous infusion. In some embodiments, the JAK inhibitor is administered orally. In some embodiments, the antibody is a monoclonal antibody. In some embodiments, the JAK inhibitor is administered to the subject before, after, or simultaneous with administration of the antibody. In some embodiments, prior to administration of the antibody and the JAK inhibitor, the subject has been treated with a corticosteroid. In some embodiments, administration of the antibody and the JAK inhibitor results in a reduction in one or more symptoms of the T-cell mediated inflammatory disease in the subject.

In another aspect, provided herein is an antibody that specifically binds to human PSGL-1 for use in a method of treating or preventing a T-cell mediated inflammatory disease or cancer in a subject, e.g., according to any one of the above embodiments. In some embodiments, the method comprises administering to the subject a therapeutically effective amount of the antibody in combination with a Janus kinase (JAK) inhibitor. In some embodiments, the antibody comprises a heavy chain comprising a heavy chain variable (VH) domain and a light chain comprising a light chain variable (VL) domain; wherein the VH domain comprises a CDR-H1 comprising the amino acid sequence SFGMH (SEQ ID NO:8), a CDR-H2 comprising the amino acid sequence YINGGSSTIFYANAVKG (SEQ ID NO:9), and a CDR-H3 comprising the amino acid sequence YASYGG-GAMDY (SEQ ID NO:10); and wherein the VL domain comprises a CDR-L1 comprising the amino acid sequence RSSQSIVHNDGNTYFE (SEQ ID NO:5), a CDR-L2 comprising the amino acid sequence KVSNRFS (SEQ ID NO:6), and a CDR-L3 comprising the amino acid sequence FQGSYVPLT (SEQ ID NO:7). In some embodiments, the antibody comprises a heavy chain comprising a heavy chain variable (VH) domain and a light chain comprising a light chain variable (VL) domain; wherein VH domain comprises a CDR-H1 comprising the amino acid sequence AYYIH (SEQ ID NO:24), a CDR-H2 comprising the amino acid sequence RVNPNTGGTSYNPKFKG (SEQ ID NO:25), and a CDR-H3 comprising the amino acid sequence SGSPYYRYDD (SEQ ID NO:26); and the VL domain comprises a CDR-L1 comprising the amino acid sequence RASSTVNSTYLH (SEQ ID NO:28), a CDR-L2 comprising the amino acid sequence GSSNLAS (SEQ ID NO:29), and a CDR-L3 comprising the amino acid sequence QQYSGYPLT (SEQ ID NO:30). In some embodiments, the antibody comprises a heavy chain comprising a heavy chain variable (VH) domain and a light chain comprising a light chain variable (VL) domain; wherein the VH domain comprises a CDR-H1 comprising the amino acid sequence TNAMN (SEQ ID NO:32), a CDR-H2 comprising the amino acid sequence RIRSKSNNYATYYADSVKD (SEQ ID NO:33), and a CDR-H3 comprising the amino acid sequence GGSYWYFDV (SEQ ID NO:34); and the VL domain comprises a CDR-L1 comprising the amino acid sequence RSSQSIVNSNGNTYLE (SEQ ID NO:36), a CDR-L2 comprising the amino acid sequence KVSNRFS (SEQ ID NO:37), and a CDR-L3 comprising the amino acid sequence FQGSHVPWT (SEQ ID NO:38).

In another aspect, provided herein is the use of an antibody that specifically binds to human PSGL-1 in the manufacture of a medicament for treating or preventing a T-cell mediated inflammatory disease or cancer; wherein the antibody is to be administered in combination with a Janus kinase (JAK) inhibitor. In another aspect, provided herein is the use of an antibody that specifically binds to human PSGL-1 and a Janus kinase (JAK) inhibitor in the manufacture of a medicament for treating or preventing a T-cell mediated inflammatory disease or cancer. In some embodiments, the antibody comprises a heavy chain comprising a heavy chain variable (VH) domain and a light chain comprising a light chain variable (VL) domain; wherein the VH domain comprises a CDR-H1 comprising the amino acid sequence SFGMH (SEQ ID NO:8), a CDR-H2 comprising the amino acid sequence YINGGSSTIFYANAVKG (SEQ ID NO:9), and a CDR-H3 comprising the amino acid sequence YASYGGGAMDY (SEQ ID NO:10); and wherein the VL domain comprises a CDR-L1 comprising the amino acid sequence RSSQSIVHNDGNTYFE (SEQ ID NO:5), a CDR-L2 comprising the amino acid sequence KVSNRFS (SEQ ID NO:6), and a CDR-L3 comprising the amino acid sequence FQGSHVPWT (SEQ ID NO:7). In some embodiments, the antibody comprises a heavy chain comprising a heavy chain variable (VH) domain and a light chain comprising a light chain variable (VL) domain; wherein VH domain comprises a CDR-H1 comprising the amino acid sequence AYYIH (SEQ ID NO:24), a CDR-H2 comprising the amino acid sequence RVNPNTGGTSYNPKFKG (SEQ ID NO:25), and a CDR-H3 comprising the amino acid sequence SGSPYYRYDD (SEQ ID NO:26); and the VL domain comprises a CDR-L1 comprising the amino acid sequence RASSTVNSTYLH (SEQ ID NO:28), a CDR-L2 comprising the amino acid sequence GSSNLAS (SEQ ID NO:29), and a CDR-L3 comprising the amino acid sequence QQYSGYPLT (SEQ ID NO:30). In some embodiments, the antibody comprises a heavy chain comprising a heavy chain variable (VH) domain and a light chain comprising a light chain variable (VL) domain; wherein the VH domain comprises a CDR-H1 comprising the amino acid sequence TNAMN (SEQ ID NO:32), a CDR-H2 comprising the amino acid sequence RIRSKSNNYATYYADSVKD (SEQ ID NO:33), and a CDR-H3 comprising the amino acid sequence GGSYWYFDV (SEQ ID NO:34); and the VL domain comprises a CDR-L1 comprising the amino acid sequence RSSQSIVNSNGNTYLE (SEQ ID NO:36), a CDR-L2 comprising the amino acid sequence KVSNRFS (SEQ ID NO:37), and a CDR-L3 comprising the amino acid sequence FQGSHVPWT (SEQ ID NO:38).

In another aspect, provided herein is a kit or article of manufacture comprising an antibody that specifically binds to human PSGL-1 and a package insert comprising instructions for using the antibody in combination with a Janus kinase (JAK) inhibitor for treating or preventing a T-cell mediated inflammatory disease or cancer in a subject. In some embodiments, the antibody comprises a heavy chain comprising a heavy chain variable (VH) domain and a light chain comprising a light chain variable (VL) domain; wherein the VH domain comprises a CDR-H1 comprising the amino acid sequence SFGMH (SEQ ID NO:8), a CDR-H2 comprising the amino acid sequence YINGGSSTIFYANAVKG (SEQ ID NO:9), and a CDR-H3 comprising the amino acid sequence YASYGGGAMDY (SEQ ID NO:10); and wherein the VL domain comprises a CDR-L1 comprising the amino acid sequence RSSQSIVHNDGNTYFE (SEQ ID NO:5), a CDR-L2 comprising the amino acid sequence KVSNRFS (SEQ ID NO:6), and a CDR-L3 comprising the amino acid sequence FQGSYVPLT (SEQ ID NO:7). In some embodiments, the antibody comprises a heavy chain comprising a heavy chain variable (VH) domain and a light chain comprising a light chain variable (VL) domain; wherein VH domain comprises a CDR-H1 comprising the amino acid sequence AYYIH (SEQ ID NO:24), a CDR-H2 comprising the amino acid sequence RVNPNTGGTSYNPKFKG (SEQ ID NO:25), and a CDR-H3 comprising the amino acid sequence SGSPYYRYDD (SEQ ID NO:26); and the VL domain comprises a CDR-L1 comprising the amino acid sequence RASSTVNSTYLH (SEQ ID NO:28), a CDR-L2 comprising the amino acid sequence GSSNLAS (SEQ ID NO:29), and a CDR-L3 comprising the amino acid sequence QQYSGYPLT (SEQ ID NO:30). In some embodiments, the antibody comprises a heavy chain comprising a heavy chain variable (VH) domain and a light chain comprising a light chain variable (VL) domain; wherein the VH domain comprises a CDR-H1 comprising the amino acid sequence TNAMN (SEQ ID NO:32), a CDR-H2 comprising the amino acid sequence RIRSKSNNYATYYADSVKD (SEQ ID NO:33), and a CDR-H3 comprising the amino acid sequence GGSYWYFDV (SEQ ID NO:34); and the VL domain comprises a CDR-L1 comprising the amino acid sequence RSSQSIVNSNGNTYLE (SEQ ID NO:36), a CDR-L2 comprising the amino acid sequence KVSNRFS (SEQ ID NO:37), and a CDR-L3 comprising the amino acid sequence FQGSHVPWT (SEQ ID NO:38). In some embodiments, the kit or article of manufacture further comprises the JAK inhibitor.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

μM, 1.1 μM, 0.367 μM, and 0.122 μM; antibody 15A7H: 0.03 μg/mL, 0.3 μg/mL, and 3 μg/mL) in activated T cells derived from peripheral blood mononuclear cells (PBMCs) from three donors (Donor 1, FIG. 1A; Donor 2; FIG. 1B; Donor 3, FIG. 1C). An isotype control antibody ("Isotype ctrl") alone or in combination with ruxolitinib was also tested at a concentration of 3 μg/mL control antibody. The level of cell apoptosis, as shown on the y-axis, was assessed as described in Example 1 herein.

FIG. 3B; Donor 3, FIG. 3C). An isotype control antibody ("Isotype ctrl") alone or in combination with ruxolitinib was also tested at a concentration of 3 μg/mL control antibody. The level of cell apoptosis, as shown on the y-axis, was assessed as described in Example 2 herein.

FIGS. 4A-4C provide results of experiments testing the combinatorial effect of ruxolitinib ("RUXO") in combination with anti-PSGL-1 antibodies LH10 (FIG. 4A), c43B6 (FIG. 4B), or h9F9 (FIG. 4C) on activated T cell apoptosis, assessed using Chou-Talalay median effect analysis as described in Example 3 herein. Ruxolitinib and anti-PSGL-1 antibodies were tested at the indicated fixed ratios (3.3:1, 1.1:1, and 0.37:1) for their effect on activated T cell apoptosis in cells derived from the indicated donors (N98, M1, and N136). The x-axis shows the observed apoptosis fractions as compared to untreated control cells, and the y-axis shows the corresponding $Log_{10}$ combination index (CI). Combinatorial effects were defined as "synergistic", "additive" or "antagonistic" when the CI was <1, 1 and >1, respectively.

DETAILED DESCRIPTION

Figure 1A:
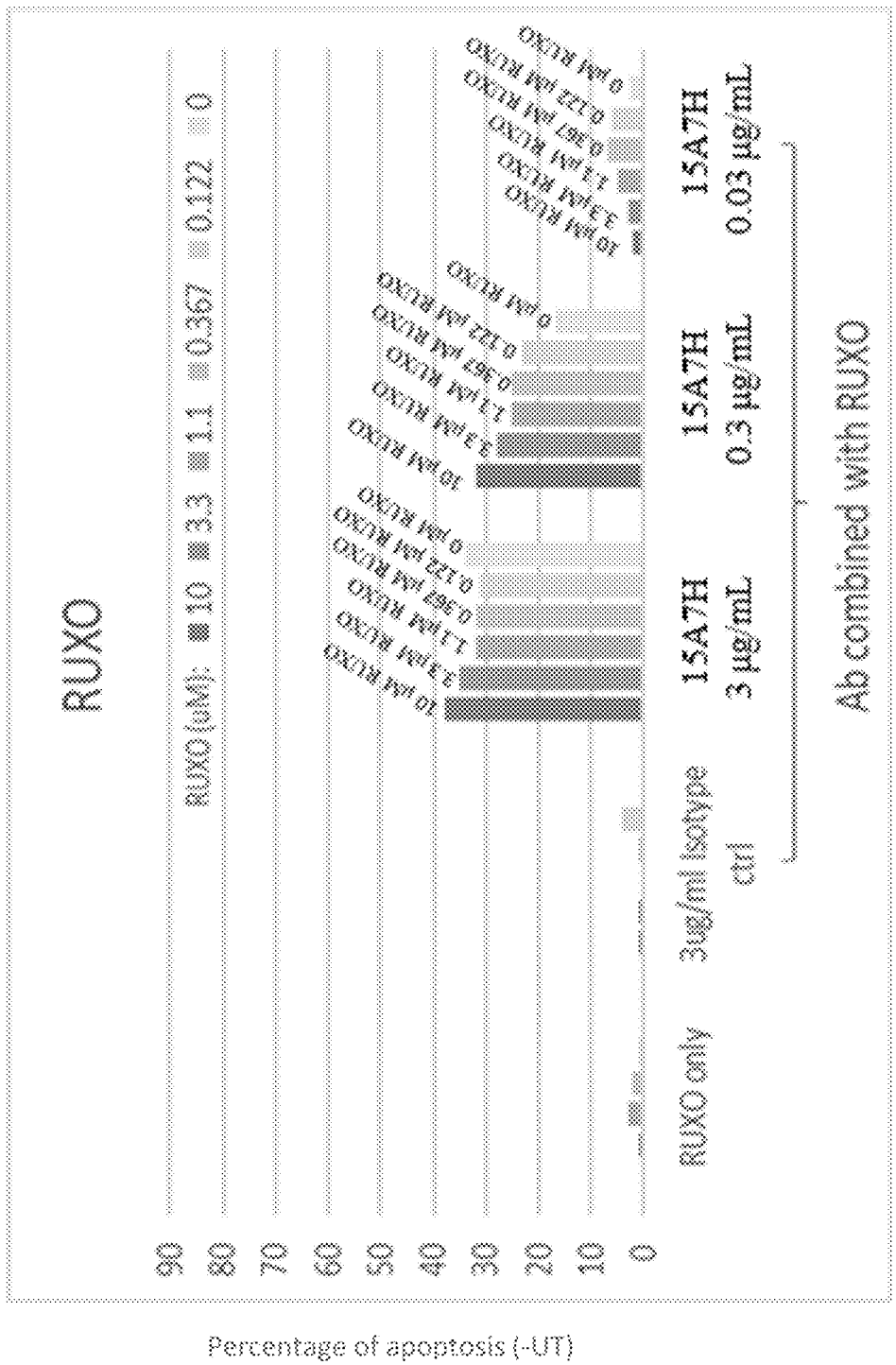
FIGS. 1A-1C provide results of T cell apoptosis assays that tested the synergistic effects of ruxolitinib ("RUXO") in combination with anti-PSGL-1 antibody 15A7H. Ruxolitinib and antibody 15A7H were tested alone or in combination at the indicated concentrations (RUXO: 10 µM, 3.3

Provided herein are methods of treating or preventing a T-cell mediated inflammatory disease or cancer in a subject in need thereof comprising administering to the subject a therapeutically effective amount of an antibody that specifically binds to human PSGL-1 in combination with a Janus kinase (JAK) inhibitor. In some embodiments, the antibody that specifically binds to human PSGL-1 comprises a heavy chain comprising a heavy chain variable (VH) domain and a light chain comprising a light chain variable (VL) domain; wherein the VH domain comprises a CDR-H1 comprising the amino acid sequence SFGMH (SEQ ID NO:8), a CDR-H2 comprising the amino acid sequence YINGGSSTIFYA-NAVKG (SEQ ID NO:9), and a CDR-H3 comprising the amino acid sequence YASYGGGAMDY (SEQ ID NO:10); and wherein the VL domain comprises a CDR-L1 comprising the amino acid sequence RSSQSIVHNDGNTYFE (SEQ ID NO:5), a CDR-L2 comprising the amino acid sequence KVSNRFS (SEQ ID NO:6), and a CDR-L3 comprising the amino acid sequence FQGSYVPLT (SEQ ID NO:7). Further provided herein are related uses and kits/articles of manufacture.

I. Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also polypeptides comprising fragments thereof (such as Fab, Fab', F(ab')$_2$, Fv); single-chain variable fragments (scFv), single-chain diabodies (scDbs), tandem single-chain variable fragment (scFv) units (termed taFv for tandem scFv), and mutants or other configurations thereof; fusion proteins comprising an antibody portion; and any other modified configuration of the immunoglobulin molecule that comprises an antigen recognition site.

An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively. The subunit structures and three-dimensional configurations of different classes of immunoglobulins are well known.

The antibodies of the present disclosure are further intended to include bispecific, multispecific, chimeric, humanized, and recombinantly constructed molecules having affinity for a polypeptide conferred by at least one CDR region of the antibody. Single domain antibodies which are either the variable domain of an antibody heavy chain or the variable domain of an antibody light chain are known in the art. See, e.g., Holt et al., *Trends Biotechnol.* 21:484-490, 2003. Methods of making antibodies comprising either the variable domain of an antibody heavy chain or the variable domain of an antibody light chain, containing three of the six naturally occurring complementarity determining regions from an antibody, are also known in the art. See, e.g., Muyldermans, *Rev. Mol. Biotechnol.* 74:277-302, 2001.

As used herein, "monoclonal antibody" refers to an antibody of substantially homogeneous antibodies, i.e., the individual antibodies comprising the population are identical except for possible naturally-occurring mutations that may be present in minor amounts. Monoclonal antibodies are generally highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, a "chimeric antibody" refers to an antibody having a variable region or part of a variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA,* 81:3273-3277; Harlow and Lane (1988), *Antibodies: a Laboratory Manual,* Cold Spring Harbor Laboratory). Typically, in these chimeric antibodies, the variable region of both light and heavy chains mimics the variable regions of antibodies derived from one species of mammal, while the constant portions are homologous to the sequences in antibodies derived from another. One clear advantage to such chimeric forms is that, for example, the variable regions can conveniently be derived from presently known sources using readily available hybridomas or B-cells from non-human host organisms in combination with constant regions derived from, for example, human cell preparations. While the variable region has the advantage of ease of preparation, and the specificity is not affected by its source, the constant region being human is less likely to elicit an immune response from a human subject when the antibodies are injected than would the constant region from a non-human source. However, the definition is not limited to this particular example. In some embodiments, amino acid modifications are made in the variable and/or constant region.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$, or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (e.g., an Fc domain), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B-lymphocytes that produce an antibody directed against a target antigen (such B-lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A "variable region" (the term "variable domain" may be used interchangeably herein) of an antibody refers to the variable region of the antibody light chain (VL) or the variable region of the antibody heavy chain (VH), either alone or in combination. The variable regions of the heavy and light chain (VH and VL domains, respectively) each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, MD. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra, or and Edelman, G. M. et al. (1969) *Proc. Natl. Acad. Sci. USA* 63:78-85).

"Fv" as used herein may refer to the minimum antibody fragment which contains a complete antigen-recognition and -binding site. This fragment typically consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

A "constant region" (the term "constant domain" may be used interchangeably herein) of an antibody refers to the constant region of the antibody light chain (CL) or the constant region of the antibody heavy chain (CH), either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region is dependent upon the species from which it is derived; however, variations in the amino acid sequence leading to allotypes is relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene. Depending on the antibody isotype, a heavy chain constant region may include a CH1 domain, a hinge region, a CH2 domain, a CH3 domain, and/or a CH4 domain. In certain embodiments, a heavy chain constant region comprises a CH1 domain, a hinge region, a CH2 domain, and a CH3 domain.

The term "Fc region" (the term "Fc domain" may be used interchangeably herein) herein is used to define a C-terminal region of an immunoglobulin heavy chain, including native-sequence Fc regions and variant Fc regions. The boundaries of the Fc region of an immunoglobulin heavy chain might vary; in some embodiments, the Fc region may include one or more amino acids of the hinge region. In some embodiments, the human IgG heavy-chain Fc region is defined to stretch from an amino acid residue at EU position 216 to the carboxyl-terminus thereof. Suitable native-sequence Fc regions for use in the antibodies of the present disclosure include human IgG1, IgG2 (IgG2A, IgG2B), IgG3 and IgG4.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and $V_L$ domains which enables the sFv to form the desired structure for antigen binding. For a review of the sFv, see Pluckthun in *The Pharmacology of Monoclonal Antibodies,* vol. 113, Rosenburg and Moore eds., Springer-Verlag, New York, pp. 269-315 (1994).

The term "diabodies" refers to antibody fragments prepared by constructing sFv fragments (see preceding paragraph) with short linkers (e.g., about 5-12 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The terms "polypeptide," "oligopeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the present disclosure are based upon a tetravalent antibody, the polypeptides can occur as single chains or associated chains.

"Polynucleotide," or "nucleic acid," as used interchangeably herein, refer to polymers of nucleotides of any length, and include DNA and/or RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses, lyxoses, pyranose sugars, furanose sugars, sedoheptuloses, acyclic analogs, and abasic nucleoside analogs such as methyl ribosides. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including RNA and DNA.

As used herein, "vector" means a construct that is capable of delivering and desirably expressing one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, an "effective dosage" or "therapeutically effective amount" of drug, compound, or pharmaceutical composition is an amount sufficient to effect beneficial, desired, and/or therapeutic results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of treating an individual awaiting a transplantation, for example, an effective amount of the drug may reduce to some extent the level of alloantibodies and/or PRA in the individual. In the case of treating an individual receiving a transplantation or transfusion, an effective amount of the drug may have the effect in and/or relieving to some extent one or more of the symptoms or conditions (such as a T-cell mediated inflammatory disease) associated with the transplantation or transfusion. An effective amount can be administered in one or more administrations. For purposes of the present disclosure, an effective amount of drug, compound, or pharmaceutical composition is an amount sufficient to accomplish prophylactic or therapeutic treatment either directly or indirectly. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition (e.g., a JAK inhibitor). Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" or "in combination with" refers to administration of one treatment modality in addition to another treatment modality. As such, "in conjunction with" or "in combination with" refers to administration of one treatment modality before, during, or after administration of the other treatment modality to the individual.

As used herein, "treatment" or "treating" is an approach for obtaining beneficial or desired results, including desirably clinical results. Beneficial, desired, and/or therapeutic clinical results include, but are not limited to, one or more of the following: reducing or abrogating one or more symptoms of inflammation or autoimmunity (e.g., stemming from a T-cell mediated inflammatory disease), increasing the likelihood of a successful patient outcome and/or mitigating one or more contraindications or detrimental outcomes related to a medical treatment (e.g., related to a transplantation or transfusion), decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a symptom of an inflammatory disease, such as a T-cell mediated inflammatory disease, may be delayed.

An "individual" or a "subject" is a mammal, more desirably a human. Mammals also include, but are not limited to, farm animals, sport animals, pets (such as cats, dogs, or horses), primates, mice, and rats.

As used herein, the term "specifically recognizes" or "specifically binds" refers to measurable and reproducible interactions such as attraction or binding between a target and an antibody (e.g., a full-length antibody, an antibody fragment, or an antibody VH-VL binding unit) that is determinative of the presence of the target in the presence of a heterogeneous population of molecules including biological molecules. For example, an antibody, antibody fragment, or antibody VH-VL binding unit that specifically or preferentially binds to an epitope is an antibody that binds this epitope with greater affinity, avidity, more readily, and/or with greater duration than it binds to other epitopes of the target or non-target epitopes. It is also understood by reading this definition that, for example, an antibody, antibody fragment, or antibody VH-VL binding unit that specifically or preferentially binds to a first target may or may not specifically or preferentially bind to a second target. As such, "specific binding" or "preferential binding" does not necessarily require (although it can include) exclusive binding. An antibody, antibody fragment, or antibody VH-VL binding unit that specifically binds to a target may have an association constant of greater than or about $10^3$ $M^{-1}$ or about $10^4$ $M^{-1}$, sometimes about $10^5$ $M^{-1}$ or about $10^6$ $M^{-1}$, in other instances about $10^6$ $M^{-1}$ or about $10^7$ $M^{-1}$, about $10^8$ $M^{-1}$ to about $10^9$ $M^{-1}$, or about $10^{10}$ $M^{-1}$ to about $10^{11}$ $M^{-1}$ or higher. A variety of immunoassay formats can be used to select antibodies, antibody fragments, or antibody VH-VL binding units that are specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the present disclosure described herein include "consisting" and/or "consisting essentially of" aspects and variations.

II. Anti-PSGL-1 Antibodies and Methods of Use

Certain aspects of the present disclosure relate to methods of treating or preventing a T-cell mediated disease by administration of a therapeutically effective amount of an antibody that specifically binds to human PSGL-1 in combination with a Janus kinase (JAK) inhibitor of the present disclosure. Any of the anti-PSGL-1 antibodies of the present disclosure may find use in the methods disclosed herein. In some embodiments, the T-cell mediated disease is a T-cell mediated inflammatory disease. In some embodiments, the T-cell mediated disease is a T-cell mediated cancer (e.g., a T cell leukemia or lymphoma).

In some embodiments, provided herein is an anti-PSGL-1 antibody that comprises at least one, at least two, or all three VL CDR sequences selected from (a) a CDR-L1 comprising the amino acid sequence of SEQ ID NO: 5; (b) a CDR-L2 comprising the amino acid sequence of SEQ ID NO: 6; and (c) a CDR-L3 comprising the amino acid sequence of SEQ ID NO: 7. In some embodiments, the anti-PSGL-1 antibody comprises (a) a CDR-L1 comprising the amino acid sequence of SEQ ID NO: 5; (b) a CDR-L2 comprising the amino acid sequence of SEQ ID NO: 6; and (c) a CDR-L3 comprising the amino acid sequence of SEQ ID NO: 7, e.g., as shown in Table A.

In some embodiments, provided herein is an anti-PSGL-1 antibody that comprises at least one, at least two, or all three VH CDR sequences selected from (a) a CDR-H1 comprising the amino acid sequence of SEQ ID NO: 8; (b) a CDR-H2 comprising the amino acid sequence of SEQ ID NO: 9; and (c) a CDR-H3 comprising the amino acid sequence of SEQ ID NO: 10. In some embodiments, the anti-PSGL-1 antibody comprises (a) a CDR-H1 comprising the amino acid sequence of SEQ ID NO: 8; (b) a CDR-H2 comprising the amino acid sequence of SEQ ID NO: 9; and (c) a CDR-H3 comprising the amino acid sequence of SEQ ID NO: 10, e.g., as shown in Table A.

In some embodiments, provided herein is an anti-PSGL-1 antibody that comprises (a) a VL domain comprising at least one, at least two, or all three VL CDR sequences selected from (i) a CDR-L1 comprising the amino acid sequence of SEQ ID NO: 5; (ii) a CDR-L2 comprising the amino acid sequence of SEQ ID NO: 6; and (iii) a CDR-L3 comprising the amino acid sequence of SEQ ID NO: 7; and (b) a VH domain comprising at least one, at least two, or all three VH CDR sequences selected from (i) a CDR-H1 comprising the amino acid sequence of SEQ ID NO: 8; (ii) a CDR-H2 comprising the amino acid sequence of SEQ ID NO: 9; and (iii) a CDR-H3 comprising the amino acid sequence of SEQ ID NO: 10, e.g., as shown in Table A.

In some embodiments, the anti-PSGL-1 antibody comprises at least one of (a) a CDR-H3 comprising the amino acid sequence of SEQ ID NO: 10; and (b) a CDR-L1 comprising the amino acid sequence of SEQ ID NO: 5, e.g., as shown in Table A. In some embodiments, the anti-PSGL-1 antibody comprises a CDR-H3 comprising the amino acid sequence of SEQ ID NO: 10. In some embodiments, the anti-PSGL-1 antibody comprises a CDR-L1 comprising the amino acid sequence of SEQ ID NO: 5. In some embodiments, the anti-PSGL-1 antibody comprises (a) a CDR-H3 comprising the amino acid sequence of SEQ ID NO: 10; and (b) a CDR-L1 comprising the amino acid sequence of SEQ ID NO: 5.

In some embodiments, provided herein is an anti-PSGL-1 antibody that comprises (a) a heavy chain variable domain (VH) that comprises a CDR-H1 comprising the amino acid sequence of SEQ ID NO: 8, a CDR-H2 comprising the amino acid sequence of SEQ ID NO: 9, and a CDR-H3 comprising the amino acid sequence of SEQ ID NO: 10; and (b) a light chain variable domain (VL) that comprises a CDR-L1 comprising the amino acid sequence of SEQ ID NO: 5, a CDR-L2 comprising the amino acid sequence of SEQ ID NO: 6, and a CDR-L3 comprising the amino acid sequence of SEQ ID NO: 7, e.g., as shown in Table A.

In some embodiments, provided herein is an anti-PSGL-1 antibody that comprises at least one, at least two, or all three VL CDR sequences selected from (a) a CDR-L1 comprising the amino acid sequence of SEQ ID NO: 28; (b) a CDR-L2 comprising the amino acid sequence of SEQ ID NO: 29; and (c) a CDR-L3 comprising the amino acid sequence of SEQ ID NO: 30. In some embodiments, the anti-PSGL-1 antibody comprises (a) a CDR-L1 comprising the amino acid sequence of SEQ ID NO: 28; (b) a CDR-L2 comprising the amino acid sequence of SEQ ID NO: 29; and (c) a CDR-L3 comprising the amino acid sequence of SEQ ID NO: 30, e.g., as shown in Table A. In some embodiments, the anti-PSGL-1 antibody comprises a VL domain from the light chain sequence of SEQ ID NO:31.

In some embodiments, provided herein is an anti-PS GL-1 antibody that comprises at least one, at least two, or all three VH CDR sequences selected from (a) a CDR-H1 comprising the amino acid sequence of SEQ ID NO: 24; (b) a CDR-H2 comprising the amino acid sequence of SEQ ID NO: 25; and (c) a CDR-H3 comprising the amino acid sequence of SEQ ID NO: 26. In some embodiments, the anti-PSGL-1 antibody comprises (a) a CDR-H1 comprising the amino acid sequence of SEQ ID NO: 24; (b) a CDR-H2 comprising the amino acid sequence of SEQ ID NO: 25; and (c) a CDR-H3 comprising the amino acid sequence of SEQ ID NO: 26, e.g., as shown in Table A. In some embodiments, the anti-PSGL-1 antibody comprises a VH domain from the heavy chain sequence of SEQ ID NO:27.

In some embodiments, the anti-PSGL-1 antibody comprises a VH domain comprising: (a) a CDR-H1 comprising the amino acid sequence of SEQ ID NO: 24; (b) a CDR-H2 comprising the amino acid sequence of SEQ ID NO: 25; and (c) a CDR-H3 comprising the amino acid sequence of SEQ ID NO: 26; and a VL domain comprising: (a) a CDR-L1 comprising the amino acid sequence of SEQ ID NO: 28; (b) a CDR-L2 comprising the amino acid sequence of SEQ ID NO: 29; and (c) a CDR-L3 comprising the amino acid sequence of SEQ ID NO: 30, e.g., as shown in Table A. In some embodiments, the anti-PSGL-1 antibody comprises a VH domain from the heavy chain sequence of SEQ ID NO:27 and/or a VL domain from the light chain sequence of SEQ ID NO:31. In some embodiments, the anti-PSGL-1 antibody comprises a heavy chain comprising the amino acid sequence of SEQ ID NO:27 and/or a light chain comprising the amino acid sequence of SEQ ID NO:31.

In some embodiments, provided herein is an anti-PSGL-1 antibody that comprises at least one, at least two, or all three VL CDR sequences selected from (a) a CDR-L1 comprising the amino acid sequence of SEQ ID NO: 36; (b) a CDR-L2 comprising the amino acid sequence of SEQ ID NO: 37; and (c) a CDR-L3 comprising the amino acid sequence of SEQ ID NO: 38. In some embodiments, the anti-PSGL-1 antibody comprises (a) a CDR-L1 comprising the amino acid sequence of SEQ ID NO: 36; (b) a CDR-L2 comprising the amino acid sequence of SEQ ID NO: 37; and (c) a CDR-L3 comprising the amino acid sequence of SEQ ID NO: 38, e.g., as shown in Table A. In some embodiments, the anti-PSGL-1 antibody comprises a VL domain from the light chain sequence of SEQ ID NO:39.

In some embodiments, provided herein is an anti-PS GL-1 antibody that comprises at least one, at least two, or all three VH CDR sequences selected from (a) a CDR-H1 comprising the amino acid sequence of SEQ ID NO: 32; (b) a CDR-H2 comprising the amino acid sequence of SEQ ID NO: 33; and (c) a CDR-H3 comprising the amino acid sequence of SEQ ID NO: 34. In some embodiments, the anti-PSGL-1 antibody comprises (a) a CDR-H1 comprising the amino acid sequence of SEQ ID NO: 32; (b) a CDR-H2 comprising the amino acid sequence of SEQ ID NO: 33; and (c) a CDR-H3 comprising the amino acid sequence of SEQ ID NO: 34, e.g., as shown in Table A. In some embodiments, the anti-PSGL-1 antibody comprises a VH domain from the heavy chain sequence of SEQ ID NO:35.

In some embodiments, the anti-PSGL-1 antibody comprises a VH domain comprising: (a) a CDR-H1 comprising the amino acid sequence of SEQ ID NO: 32; (b) a CDR-H2 comprising the amino acid sequence of SEQ ID NO: 33; and (c) a CDR-H3 comprising the amino acid sequence of SEQ ID NO: 34; and a VL domain comprising: (a) a CDR-L1 comprising the amino acid sequence of SEQ ID NO: 36; (b) a CDR-L2 comprising the amino acid sequence of SEQ ID NO: 37; and (c) a CDR-L3 comprising the amino acid sequence of SEQ ID NO: 38, e.g., as shown in Table A. In some embodiments, the anti-PSGL-1 antibody comprises a VH domain from the heavy chain sequence of SEQ ID NO:35 and/or a VL domain from the light chain sequence of SEQ ID NO:39. In some embodiments, the anti-PSGL-1 antibody comprises a heavy chain comprising the amino acid sequence of SEQ ID NO:35 and/or a light chain comprising the amino acid sequence of SEQ ID NO:39.

Exemplary anti-PSGL-1 antibody sequences, as well as exemplary human PSGL-1 polypeptide sequences, are provided in Table A. In some embodiments, an anti-PSGL-1 antibody comprises the 6 CDR sequences of antibody 15A7H, e.g., as shown in Table A. In some embodiments, an anti-PSGL-1 antibody comprises the VH and/or VL domain sequence(s) of antibody 15A7H, e.g., as shown in Table A. In some embodiments, the anti-PSGL-1 antibody (e.g., a tetravalent anti-PS GL-1 antibody) comprises the amino acid sequence of SEQ ID NO:23. In some embodiments, an anti-PSGL-1 antibody comprises the 6 CDR sequences of antibody c43B6, e.g., as shown in Table A. In some embodiments, an anti-PSGL-1 antibody comprises the VH and/or VL domain sequence(s) of antibody c43B6, e.g., as shown in Table A. In some embodiments, an anti-PSGL-1 antibody comprises the 6 CDR sequences of antibody h9F9, e.g., as shown in Table A. In some embodiments, an anti-PSGL-1 antibody comprises the VH and/or VL domain sequence(s) of antibody h9F9, e.g., as shown in Table A. In some embodiments, the antibody is humanized or chimeric. In some embodiments, the antibody is a tetravalent anti-PSGL-1 antibody.

TABLE A

Exemplary anti-PSGL-1 antibody sequences.

| Description | Sequence | SEQ ID NO |
|---|---|---|
| 15A7H Light Chain amino acid sequence | DIQMTQSPSSLSASVGDRVTITCRSSQSIVHNDGNTYF EWYQQKPGKAPKLLIYKVSNRFSGVPSRFSGSGSGTHF TLTISSLQPEDFATYYCFQGSYVPLTFGQGTKVEIKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 1 |
| 15A7H Heavy Chain amino acid sequence | EVQLVESGGGLVQPGGSLRLSCAASGFTFSSFGMHWVR QAPGKGLEWVAYINGGSSTIFYANAVKGRFTISRDNAK NTLYLQMNSLRAEDTAVYYCARYASYGGGAMDYWGQGT LVTVSSASTKGPSVFPLAPCSRSTSESTAALGCLVKDY FPEPVTVSWNSGALTSGVHTFPAVLQSSGLYSLSSVVT VPSSSLGTKTYTCNVDHKPSNTKVDKRVESKYGPPCPP CPAPEFLGGPSVFLFPPKPKDTLMISRTPEVTCVVVDV SQEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLG | 2 |
| 15A7H VL domain amino acid sequence | DIQMTQSPSSLSASVGDRVTITCRSSQSIVHNDGNTYF EWYQQKPGKAPKLLIYKVSNRFSGVPSRFSGSGSGTHF TLTISSLQPEDFATYYCFQGSYVPLTFGQGTKVEIK | 3 |
| 15A7H VH domain amino acid sequence | EVQLVESGGGLVQPGGSLRLSCAASGFTFSSFGMHWVR QAPGKGLEWVAYINGGSSTIFYANAVKGRFTISRDNAK NTLYLQMNSLRAEDTAVYYCARYASYGGGAMDYWGQGT LVTVSS | 4 |
| 15A7H CDR-L1 amino acid sequence | RSSQSIVHNDGNTYFE | 5 |
| 15A7H CDR-L2 amino acid sequence | KVSNRFS | 6 |
| 15A7H CDR-L3 amino acid sequence | FQGSYVPLT | 7 |
| 15A7H CDR-H1 amino acid sequence | SFGMH | 8 |
| 15A7H CDR-H2 amino acid sequence | YINGGSSTIFYANAVKG | 9 |
| 15A7H CDR-H3 amino acid sequence | YASYGGGAMDY | 10 |
| Amino acid sequence of human PSGL-1 | MPLQLLLLLILLGPGNSLQLWDTWADEAEKALGPLLAR DRRQATEYEYLDYDFLPETEPPEMLRNSTDTTPLTGPG TPESTTVEPAARRSTGLDAGGAVTELTTELANMGNLST DSAAMEIQTTQPAATEAQTTQPVPTEAQTTPLAATEAQ TTRLTATEAQTTPLAATEAQTTPPAATEAQTTQPTGLE AQTTAPAAMEAQTTAPAAMEAQTTPPAAMEAQTTQTTA MEAQTTAPEATEAQTTQPTATEAQTTPLAAMEALSTEP SATEALSMEPTTKRGLFIPFSVSSVTHKGIPMAASNLS VNYPVGAPDHISVKQCLLAILILALVATIFFVCTVVLA VRLSRKGHMYPVRNYSPTEMVCISSLLPDGGEGPSATA NGGLSKAKSPGLTPEPREDREGDDLTLHSFLP | 11 |
| 15A7H IgG4 hinge region amino acid sequence | ESKYGPPCPPCPA | 12 |
| 15A7H VL FR1 amino acid sequence | DIQMTQSPSSLSASVGDRVTITC | 13 |

TABLE A-continued

Exemplary anti-PSGL-1 antibody sequences.

| Description | Sequence | SEQ ID NO |
|---|---|---|
| 15A7H VL FR2 amino acid sequence | WYQQKPGKAPKLLIY | 14 |
| 15A7H VL FR3 amino acid sequence | GVPSRFSGSGSGTHFTLTISSLQPEDFATYYC | 15 |
| 15A7H VL FR4 amino acid sequence | FGQGTKVEIK | 16 |
| 15A7H VH FR1 amino acid sequence | EVQLVESGGGLVQPGGSLRLSCAASGFTFS | 17 |
| 15A7H VH FR2 amino acid sequence | WVRQAPGKGLEWVA | 18 |
| 15A7H VH FR3 amino acid sequence | RFTISRDNAKNTLYLQMNSLRAEDTAVYYCAR | 19 |
| 15A7H VH FR4 amino acid sequence | WGQGTLVTVSS | 20 |
| IgG4 wild-type hinge region amino acid sequence | ESKYGPPCPSCPA | 21 |
| PSGL-1 variant amino acid sequence | MPLQLLLLLILLGPGNSLQLWDTWADEAEKALGPLLAR DRRQATEYEYLDYDFLPETEPPEMLRNSTDTTPLTGPG TPESTTVEPAARRSTGLDAGGAVTELTTELANMGNLST DSAAMEIQTTQPAATEAQTTPLAATEAQTTRLTATEAQ TTPLAATEAQTTPPAATEAQTTQPTGLEAQTTAPAAME AQTTAPAAMEAQTTPPAAMEAQTTQTTAMEAQTTAPEA TEAQTTQPTATEAQTTPLAAMEALSTEPSATEALSMEP TTKRGLFIPFSVSSVTHKGIPMAASNLSVNYPVGAPDH ISVKQCLLAILILALVATIFFVCTVVLAVRLSRKGHMY PVRNYSPTEMVCISSLLPDGGEGPSATANGGLSKAKSP GLTPEPREDREGDDLTLHSFLP | 22 |
| LH10 amino acid sequence (CDRs are underlined) | DIQMTQSPSSLSASVGDRVTITC<u>RSSQSIVHNDGNTYF E</u>WYQQKPGKAPKLLIY<u>KVSNRFS</u>GVPSRFSGSGSGTHF TLTISSLQPEDFATYYC<u>FQGSYVPLT</u>FGQGTKVEIKgg ggsggggsEVQLVESGGGLVQPGGSLRLSCAASGFTFS S<u>FGMH</u>WVRQAPGKGLEWVAY<u>INGGSSTIFYANAVKG</u>RF TISRDNAKNTLYLQMNSLRAEDTAVYYCAR<u>YASYGGGA MDY</u>WGQGTLVTVSSggggsggggsggggsggggsgggg SDIQMTQSPSSLSASVGDRVTITCRSSQSIVHNDGNTY F<u>E</u>WYQQKPGKAPKLLIY<u>KVSNRFS</u>GVPSRFSGSGSGTH FTLTISSLQPEDFATYYCFQGSYVPLTFGQGTKVEIKg gggsggggsEVQLVESGGGLVQPGGSLRLSCAASGFTF SS<u>FGMH</u>WVRQAPGKGLEWVAY<u>INGGSSTIFYANAVKGR</u> FTISRDNAKNTLYLQMNSLRAEDTAVYYCAR<u>YASYGGG AMDY</u>WGQGTLVTVSSggggsaaaESKYGPPC<u>P</u>PCPAPE FLGGPSVFLFPPKPKDTLMISRTPEVTCVVVDVSQEDP EVQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLG | 23 |
| c43B6 CDR-H1 amino acid sequence | AYYIH | 24 |
| c43B6 CDR-H2 amino acid sequence | RVNPNTGGTSYNPKFKG | 25 |

TABLE A-continued

Exemplary anti-PSGL-1 antibody sequences.

| Description | Sequence | SEQ ID NO |
|---|---|---|
| c43B6 CDR-H3 amino acid sequence | SGSPYYRYDD | 26 |
| c43B6 heavy chain amino acid sequence | EVQLQQSGPDLVKPGALVKISCKASGYSFTAYYIHWVK QSHGKSLEWIGRVNPNTGGTSYNPKFKGKAILNVDKSS STAYMELRSLTSEDSAVYYCARSGSPYYRYDDWGQGTT LTVSSASTKGPSVFPLAPCSRSTSESTAALGCLVKDYF PEPVTVSWNSGALTSGVHTFPAVLQSSGLYSLSSVVTV PSSSLGTKTYTCNVDHKPSNTKVDKRVESKYGPPCPPC PAPEFLGGPSVFLFPPKPKDTLMISRTPEVTCVVVDVS QEDPEVQFNWYVDGVEVHNAKTKPREEQFNSTYRVVSV LTVLHQDWLNGKEYKCKVSNKGLPSSIEKTISKAKGQP REPQVYTLPPSQEEMTKNQVSLTCLVKGFYPSDIAVEW ESNGQPENNYKTTPPVLDSDGSFFLYSRLTVDKSRWQE GNVFSCSVMHEALHNHYTQKSLSLSLG | 27 |
| c43B6 CDR-L1 amino acid sequence | RASSTVNSTYLH | 28 |
| c43B6 CDR-L2 amino acid sequence | GSSNLAS | 29 |
| c43B6 CDR-L3 amino acid sequence | QQYSGYPLT | 30 |
| c43B6 light chain amino acid sequence | ENVLTQSPAIMSASPGEKVTMTCRASSTVNSTYLHWFQ QKSGASPKLWIYGSSNLASGVPARFSGSGSGTSYSLTI SSVEAEDAATYYCQQYSGYPLTFGAGTTLELKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC | 31 |
| h9F9 CDR-H1 amino acid sequence | TNAMN | 32 |
| h9F9 CDR-H2 amino acid sequence | RIRSKSNNYATYYADSVKD | 33 |
| h9F9 CDR-H3 amino acid sequence | GGSYWYFDV | 34 |
| h9F9 heavy chain amino acid sequence | EVQLVESGGGLVQPGGSLKLSCAASGFTFNTNAMNWVR QAPGKGLEWVARIRSKSNNYATYYADSVKDRFTISRDD SKSIIYLQMNSLKTEDTGIYYCVRGGSYWYFDVWGTGT TVTVSSASTKGPSVFPLAPCSRSTSESTAALGCLVKDY FPEPVTVSWNSGALTSGVHTFPAVLQSSGLYSLSSVVT VPSSSLGTKTYTCNVDHKPSNTKVDKRVESKYGPPCPP CPAPPVAGGPSVFLFPPKPKDTLMISRTPEVTCVVVDV SQEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLG | 35 |
| h9F9 CDR-L1 amino acid sequence | RSSQSIVNSNGNTYLE | 36 |
| h9F9 CDR-L2 amino acid sequence | KVSNRFS | 37 |
| h9F9 CDR-L3 amino acid sequence | FQGSHVPWT | 38 |

TABLE A-continued

Exemplary anti-PSGL-1 antibody sequences.

| Description | Sequence | SEQ ID NO |
|---|---|---|
| h9F9 light chain amino acid sequence | DVIMTQSPLSLPVSLGQPASISCRSSQSIVNSNGNTYL EWYLQKPGQSPRLLIYKVSNRFSGVPDRFSGSGSGTDF TLKISRVEAEDVGVYYCFQGSHVPWTFGGGTKLEIKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 39 |

In some embodiments, the anti-PSGL-1 antibody is a humanized anti-PSGL1 antibody. In some embodiments, the anti-PSGL-1 antibody comprises CDRs as in any of the embodiments provided herein, and further comprises a human immunoglobulin framework or a human consensus framework. In some embodiments, the humanized anti-PSGL1 antibody comprises (a) a heavy chain variable domain (VH) that comprises a CDR-H1 comprising the amino acid sequence of SEQ ID NO: 8, a CDR-H2 comprising the amino acid sequence of SEQ ID NO: 9, and a CDR-H3 comprising the amino acid sequence of SEQ ID NO: 10; and (b) a light chain variable domain (VL) that comprises a CDR-L1 comprising the amino acid sequence of SEQ ID NO: 5, a CDR-L2 comprising the amino acid sequence of SEQ ID NO: 6, and a CDR-L3 comprising the amino acid sequence of SEQ ID NO: 7, e.g., as shown in Table A.

In some embodiments, the anti-PSGL-1 antibody comprises at least one, two, three, four, five, six, seven, or eight framework regions (FRs) selected from (a) a VL FR1 comprising the amino acid sequence of SEQ ID NO: 13; (b) a VL FR2 comprising the amino acid sequence of SEQ ID NO: 14; (c) a VL FR3 comprising the amino acid sequence of SEQ ID NO: 15; (d) a VL FR4 comprising the amino acid sequence of SEQ ID NO: 16; (e) a VH FR1 comprising the amino acid sequence of SEQ ID NO: 17; (f) a VH FR2 comprising the amino acid sequence of SEQ ID NO: 18; (g) a VH FR3 comprising the amino acid sequence of SEQ ID NO: 19; and (h) a VH FR4 comprising the amino acid sequence of SEQ ID NO: 20, e.g., as shown in Table A.

In some embodiments, the anti-PSGL-1 antibody comprises at least one, two, three, or all four VL FR sequences selected from (a) a VL FR1 comprising the amino acid sequence of SEQ ID NO: 13; (b) a VL FR2 comprising the amino acid sequence of SEQ ID NO: 14; (c) a VL FR3 comprising the amino acid sequence of SEQ ID NO: 15; and (d) a VL FR4 comprising the amino acid sequence of SEQ ID NO: 16. In some embodiments, the anti-PSGL-1 antibody comprises at least one, two, three, or all four VH FR sequences selected from (a) a VH FR1 comprising the amino acid sequence of SEQ ID NO: 17; (b) a VH FR2 comprising the amino acid sequence of SEQ ID NO: 18; (c) a VH FR3 comprising the amino acid sequence of SEQ ID NO: 19; and (d) a VH FR4 comprising the amino acid sequence of SEQ ID NO: 20.

In some embodiments, the anti-PSGL-1 antibody comprises (a) a VL FR1 comprising the amino acid sequence of SEQ ID NO: 13; (b) a VL FR2 comprising the amino acid sequence of SEQ ID NO: 14; (c) a VL FR3 comprising the amino acid sequence of SEQ ID NO: 15; and (d) a VL FR4 comprising the amino acid sequence of SEQ ID NO: 16. In some embodiments, the anti-PSGL-1 antibody comprises (a) a VH FR1 comprising the amino acid sequence of SEQ ID NO: 17; (b) a VH FR2 comprising the amino acid sequence of SEQ ID NO: 18; (c) a VH FR3 comprising the amino acid sequence of SEQ ID NO: 19; and (d) a VH FR4 comprising the amino acid sequence of SEQ ID NO: 20.

In some embodiments, the anti-PSGL-1 antibody comprises a (a) VL domain comprising at least one, at least two, at least three, or all four VL FR sequences selected from (i) a VL FR1 comprising the amino acid sequence of SEQ ID NO: 13; (ii) a VL FR2 comprising the amino acid sequence of SEQ ID NO: 14; (iii) a VL FR3 comprising the amino acid sequence of SEQ ID NO: 15; and (iv) a VL FR4 comprising the amino acid sequence of SEQ ID NO: 16; and (b) a VH domain comprising at least one, at least two, at least three, or all four VH FR sequences selected from (i) a VH FR1 comprising the amino acid sequence of SEQ ID NO: 17; (ii) a VH FR2 comprising the amino acid sequence of SEQ ID NO: 18; (iii) a VH FR3 comprising the amino acid sequence of SEQ ID NO: 19; and (iv) a VH FR4 comprising the amino acid sequence of SEQ ID NO: 20.

In some embodiments, the anti-PSGL-1 antibody comprises a (a) VL domain comprising (i) a VL FR1 comprising the amino acid sequence of SEQ ID NO: 13; (ii) a VL FR2 comprising the amino acid sequence of SEQ ID NO: 14; (iii) a VL FR3 comprising the amino acid sequence of SEQ ID NO: 15; and (iv) a VL FR4 comprising the amino acid sequence of SEQ ID NO: 16; and (b) a VH domain comprising (i) a VH FR1 comprising the amino acid sequence of SEQ ID NO: 17; (ii) a VH FR2 comprising the amino acid sequence of SEQ ID NO: 18; (iii) a VH FR3 comprising the amino acid sequence of SEQ ID NO: 19; and (iv) a VH FR4 comprising the amino acid sequence of SEQ ID NO: 20.

In some embodiments, the anti-PSGL-1 antibody comprises (a) VL domain comprising (i) a VL FR1 comprising the amino acid sequence of SEQ ID NO: 13; (ii) a CDR-L1 comprising the amino acid sequence of SEQ ID NO: 5; (iii) a VL FR2 comprising the amino acid sequence of SEQ ID NO: 14; (iv) a CDR-L2 comprising the amino acid sequence of SEQ ID NO: 6; (v) a VL FR3 comprising the amino acid sequence of SEQ ID NO: 15; (vi) a CDR-L3 comprising the amino acid sequence of SEQ ID NO: 7; and (vii) a VL FR4 comprising the amino acid sequence of SEQ ID NO: 16. In some embodiments, the anti-PSGL-1 antibody comprises (a) VH domain comprising (i) a VH FR1 comprising the amino acid sequence of SEQ ID NO: 17; (ii) a CDR-H1 comprising the amino acid sequence of SEQ ID NO: 8; (iii) a VH FR2 comprising the amino acid sequence of SEQ ID NO: 18; (iv) a CDR-H2 comprising the amino acid sequence of SEQ ID NO: 9; (v) a VH FR3 comprising the amino acid sequence of SEQ ID NO: 19; (vi) a CDR-H3 comprising the amino acid sequence of SEQ ID NO: 10; and (vii) a VH FR4 comprising the amino acid sequence of SEQ ID NO: 20.

In some embodiments, the anti-PSGL-1 antibody comprises (a) VL domain comprising (i) a VL FR1 comprising the amino acid sequence of SEQ ID NO: 13; (ii) a CDR-L1 comprising the amino acid sequence of SEQ ID NO: 5; (iii)

a VL FR2 comprising the amino acid sequence of SEQ ID NO: 14; (iv) a CDR-L2 comprising the amino acid sequence of SEQ ID NO: 6; (v) a VL FR3 comprising the amino acid sequence of SEQ ID NO: 15; (vi) a CDR-L3 comprising the amino acid sequence of SEQ ID NO: 7; and (vii) a VL FR4 comprising the amino acid sequence of SEQ ID NO: 16; and (b) VH domain comprising (viii) a VH FR1 comprising the amino acid sequence of SEQ ID NO: 17; (ix) a CDR-H1 comprising the amino acid sequence of SEQ ID NO: 8; (x) a VH FR2 comprising the amino acid sequence of SEQ ID NO: 18; (xi) a CDR-H2 comprising the amino acid sequence of SEQ ID NO: 9; (xii) a VH FR3 comprising the amino acid sequence of SEQ ID NO: 19; (xiii) a CDR-H3 comprising the amino acid sequence of SEQ ID NO: 10; and (xiv) a VH FR4 comprising the amino acid sequence of SEQ ID NO: 20.

In some embodiments, the anti-PSGL-1 antibody comprises a heavy chain variable domain (VH) comprising a sequence having at least 90%, 91%, 92%, 93%, 94%, 95%, 96%, 97%, 98%, 99%, or 100% sequence identity to the amino acid sequence of SEQ ID NO: 4. In some embodiments, a VH sequence having at least 90%, 91%, 92%, 93%, 94%, 95%, 96%, 97%, 98%, or 99% identity to the amino acid sequence of SEQ ID NO: 4 contains substitutions (e.g., conservative substitutions), insertions, or deletions relative to the reference sequence, but an anti-PSGL-1 antibody comprising that sequence retains the ability to bind to PSGL-1. In some embodiments, a total of 1 to 10 amino acids have been substituted, inserted and/or deleted in SEQ ID NO: 4. In some embodiments, a total of 1 to 5 amino acids have been substituted, inserted and/or deleted in SEQ ID NO: 4. In some embodiments, substitutions, insertions, or deletions occur in regions outside the CDRs (i.e., in the FRs). In some embodiments, the anti-PSGL-1 antibody comprises the VH sequence of SEQ ID NO: 4, including post-translational modifications of that sequence. In some embodiments, the VH comprises one, two or three CDRs selected from: (a) a CDR-H1 comprising the amino acid sequence of SEQ ID NO: 8; (b) a CDR-H2 comprising the amino acid sequence of SEQ ID NO: 9; and (c) a CDR-H3 comprising the amino acid sequence of SEQ ID NO: 10.

(SEQ ID NO: 4)
EVQLVESGGGLVQPGGSLRLSCAASGFTFS<u>SFGMH</u>WVRQAPGKGLEWVA<u>Y</u>

<u>INGGSSTIFYANAVKG</u>RFTISRDNAKNTLYLQMNSLRAEDTAVYYCARY<u>A</u>

<u>SYGGGAMDY</u>WGQGTLVTVSS

In some embodiments, the anti-PSGL-1 antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 3. In certain embodiments, a VL sequence having at least 90%, 91%, 92%, 93%, 94%, 95%, 96%, 97%, 98%, or 99% identity to the amino acid sequence of SEQ ID NO: 3 contains substitutions (e.g., conservative substitutions), insertions, or deletions relative to the reference sequence, but an anti-PSGL-1 antibody comprising that sequence retains the ability to bind to PSGL-1. In certain embodiments, a total of 1 to 10 amino acids have been substituted, inserted and/or deleted in SEQ ID NO: 3. In certain embodiments, a total of 1 to 5 amino acids have been substituted, inserted and/or deleted in SEQ ID NO: 3. In certain embodiments, the substitutions, insertions, or deletions occur in regions outside the CDRs (i.e., in the FRs). In some embodiments, the anti-PSGL-1 antibody comprises the VL sequence of SEQ ID NO: 3, including post-translational modifications of that sequence. In some embodiments, the VL comprises one, two or three CDRs selected from: (a) a CDR-L1 comprising the amino acid sequence of SEQ ID NO: 5; (b) a CDR-L2 comprising the amino acid sequence of SEQ ID NO: 6; and (c) a CDR-L3 comprising the amino acid sequence of SEQ ID NO: 7.

(SEQ ID NO: 3)
DIQMTQSPSSLSASVGDRVTITC<u>RSSQSIVHNDGNTYFE</u>WYQQKPGKAPK

LLIY<u>KVSNRFS</u>GVPSRFSGSGSGTHFTLTISSLQPEDFATYYC<u>FQGSYVP</u>

<u>LTFGQGTKVEIK</u>

In some embodiments, the anti-PSGL-1 antibody comprises a VH as in any of the embodiments provided herein, and a VL as in any of the embodiments provided herein. In some embodiments, the anti-PSGL-1 antibody comprises the VH and the VL sequences in SEQ ID NO: 4 and SEQ ID NO: 3, respectively, including post-translational modifications of those sequences.

In some embodiments, the anti-PSGL-1 antibody comprises an anti-PSGL-1 antibody that binds to the same epitope as an anti-PSGL-1 antibody provided herein. For example, in some embodiments, the anti-PSGL-1 antibody binds to the same epitope as an anti-PSGL-1 antibody comprising a VH comprising the sequence in SEQ ID NO: 4 and a VL comprising the sequence of SEQ ID NO: 3.

In some embodiments, the anti-PSGL-1 antibody is a monoclonal antibody, a chimeric antibody, humanized antibody, or human antibody. In some embodiments, the anti-PSGL-1 antibody is an antigen-binding fragment of an anti-PSGL-1 antibody described herein, e.g., a Fv, Fab, Fab', scFv, diabody, or F(ab')$_2$ fragment. In some embodiments, the anti-PSGL-1 antibody comprises a substantially full length anti-PSGL-1 antibody, e.g., an IgG4 antibody or other antibody class or isotype as described herein.

In some embodiments, the anti-PSGL-1 antibody is of the IgG, IgM, or IgA class. In some embodiments, the anti-PSGL-1 antibody has a human IgG1, IgG2, IgG3, or IgG4 constant domain. In some embodiments, the anti-PSGL-1 antibody has a human IgG4 constant domain. In some embodiments, the anti-PSGL-1 antibody comprises a heavy chain, where the heavy chain comprises an S228P amino acid substitution at residue position 228, according to EU numbering. In some embodiments, the anti-PSGL-1 antibody comprises an IgG4 hinge domain comprising an S228P amino acid substitution at residue position 228, according to EU numbering. In some embodiments, the anti-PSGL-1 antibody comprises an IgG4 hinge domain comprising the amino acid sequence ESKYGPPCPPCPA (SEQ ID NO: 12).

In some embodiments, the anti-PSGL-1 antibody comprises a heavy chain comprising the amino acid sequence of SEQ ID NO: 2, and/or a light chain comprising the amino acid sequence of SEQ ID NO: 1. In some embodiments, the anti-PSGL-1 antibody comprises a heavy chain comprising the amino acid sequence of SEQ ID NO: 2, and a light chain comprising the amino acid sequence of SEQ ID NO: 1.

(SEQ ID NO: 1)
DIQMTQSPSSLSASVGDRVTITC<u>RSSQSIVHNDGNTYFE</u>WYQQKPGKAPK

LLIY<u>KVSNRFS</u>GVPSRFSGSGSGTHFTLTISSLQPEDFATYYC<u>FQGSYVP</u>

<u>LTFGQGTKVEIK</u>RTVAAPSVFIFPPSDEQLKSGTASVVCLLNNFYPREAK

-continued
VQWKVDNALQSGNSQESVTEQDSKDSTYSLSSTLTLSKADYEKHKVYACE

VTHQGLSSPVTKSFNRGEC (SEQ ID NO: 2)
EVQLVESGGGLVQPGGSLRLSCAASGFTFS<u>SFGMHW</u>VRQAPGKGLEWVA<u>Y</u>

<u>INGGSSTIFYANAVKGR</u>FTISRDNAKNTLYLQMNSLRAEDTAVYYCAR<u>YA</u>

<u>SYGGGAMDY</u>WGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG

In some embodiments, the anti-PSGL-1 antibody of the present disclosure comprises, according to numbering in Kabat et al., the CDR-H1, CDR-H2, CDR-H3, CDR-L1, CDR-L2, and CDR-L3 of the anti-PSGL-1 antibody 15A7H. In some embodiments, the anti-PSGL-1 antibody of the present disclosure comprises the CDR-H1, CDR-H2, CDR-H3, CDR-L1, CDR-L2, and CDR-L3 of the anti-PSGL-1 antibody 15A7H. In some embodiments, the anti-PSGL-1 antibody of the present disclosure comprises the VH domain and/or the VL domain of the anti-PSGL-1 antibody 15A7H. In some embodiments, the anti-PSGL-1 antibody of the present disclosure comprises the VH domain and the VL domain of the anti-PSGL-1 antibody 15A7H. In some embodiments, the anti-PSGL-1 antibody of the present disclosure comprises the heavy chain and/or the light chain of the anti-PSGL-1 antibody 15A7H. In some embodiments, the anti-PSGL-1 antibody of the present disclosure comprises the heavy chain and the light chain of the anti-PSGL-1 antibody 15A7H. The anti-PSGL-1 antibody 15A7H is described in US20130209449 and US20130011391. Additional anti-PSGL-1 antibodies which may be used in the methods provided herein are described in U.S. Pat. Nos. 7,604,800 and 8,361,472.

In some embodiments, the anti-PSGL-1 antibody of the present disclosure is a tetravalent anti-PSGL-1 antibody. Exemplary tetravalent anti-PSGL-1 antibodies are disclosed in WO2017120534.

Human PSGL-1 may also be referred to as selectin P ligand, SELPG, CLA, CD162, or PSGL1. In some embodiments, an antibody of the present disclosure binds to a polypeptide encoded by the human SELPG gene, e.g., as described by NCBI RefSeq Gene ID No. 6404. In some embodiments, an antibody of the present disclosure binds to a polypeptide comprising the amino acid sequence MPLQLLLLLILLGPGNSLQLWDTWADEAEKALGPLLARDRRQATEYEYLDYDFLPETEPPE MLRNSTDTTPLTGPGTPESTTVEPAARRSTGLDAGGAVTELTTELANMGNLSTDSAAMEIQ TTQPAATEAQTTQPVPTEAQTTPLAATEAQTTRLTATEAQTTPLAATEAQTTPPAATEAQT TQPTGLEAQTTAPAAMEAQTTAPAAMEAQTTPPAAMEAQTTQTTAMEAQTTAPEATEAQTT QPTATEAQTTPLAAMEALSTEPSATEALSMEPTTKRGLFIPFSVSSVTHKGIPMAASNLSV NYPVGAPDHISVKQCLLAILILALVATIFFVCTVVLAVRLSRKGHMYPVRNYSPTEMVCIS SLLPDGGEGPSATANGGLSKAKSPGLTPEPREDREGDDLTLHSFLP (SEQ ID NO:11). In some embodiments, an antibody of the present disclosure binds to a polypeptide comprising the amino acid sequence MPLQLLLLLILLGPGNSLQLWDTWADEAEKALGPLLARDRRQATEYEYLDYDFLPETEPPE MLRNSTDTTPLTGPGTPESTTVEPAARRSTGLDAGGAVTELTTELANMGNLSTDSAAMEIQ TTQPAATEAQTTPLAATEAQTTRLTATEAQTTPLAATEAQTTPPAATEAQTTQP TGLEAQT TAPAAMEAQTTAPAAMEAQTTPPAAMEAQTTQTTAMEAQTTAPEATEAQTTQPTATEAQTT PLAAMEALSTEPSATEALSMEPTTKRGLFIPFSVSSVTHKGIPMAASNLSVNYPVGAPDHI SVKQCLLAILILALVATIFFVCTVVLAVRLSRKGHMYPVRNYSPTEMVCISSLLPDGGEGP SATANGGLSKAKSPGLTPEPREDREGDDLTLHSFLP (SEQ ID NO:22). The amino acid sequence of SEQ ID NO:11 depicts full length human PSGL-1, GenBank™ accession number AAA74577.1, GL902797, and the amino acid sequence of SEQ ID NO:22 depicts the shorter 402 amino acid human PSGL-1 protein (GenBank™ accession number XP_005269133). In specific embodiments, an antibody described herein specifically binds to human PSGL-1 as determined, e.g., by ELISA or other antigen-binding assay known in the art, or described herein.

The present disclosure encompasses modifications to antibodies or polypeptide described herein, including functionally equivalent antibodies which do not significantly affect their properties and variants which have enhanced or decreased activity and/or affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in the table below under the heading of "conservative substitutions." If such substitutions result in a change in biological activity, then more substantial changes, denominated "exemplary substitutions" in the table below, or as further described below in reference to amino acid classes, may be introduced and the products screened.

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |

| Original Residue | Conservative Substitutions | Exemplary Substitutions |
| --- | --- | --- |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

In some embodiments, an anti-PSGL-1 antibody of the present disclosure comprises an antibody constant domain. In some embodiments, the antibody constant domain is a human antibody constant domain. In certain embodiments, the antibody constant domain is a human IgG4 constant domain. In some embodiments, the human IgG4 constant domain comprises a Serine to Proline amino acid substitution at amino acid position 228 of the heavy chain numbered according to the EU index (also known as position 241 using Kabat numbering).

In some embodiments, one or more amino acid residues in the heavy chain constant region and/or the light chain constant region of the antibody are modified. In some embodiments, the Fc region of antibodies is modified to enhance or reduce ADCC and/or CDC activities of the antibodies. See Shields et al., J. Biol. Chem. 276:6591-6604 (2001); Presta et al., Biochem. Soc. Trans. 30:487-490 (2002).

The present disclosure also provides polynucleotides comprising a polynucleotide encoding any of the tetravalent antibodies and/or polypeptides described herein. In some embodiments, the polypeptides comprise the sequences of light chain and heavy chain variable regions. In some embodiments, the polynucleotide is an isolated polynucleotide (e.g., isolated from a host cell or from one or more different polynucleotides).

It is appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Thus, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions, and/or substitutions of nucleotides. The resulting mRNA and protein can, but need not, have an altered structure or function. Alleles can be identified using standard techniques (such as hybridization, amplification, and/or database sequence comparison).

The polynucleotides of the present disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides can be inserted into host cells by any means known in the art. Cells are transformed by introducing an exogenous polynucleotide by direct uptake, endocytosis, transfection, F-mating, or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195; 4,800,159; 4,754,065; and 4,683,202, as well as PCR: The Polymerase Chain Reaction, Mullis et al. eds., Birkauswer Press, Boston (1994).

The present disclosure also provides vectors (e.g., cloning vectors or expression vectors) comprising a nucleic acid sequence encoding any of the polypeptides (including antibodies) described herein. Suitable cloning vectors can be constructed according to standard techniques or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; and suitable transcriptional controlling elements (such as promoters, enhancers, or terminator). For expression (i.e., translation), one or more translational controlling elements are also usually required, such as ribosome binding sites, translation initiation sites, or stop codons.

Methods of making antibodies and polypeptides derived from the antibodies are known in the art and are disclosed herein. Well-established methods may be used to identify anti-PSGL antibodies (e.g., antibodies that specifically bind to human PSGL-1), from which variable domains (e.g., VH and/or VL domains) may be used in the antibodies of the present disclosure. Exemplary anti-human PSGL-1 antibodies, as well as methods for screening, producing, and purifying such antibodies, are described in International Application Pub. No. WO 2012/174001.

A wide variety of recombinant host-vector expression systems for eukaryotic cells are known and can be used in the present disclosure. For example, *Saccharomyces cerevisiae*, or common baker's yeast, is the most commonly used among eukaryotic microorganisms, although a number of other strains, such as *Pichia pastoris*, are available. Cell lines derived from multicellular organisms such as Sp2/0 or Chinese Hamster Ovary (CHO), which are available from the ATCC, may also be used as hosts. Typical vector plasmids suitable for eukaryotic cell transformations are, for example, pSV2neo and pSV2gpt (ATCC), pSVL and pSVK3 (Pharmacia), and pBPV-1/pML2d (International Biotechnology, Inc.).

The eukaryotic host cells useful in the present disclosure are, for example, hybridoma, myeloma, plasmacytoma, or lymphoma cells. However, other eukaryotic host cells may be suitably utilized provided the mammalian host cells are capable of recognizing transcriptional and translational DNA sequences for expression of the proteins; processing the leader peptide by cleavage of the leader sequence and secretion of the proteins; and providing post-translational modifications of the proteins, e.g., glycosylation.

Accordingly, the present disclosure provides host cells (e.g., eukaryotic host cells) which are transformed by recombinant expression vectors comprising DNA constructs disclosed herein and which are capable of expressing the tetravalent antibodies or polypeptides of the present disclosure. In some embodiments, the transformed host cells of the present disclosure comprise at least one DNA construct comprising a polynucleotide of the present disclosure, or a polynucleotide expressing a monomer, dimer, or tetravalent antibody of the present disclosure, and transcriptional and translational regulatory sequences which are positioned in relation to the coding DNA sequences to direct expression of antibodies or polypeptides.

Any host cells capable of over-expressing heterologous DNAs can be used for the purpose of isolating the genes encoding the antibody, polypeptide, or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe,* or *K. lactis*).

The host cells used in the present disclosure may be transformed in a variety of ways by standard transfection procedures well known in the art. Among the standard transfection procedures which may be used are electroporation techniques, protoplast fusion and calcium-phosphate precipitation techniques. Such techniques are generally described by F. Toneguzzo et al. (1986), *Mol. Cell. Biol.,* 6:703-706; G. Chu et al., *Nucleic Acid Res.* (1987), 15:1311-1325; D. Rice et al., *Proc. Natl. Acad. Sci. USA* (1979), 79:7862-7865; and V. Oi et al., *Proc. Natl. Acad. Sci. USA* (1983), 80:825-829. The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides often depends on features of the host cell.

Certain aspects of the present disclosure relate to antibody variable domains and/or antibody fragments, e.g., that may be used as a constituent of a tetravalent antibody described herein. Antibody fragments may contain the active binding region of the antibodies, such as Fab, F(ab')$_2$, scFv, Fv fragments, and the like. Various methods known in the art may be used to produce and/or isolate antibody fragments, which may be incorporated into a tetravalent antibody of the present disclosure, e.g., by standard recombinant techniques known in the art based on the concepts described herein.

Single-chain Fv fragments may be produced, such as described in Iliades et al., 1997, *FEBS Letters,* 409:437-441. Coupling of such single-chain fragments using various linkers is described in Kortt et al., 1997, *Protein Engineering,* 10:423-433. A variety of techniques for the recombinant production and manipulation of antibodies are well known in the art. Such fragments can be produced from the monoclonal antibodies described herein using techniques well established in the art (Rousseaux et al. (1986), in *Methods Enzymol.,* 121:663-69 Academic Press).

Methods of preparing antibody fragments are well known in the art. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by U.S. Pat. Nos. 4,036,945 and 4,331,647 and references contained therein, which patents are incorporated herein by reference. Also, see Nisonoff et al. (1960), *Arch Biochem. Biophys.* 89: 230; Porter (1959), *Biochem. J.* 73: 119; Smyth (1967), Methods in Enzymology 11: 421-426. Alternatively, the Fab can be produced by inserting DNA encoding Fab of the antibody into an expression vector for prokaryote or an expression vector for eukaryote, and introducing the vector into a prokaryote or eukaryote to express the Fab.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes, and the like. Various methods have been proposed to alter the glycosylation pattern achieved in a particular host organism including introducing or overexpressing certain enzymes involved in oligosaccharide production (U.S. Pat. Nos. 5,047,335; 5,510,261; and 5,278,299). Glycosylation, or certain types of glycosylation, can be enzymatically removed from the glycoprotein, for example using endoglycosidase H (Endo H), N-glycosidase F, endoglycosidase F1, endoglycosidase F2, or endoglycosidase F3. In addition, the recombinant host cell can be genetically engineered to be defective in processing certain types of polysaccharides. These and similar techniques are well known in the art.

In some embodiments, an antibody of the present disclosure is modified using coupling techniques known in the art, including, but not limited to, enzymatic means, oxidative substitution, and chelation. Modifications can be used, for example, for attachment of labels for immunoassay.

In some embodiments, an antibody of the present disclosure may be conjugated (for example, linked) to an agent, such as a therapeutic agent or a label. Examples of therapeutic agents are radioactive moieties, cytotoxins, and chemotherapeutic molecules.

III. JAK Inhibitors

Certain aspects of the present disclosure relate to JAK inhibitors. Any of the JAK inhibitors of the present disclosure may find use in the methods disclosed herein, e.g., by administration in combination with an anti-PSGL-1 antibody of the present disclosure.

In some embodiments, the JAK inhibitor inhibits JAK1 and/or JAK2. In some embodiments, the JAK inhibitor inhibits JAK1 and/or JAK3. In some embodiments, the JAK inhibitor is a JAK1/JAK2 inhibitor, a JAK2/FLT3 inhibitor, a JAK2$^{v617F}$ inhibitor, a JAK2 inhibitor, JAK1 inhibitor, or a JAK2/Src inhibitor, including pharmaceutically acceptable salts thereof. Exemplary and non-limiting descriptions of JAK inhibitors can be found in WO2007070514, WO2008157208, and WO2019171326.

In some embodiments, the JAK inhibitor is ruxolitinib or a pharmaceutically acceptable salt thereof. As known in the art, ruxolitinib is the JAK1/JAK2 inhibitor (R)-3-(4-(7H-pyrrolo[2,3-d]pyrimidin-4-yl)-1 H-pyrazol-1-yl)-3-cyclopentylpropanenitrile, also named 3(R)-Cyclopentyl-3-[4-(7H-pyrrolo[2,3-d]pyrimidin-4-yl)-1H-pyrazol-1-yl] propanenitrile, of formula:

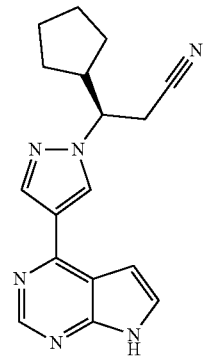 [SMILES: N#CC[C@H](C1CCCC1)n1cc(-c2ncnc3[nH]ccc23)cn1]

In some embodiments, ruxolitinib refers to the ruxolitinib phosphate salt. In some embodiments, ruxolitinib is in a unit dosage form (e.g. tablet). In some embodiments, ruxolitinib is administered orally.

In some embodiments, the JAK inhibitor is tofacitinib or a pharmaceutically acceptable salt thereof.

IV. Methods and Uses

Certain aspects of the present disclosure relate to methods and uses for the antibodies described herein, e.g., by administration to a subject in combination with a JAK inhibitor of the present disclosure for treating or preventing a T-cell mediated disease, e.g., a T-cell mediated inflammatory disease or cancer (e.g., T cell leukemia or lymphoma). In some embodiments, the subject is a human.

As described herein, PSGL-1 is known to be involved in inflammation and T cell biology. The antibodies of the present disclosure that specifically bind human PSGL-1 may find use, inter alia, in treating individuals with diseases related to T cell function (e.g., a T-cell mediated inflammatory disease), or individuals in need of medical procedures that may result in inflammatory conditions such as immunological reactions, or for which such conditions are managed beforehand (e.g., a transplantation or transfusion), e.g., in combination with a JAK inhibitor of the present disclosure.

In some embodiments, the T-cell mediated inflammatory disease is graft-versus-host disease (GVHD), e.g., acute or chronic GVHD. In some embodiments, the T-cell mediated inflammatory disease is steroid-refractory acute GVHD (SR-aGVHD) or treatment-refractory acute GVHD (TR-aGVHD). See, e.g., Przepiorka et al., (2019) The Oncologist, 24:1-7 and Mothy et al., (2020) Blood, 136(17):1903-1906.

In some embodiments, the T-cell mediated inflammatory disease is selected from the group consisting of: a skin disorder, multiple sclerosis, rheumatoid arthritis, juvenile arthritis, type I diabetes, lupus, inflammatory bowel disease, Crohn's disease, myasthenia gravis, immunoglobulin nephropathies, myocarditis, and autoimmune thyroid disorder.

Other aspects of the present disclosure relate to methods and uses for the antibodies described herein, e.g., by administration to a subject in combination with a JAK inhibitor of the present disclosure for treating or preventing a T-cell leukemia or T-cell lymphoma (e.g., adult T cell leukemia/lymphoma (ATLL), anaplastic large cell lymphoma (ALCL), or cutaneous T-cell lymphoma (CTCL)). In some embodiments, the subject is a human.

In some embodiments, the JAK inhibitor is administered to the subject before, after, or simultaneous with administration of the antibody.

In some embodiments, prior to administration of the antibody and/or the JAK inhibitor, the subject has had one or more systemic treatments, e.g., for a T-cell mediated inflammatory disease of the present disclosure such as GVHD. In some embodiments, prior to administration of the antibody and/or the JAK inhibitor, the subject has been treated with a corticosteroid.

In some embodiments, a disorder or disease treated by the methods described herein may be a T-cell mediated disease. Non-limiting examples of disorders and diseases that can be treated, or one or more of whose symptoms may be ameliorated or prevented using the antibodies and JAK inhibitors described herein include psoriasis, Crohn's disease, ankylosing spondylitis, arthritis (including rheumatoid arthritis, juvenile rheumatoid arthritis, osteoarthritis, and psoriatic arthritis), diabetes mellitus, multiple sclerosis, encephalomyelitis, myasthenia gravis, systemic lupus erythematosus, autoimmune thyroiditis, dermatitis (including atopic dermatitis and eczematous dermatitis), Sjogren's Syndrome, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, graft versus host disease (GVHD) (e.g., acute or chronic GVHD), transplantation rejection, vitiligo, alopecia areata, cytokine release syndrome, hidradenitis suppurativa, sarcoidosis, primary biliary cirrhosis, uveitis posterior, interstitial lung fibrosis, allergies such as atopic allergy, AIDS, and T cell neoplasms such as leukemias or lymphomas.

In another embodiment, the disease or disorder treated in accordance with the methods described herein is plaque psoriasis. Plaque psoriasis or psoriasis vulgaris is the most common form of psoriasis and is characterized by sharply demarcated, raised erythematous skin plaques covered by silvery scale. There is a predilection of the lesions to involve the extensor surfaces of the extremities, the lumbosacral area, and the scalp. The corresponding histopathological findings include significant inflammatory cellular infiltration of the dermis and epidermis, increased numbers of dilated vessels, and a substantial thickening of the epidermis with disordered differentiation of keratinocytes and hyperkeratosis. Approximately one third of patients with plaque psoriasis are categorized as having moderate or severe disease and are consequently candidates for therapy beyond just topical treatment.

In another embodiment, the disorder treated in accordance with the methods described herein is chronic plaque psoriasis. Symptoms of plaque chronic psoriasis include, but are not limited to, single or multiple raised reddened patches of skin, ranging from coin-sized to larger, on any part of the body, including but not limited to the knees, elbows, lumbosacral regions, scalp, and nails.

In another embodiment, the disorder treated in accordance with the methods described herein is guttate psoriasis. Symptoms of guttate psoriasis include, but are not limited to, flares of water drop shaped scaly plaques on the skin, followed by an infection, such as a streptococcal throat infection.

In another embodiment, the disease or disorder treated in accordance with the methods described herein is inverse psoriasis. Symptoms of inverse psoriasis include, but are not limited to, smooth, usually moist areas of skin that are red and inflamed, unlike the scaling associated with plaque psoriasis, on one or more of the following body parts: armpits, groin, under the breasts, and in other skin folds around the genitals and buttocks.

In another embodiment, the disease or disorder treated in accordance with the methods described herein is pustular psoriasis. Symptoms of pustular psoriasis include, but are not limited to, pus-filled blisters that vary in size and location, but mostly on the hands and feet.

In another embodiment, the disease or disorder treated in accordance with the methods described herein is erythodermic psoriasis. Symptoms of erythodermic psoriasis include, but are not limited to, periodic, widespread, fiery redness of the skin and the shedding of scales in sheets, rather than smaller flakes. The reddening and shedding of the skin are often accompanied by severe itching and pain, heart rate increase, and fluctuating body temperature.

In another embodiment, the disease or disorder treated in accordance with the methods described herein is rheumatoid arthritis. Symptoms of rheumatoid arthritis, include, but are not limited to, fatigue, loss of appetite, low fever, swollen glands, weakness, joint pain in wrists, elbows, shoulders, hips, knees, ankles, toes, jaw, hands, feet, fingers, and/or neck, morning stiffness, chest pain when taking a breath (pleurisy), eye burning, itching, and discharge, nodules under the skin, numbness, tingling, or burning in the hands and feet.

In another embodiment, the disease or disorder treated in accordance with the methods described herein is Crohn's disease. Symptoms of Crohn's disease, but are not limited to, crampy abdominal (belly area) pain, fever, fatigue, loss of appetite, pain with passing stool (tenesmus), persistent, watery diarrhea, unintentional weight loss, constipation, eye inflammation, fistulas (usually around the rectal area, may cause draining of pus, mucus, or stools), joint pain, liver inflammation, mouth ulcers, rectal bleeding and bloody stools, skin lumps or sores (ulcers), and swollen gums.

In another embodiment, the disease or disorder treated in accordance with the methods described herein is ankylosing spondylitis. Symptoms of ankylosing spondylitis include, but are not limited to, frequent pain and stiffness in the lower back and buttocks, spine, and/or neck; and pain and tenderness spreading to the ribs, shoulder blades, hips, thighs and heels; inflammation of the eye (iridocyclitis and uveitis), causing redness, eye pain, vision loss, floaters and photophobia; fatigue; and nausea.

In another embodiment, the disease or disorder treated in accordance with the methods described herein is diabetes mellitus. Symptoms of diabetes mellitus include, but are not limited to, loss of weight, polyuria (frequent urination), polydipsia (increased thirst), polyphagia (increased hunger), cardiovascular disease, diabetic retinopathy, diabetic neuropathy, hyperosmolar nonketotic state, and diabetic ketoacidosis.

In some embodiments, an antibody or composition of the present disclosure may be administered to the individual in combination with a JAK inhibitor before, concurrently with, and/or after a transplantation.

As used herein, treating an individual in need of a transplantation may refer to one or more of therapeutic treatment and prophylactic or preventative measures (e.g., increasing the likelihood of a favorable treatment outcome, such as graft survival, graft function, or decreasing the likelihood of an unfavorable outcome, such as an unfavorable response to treatment, or a condition that reduces the likelihood a favorable treatment, such as a transplantation, from occurring). Treating may include without limitation mitigating or preventing conditions and symptoms associated with a disorder or a condition, and/or problems or conditions that interfere with or limit an individual's access to treatment options of a disorder or a condition, such as sensitization, hypersensitization, high panel reactive antibodies (PRA) level and/or presence of pre-existing alloantibodies that limit availability of grafts to an individual awaiting a transplantation. Those in need of treatment include those already with the disorder or condition, as well as those in which the disorder or condition is to be prevented. Treatment of a disorder or condition may suppress immune-mediated events associated with the disorder or condition, ameliorate the symptoms of the disorder or condition, reduce the severity of the disorder or condition, alter the course of the disorder or condition progression, and/or ameliorate or cure the basic disorder or condition.

For example, successful treatment of an individual awaiting transplantation include, but is not limited to, reducing the level of alloantibodies, reducing panel reactive antibodies (PRA), enabling the individual to have more cross-match compatible donors, increasing the likelihood or probability of the individual to receive a graft, shortening the expected waiting period of the individual for a graft, desensitizing the individual, lowering risk of transplant-associated symptoms or conditions (such as immune-mediated events as described below), or any combination thereof.

For example, successful treatment of an individual receiving a transplantation includes, but is not limited to, protection and maintenance of the transplanted organ or tissue for a long term, which comprises controlling, reversing, mitigating, delaying, or preventing one or more symptoms or undesirable conditions associated with the organ transplant, such as immune-mediated events, including, but not limited to, production of donor-specific alloantibodies (DSA), GVHD, antibody-mediated rejection (AMR), hyperacute graft rejection, chronic graft rejection, graft failure, and graft loss, as measured by functional or histological signs of the symptom or condition. A treatment capable of controlling a disorder or condition (e.g., graft rejection) may include a treatment that slows the progression of the disease process, when initiated after functional or histological signs of the disorder or condition (e.g., graft rejection) are observed. Further, a treatment capable of reversing a disease or condition (e.g., graft rejection) may include a treatment that, when initiated after functional or histological signs of the disease or condition (e.g., graft rejection) have appeared, reverses the disease process and returns functional and histological findings closer to normal. A treatment capable of "delaying progression" of a disorder or condition (e.g., graft rejection) may include deferring, hindering, slowing, retarding, stabilizing, and/or postponing development of the disorder or condition (e.g., graft rejection). This delay can be of varying lengths of time, depending on the history of the disease and/or individual being treated. As is evident to one skilled in the art, a sufficient or significant delay can, in effect, encompass prevention, in that the individual, e.g., an individual at risk for developing the disorder or condition, does not develop the disorder or condition.

In some embodiments, a transplantation of the present disclosure may be transplantation of one or more tissues or organs including without limitation bone marrow, kidney, heart, liver, neuronal tissue, lung, pancreas, skin, and intestine (e.g., small and/or large intestine, as well as any sub-tissues thereof).

In addition, antibodies in combination with a JAK inhibitor are useful for preventing and/or treating certain disorders and diseases associated with or caused (in whole or in part) by increased proliferation and/or numbers of activated T cells relative to the proliferation and/or numbers of activated T cells found in healthy individuals or individuals not having the particular disorder or disease. Non-limiting examples of disorders and diseases that can be prevented and/or treated using the antibodies described herein in combination with a JAK inhibitor include graft-versus-host disease and cases of transplantation rejection (including transplantation rejection using allogeneic or xenogeneic tissues) such as bone marrow transplantation, liver transplantation, kidney transplant, or the transplantation of any organ or tissue.

In some embodiments, an antibody or composition of the present disclosure may be administered to the individual in combination with a JAK inhibitor before, concurrently with, and/or after a transfusion. For example, as described in greater detail below, a tetravalent antibody or composition of the present disclosure may be administered to increase the likelihood of a favorable treatment outcome, decrease the likelihood of an unfavorable outcome, and/or mitigate or prevent symptoms occurring before, concurrently with, or after the transfusion has been completed.

As used herein, treating an individual in need of a transfusion may refer to one or more of therapeutic treatment and prophylactic or preventative measures (e.g., increasing the likelihood of a favorable treatment outcome, such as replacement or supplementation of blood components/cells, or decreasing the likelihood of an unfavorable outcome, such as an unfavorable response to treatment, inefficacy of treatment, or immunological reaction, or a condition that reduces the likelihood a favorable treatment, such as a transfusion, from occurring). Treating may include without limitation mitigating or preventing conditions and symptoms associated with a disorder or a condition, and/or problems or conditions that interfere with or limit an individual's access to treatment options of a disorder or a condition. Those in need of treatment include those already with the disorder or condition, as well as those in which the disorder or condition is to be prevented. Treatment of a disorder or condition may suppress immune-mediated events associated with the disorder or condition, ameliorate the symptoms of the disorder or condition, reduce the severity of the disorder or condition, alter the course of the disorder or condition progression, and/or ameliorate or cure the basic disorder or condition.

In some embodiments, the transfusion is a transfusion comprising one or more of white blood cells, red blood cells, and platelets. In some embodiments, the transfusion comprises whole blood or one or more blood products, including without limitation white blood cells, red blood cells, platelets, fresh frozen plasma, cryoprecipitate or blood clotting factors, antibodies, and/or blood substitutes. Exemplary conditions that may be treated with a transfusion (e.g., transfusion of blood or a blood product) include without limitation hemorrhage or blood loss, reduced hematocrit or hemoglobin (e.g., anemia), sickle cell disease, thalassemia, blood supplementation during or after surgical procedures, cardiac disease, traumatic injury, deficiency of one or more blood factors (e.g., hemophilia, von Willebrand disease, hypofibrinogenemia, or a deficiency in factor II, V, VII, IX, X, or XI), conditions requiring fibrinogen supplementation (e.g., liver disease, blood transfusion, etc.), bone marrow failure, platelet function disorders, thrombocytopenia, immunodeficiency (e.g., from a therapy or disease), and the like. Descriptions of practices, dosing, responses, indications, and preparations related to transfusions may be found, e.g., in the American Red Cross Compendium of Transfusion Practice Guidelines.

In some embodiments, administration of an antibody of the present disclosure in combination with a JAK inhibitor of the present disclosure to a subject results in a reduction in one or more symptoms of a T-cell mediated inflammatory disease of the present disclosure in the subject.

The dosage and frequency of administration of an antibody and/or JAK inhibitor described herein or a pharmaceutical composition thereof is administered in accordance with the methods for preventing and/or treating while minimizing side effects. The exact dosage of an antibody described herein to be administered in combination with a JAK inhibitor to a particular subject or a pharmaceutical composition thereof can be determined by a practitioner, in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of an antibody described herein or a pharmaceutical composition thereof in combination with a JAK inhibitor can be adjusted over time to provide sufficient levels of the antibody or JAK inhibitor, or to maintain the desired effect.

The precise dose to be employed in the formulation will also depend on the route of administration, and the seriousness of an inflammatory disorder or disease, and should be decided according to the judgment of the practitioner and each patient's circumstances.

Effective doses can be extrapolated from dose-response curves derived from in vitro or animal model test systems.

In one embodiment, any of the antibodies and/or JAK inhibitors described herein is formulated for administration by intraperitoneal, intravenous, subcutaneous, or intramuscular injections, or other forms of administration such as oral, mucosal, via inhalation, sublingually, etc. In some embodiments, the antibody is administered by intravenous infusion and/or the JAK inhibitor is administered orally.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, enteric administration, intracerebral administration, nasal administration, intraarterial administration, intracardiac administration, intraosseous infusion, intrathecal administration, intravenous infusion, subcutaneous implantation or injection, intramuscular administration, intrarectal administration intravaginal administration, intragastrical administration, intratracheal administration, intrapulmonary administration and intraperitoneal administration. Preparations for parenteral administration include sterile solutions ready for injection, sterile dry soluble products, such as lyophilized powders, ready to be combined with a solvent just prior to use, including sterile suspensions ready for injection, sterile dry insoluble products ready to be combined with a vehicle just prior to use and sterile emulsions. The solutions can be either aqueous or nonaqueous. If administered intravenously, suitable carriers include physiological saline or phosphate buffered saline (PBS), water, and solutions containing thickening and solubilizing agents, such as glucose, polyethylene glycol, and polypropylene glycol and mixtures thereof.

In another embodiment, the present disclosure also contemplates administration of a composition comprising the antibodies of the present disclosure conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, and chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387.

In one embodiment, the composition comprises an antibody or polypeptide conjugated to a cytotoxic agent. Cytotoxic agents can include any agents that are detrimental to cells. An exemplary class of cytotoxic agents that can be conjugated to the antibodies or fragments may include, but are not limited to, paclitaxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs or homologs thereof.

V. Pharmaceutical Compositions

The present disclosure also provides pharmaceutical compositions comprising antibodies or JAK inhibitors described herein, and a pharmaceutically acceptable carrier or excipients. The pharmaceutical compositions may find use, e.g., in the methods, uses, and/or kits of the present disclosure.

Pharmaceutically acceptable carriers or excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. In certain embodiments, a tetravalent antibody described herein is in a liquid pharmaceutical composition. Liquid pharmaceutically administrable compositions can, for example, be prepared by dissolving, dispersing, or otherwise mixing an antibody described herein in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like. Excipients as well as formulations for parenteral and nonparenteral drug delivery are set forth in *Remington, The Science and Practice of Pharmacy* 20th Ed. Mack Publishing (2000).

The pharmaceutical compositions are provided for administration to humans and animals in unit dosage forms, such as sterile parenteral solutions or suspensions containing suitable quantities of a tetravalent antibody described herein. The tetravalent antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody or the antibody derived antigen-binding fragment sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials, or bottles of pints or gallons. Hence, multiple dose form is a multiple of unit-doses which are not segregated in packaging.

The concentration of antibody in the pharmaceutical composition will depend on, e.g., the physicochemical characteristics of the antibody, the dosage schedule, and amount administered as well as other factors known to those of skill in the art.

In some embodiments, the present disclosure provides antibodies and compositions (such as the pharmaceutical compositions described herein) for use in any of the methods described herein, whether in the context of use as a medicament and/or use for manufacture of a medicament, to be administered or formulation for administration with a JAK inhibitor of the present disclosure.

VI. Kits

Certain aspects of the present disclosure are related to kits or articles of manufacture that comprise an anti-PSGL-1 antibody of the present disclosure and/or JAK inhibitor of the present disclosure. Optionally, the kits described herein may contain one or more pharmaceutically acceptable carriers, such as the exemplary carriers described herein. In some embodiments, a kit of the present disclosure includes a pharmaceutical composition of the present disclosure. Kits described herein may find use, e.g., in the methods or uses of the present disclosure.

Kits may optionally provide additional components such as buffers and interpretive information. Normally, the kit comprises a container and a label or package insert(s) on or associated with the container. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

In some embodiments, the kits further include a package insert comprising instructions for administration of the antibody to treat a T-cell mediated disease in combination with a JAK inhibitor, e.g., a T-cell mediated inflammatory disease or cancer. In some embodiments, the kits further include a JAK inhibitor or pharmaceutically acceptable formulation thereof.

The kits of the present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer), or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a tetravalent antibody or polypeptide described herein. The container may further comprise a second pharmaceutically active agent. In some embodiments, a kit may further include any other material or device useful in a treatment (e.g., a transfusion or transplantation), including without limitation one or more containers, tubing, sterilizing agents or equipment, cannulae, syringes, and the like.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Cell Apoptosis Assays with Combined Treatment Using an Anti-PSGL-1 Antibody and JAK Inhibitor The Example presented below describes pre-clinical studies on the use of ruxolitinib, a Janus kinase (JAK) inhibitor, in combination with the anti-PSGL-1 antibody 15A7H to induce activated T cell apoptosis.

Methods

Human T Cell Preparation

T cell stimulation was achieved through Phytohemagglutinin-L (PHA) treatment prior to the apoptosis assays described below. In brief, human blood samples used in the study were obtained from heathy human donors. Peripheral blood mononuclear cells (PBMCs) were freshly isolated from whole blood by Ficoll-Hypaque gradient centrifugation (Ficoll-Paque PLUS, GE Healthcare, Cat #17-1440-03) at 2400 revolutions per minute (rpm) for 15 minutes at room temperature. The buffy coat layer containing mononuclear cells was collected and washed 3 times with phosphate-buffered saline (PBS) to minimize platelet contamination. The harvested PBMCs were used for the generation of activated T cells by incubating with PHA (3 μg/mL, SIGMA, Cat: L2769-10 mg) in RPMI-1640 medium containing 10% fetal bovine serum (FBS) for 2 days, followed by maintenance in medium containing recombinant human Interleukin-2 (5 ng/mL, R&D Systems, Cat. #202-IL-050) for an additional between about 4 and about 6 days.

Cell Apoptosis Assay

Fluorescence-activated cell sorting (FACS) analysis using the Annexin V/propidium iodide (PI) staining method was used to determine the apoptotic rate in drug- and control-treated cells. Briefly, 1-1.5×10$^5$ activated T cells (usually Day 5 to Day 7 post-PHA stimulation) were seeded and cultured with or without the addition of antibody 15A7H and/or JAK inhibitor. Aliquots of antibody 15A7H or ruxolitinib at the indicated concentrations, human IgG4 isotype control at only the highest concentration used for antibody 15A7H, and a cross-linker (CL, a mouse anti-human IgG antibody; Jackson Immuno Research, Cat #209-005-098) at half of the antibody 15A7H concentration, were freshly prepared in complete RPMI-1640 medium (10% FBS, 1% Penicillin/Streptomycin and 2 ng/mL Interleukin-2) and added to test wells at a final volume of 100 μL. Plates were incubated at 37° C. for 48 hours.

Cells were then washed with ice-cold Annexin binding buffer and centrifuged at 300×g for 5 minutes. Cell pellets were re-suspended in ice-cold Annexin binding buffer, and Annexin-V-FITC, along with PI (Strong Biotech, AVK250) were added. The staining procedures were carried out using Annexin-V FITC Apoptosis Detection Kit (Strong Biotech, AVK250), according to the manufacturer's instructions.

Samples were run on a flow cytometer (BD LSR scanner; BD Biosciences, San Diego), and cell viability and apoptosis were calculated using a quadrant on the Annexin-V-FITC/PI histogram. Living cells were identified as those negatively stained for both fluorescence dyes, early apoptotic cells were identified as those only Annexin-V-FITC-positive, necrotic cells were identified as those only PI-positive, and late apoptotic cells were identified as those positively stained for both fluorescence dyes. Annexin-V-positive cells, PI-positive cells, and Annexin-V- and PI-positive cells were counted as apoptotic cells.

Fixed-Ratio Combination Cytotoxicity Assays

Activated T cells were seeded in 96-well plates at 1-1.5×10$^5$ cells/mL and were treated with ruxolitinib and antibody 15A7H alone, or in combination at fixed concentration ratios. For the combination of ruxolitinib and antibody 15A7H, fixed ratios at 3.3:1 and 1.1:1 were tested on T cells from four donors. In addition, a fixed ratio of ruxolitinib and antibody 15A7H of 0.37:1 was tested on T cells from two donors.

Cell apoptosis was measured using an Annexin-V FITC Apoptosis Detection Kit (Strong Biotech, AVK250), according to the manufacturer's instructions. The combinatorial drug effect was assessed by calculating the combination index (CI) using the Calcusyn software (Version 2.0, Biosoft) based on the Chou-Talalay method (see, e.g., Chou T C, (2010) Cancer Res., 70:440-446; and Bijnsdorp I V. et al., (2011) Methods Mol Biol., 731:421-434), where CI<1 indicates synergy, CI=1 indicates additivity, and CI>1 indicates antagonism.

Reagents

JAK inhibitor ruxolitinib ("RUXO") was obtained from LC Laboratories (Cat. #R-6688), and was dissolved in dimethylsulfoxide (DMSO) according to the manufacturer's instructions. Ruxolitinib is part of the first-generation JAK inhibitors that were found to inhibit more than one JAK; ruxolitinib inhibits JAK1 and JAK2.

Results

Antibody 15A7H at concentrations of 0.03 μg/mL, 0.3 μg/mL, and 3 μg/mL, and ruxolitinib at concentrations of 10 μM, 3.3 μM, 1.1 μM, 0.367 μM, and 0.122 μM, alone or in combination, were initially tested in activated T cells derived from PBMCs of three donors to determine a preliminary combination effect.

Figure 1B:
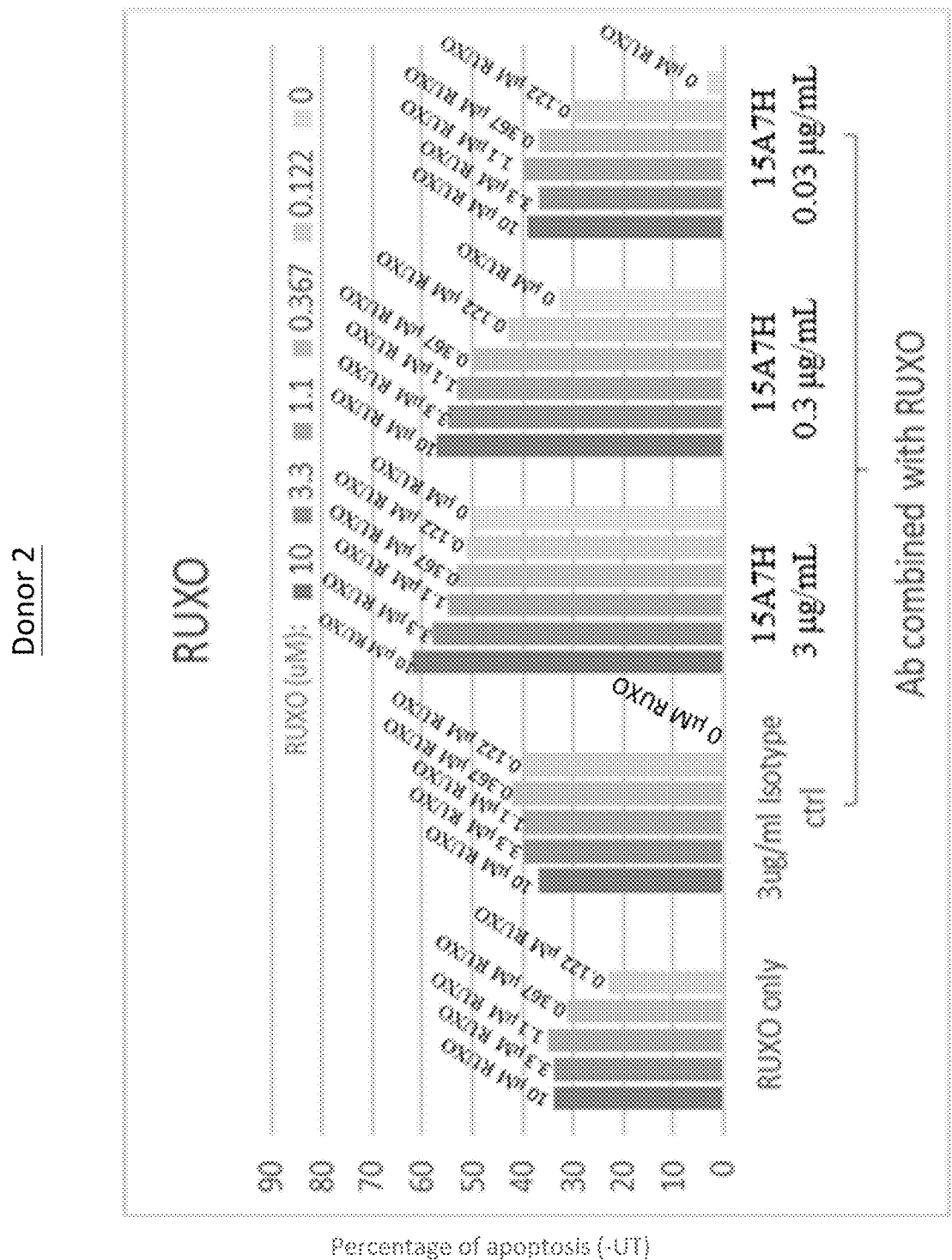
Figure 1C:
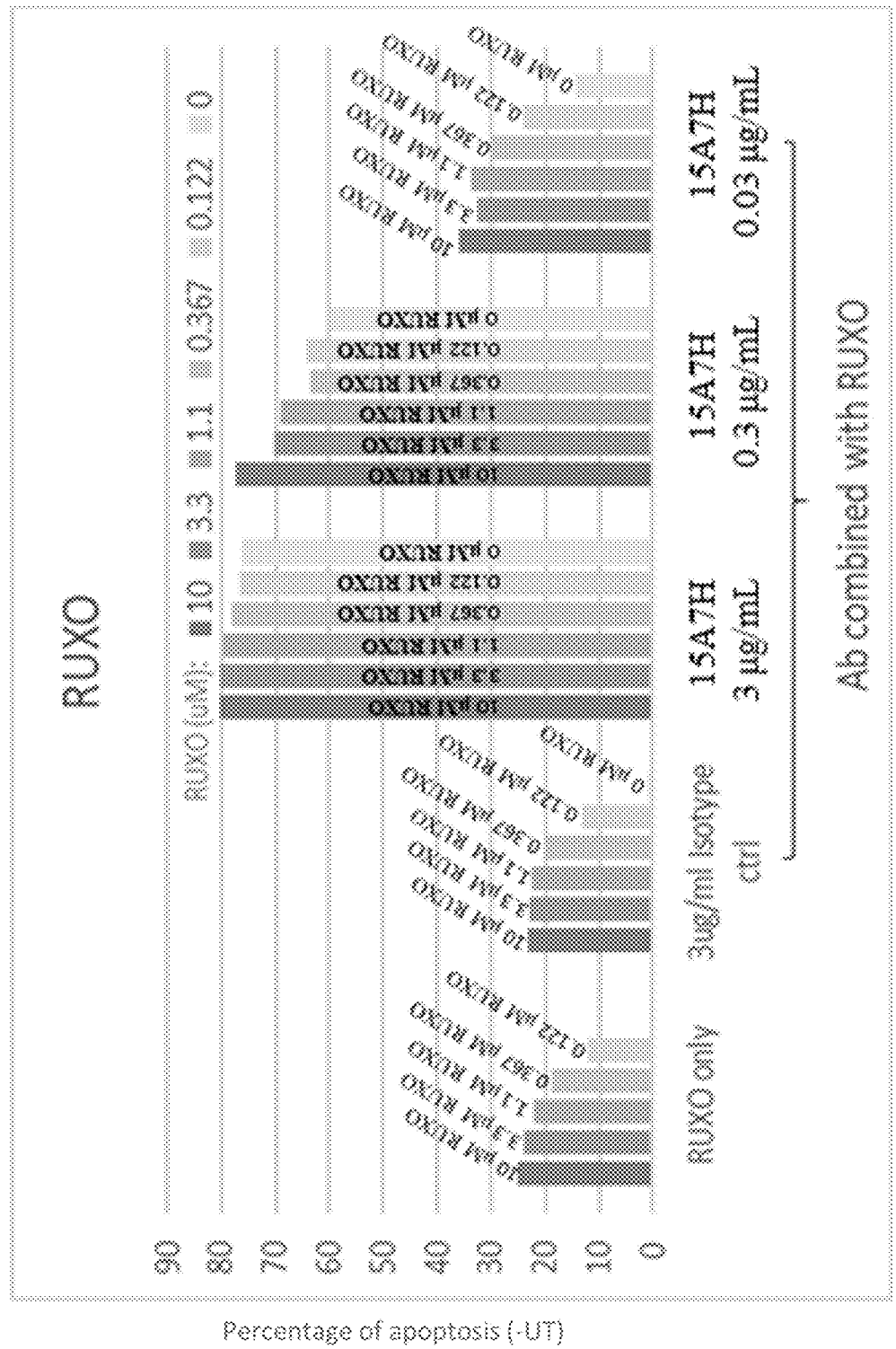

As shown in FIGS. 1A-1C, antibody 15A7H alone at a concentration of 3 μg/mL and in the presence of antibody cross-linker triggered an optimal apoptosis-induction in activated T cells after 48 hours of treatment. Sub-optimal antibody 15A7H concentrations of 0.03 μg/mL and 0.3 μg/mL generally resulted in minimal to medium apoptosis-induction in the treated cells, depending on the donor. Treatment of T cells with ruxolitinib alone at concentrations in the range of 0.122-10 μM for 48 hours resulted in minimal or no increases in apoptosis over background levels. However, the combination of ruxolitinib with antibody 15A7H, in particular at sub-optimal antibody concentrations of 0.03 μg/mL and 0.3 μg/mL, resulted in increases in the level of cell apoptosis as compared to cells treated with antibody 15A7H alone at the same concentrations, or as compared to cells treated with ruxolitinib and isotype control antibody.

To further verify the combinatorial effect of antibody 15A7H and ruxolitinib on apoptosis induction in activated T cells, the combinatorial effect was evaluated using Chou-Talalay median effect analysis using fixed ratios of antibody 15A7H and ruxolitinib (Chou T C. Cancer Res. 2010; 70:440-446). Cells were treated with each drug alone and in combination, and cell apoptosis was measured using an Annexin-V FITC Apoptosis Detection Kit (Strong Biotech, AVK250). Results were expressed as apoptosis fractions (fraction affected), based on the measured fluorescence counts of treated samples, compared with that of untreated controls. Seven diagonals representing various dose-effect curves with fixed drug ratios were used to measure the combination indexes (CI) for each of the combinations with Calcusyn software (Biosoft). The combinatorial effect was defined as "synergistic", "additive" or "antagonistic" when CI was <1, 1 and >1, respectively.

Figure 2:
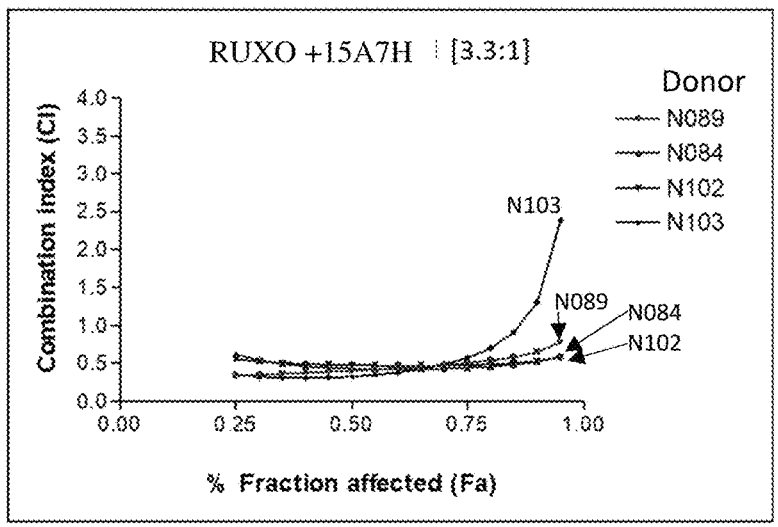
FIG. 2 provides results of experiments testing the combinatorial effect of ruxolitinib ("RUXO") in combination with anti-PSGL-1 antibody 15A7H on activated T cell apoptosis, assessed using Chou-Talalay median effect analysis as described in Example 1 herein. Ruxolitinib and antibody 15A7H were tested at the indicated fixed ratios (3.3:1, 1.1:1, and 0.37:1) for their effect on activated T cell apoptosis in cells derived from the indicated donors (N089, N084, N102, and N103). The x-axis shows the observed apoptosis fractions as compared to untreated control cells, and the y-axis shows the corresponding combination index (CI). Combinatorial effects were defined as "synergistic", "additive" or "antagonistic" when the CI was <1, 1 and >1, respectively.
Figure 2:
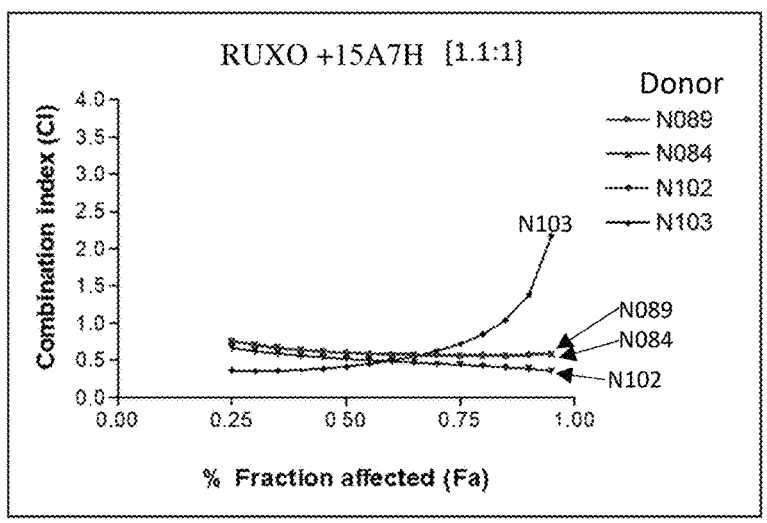
Figure 2:
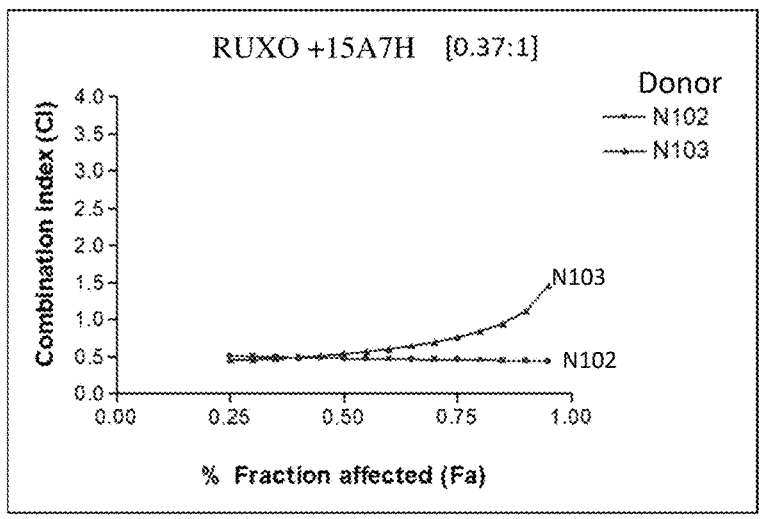

As shown in FIG. 2, the fixed-ratio combination apoptosis assays confirmed that antibody 15A7H synergized with ruxolitinib at the ratios of 3.3:1, 1.1:1, and 0.37:1, since most of the CI values calculated for the 25% to 75% fractions of donor T cells affected remained below 0.9.

For drug combination assessments, CI values ranging from 0.1-0.3 are considered to indicate strong synergism, 0.3-0.7 indicate synergism, and 0.7-0.85 indicate moderate synergism. Table 1 shows CI indexes at $EC_{50}$ levels across all drug ratios and donors tested. The CI indexes for antibody 15A7H in combination with ruxolitinib were within the range of 0.3-0.6, indicating a synergism of antibody 15A7H in combination with ruxolitinib (see, e.g., Karagianni F. et al., (2021) PLoS ONE, 16(3): e0248298).

TABLE 1

CI indexes of the combination of antibody 15A7H and ruxolitinib ("RUXO") at $EC_{50}$ levels across all ratios and donors tested.

Drug Combination: RUXO + 15A7H; Ratio: [3.3:1]

| | Single Treatment | | Combination Treatment | | | | |
|---|---|---|---|---|---|---|---|
| Donor | $EC50_{RUXO}$ [μM] | $EC50_{15A7H}$ [μg/ml] | $EC50_{RUXO}$ [μM] | $EC50_{15A7H}$ [μg/ml] | $DRI_{RUXO}$ | $DRI_{15A7H}$ | CI |
| N089 | 1.9959 | 0.8654 | 0.4788 | 0.1436 | 4.1685 | 6.0249 | 0.4059 |
| N084 | 4.2210 | 0.3275 | 0.3727 | 0.1118 | 11.3242 | 2.9286 | 0.4298 |
| N102 | 10.0995 | 0.9589 | 1.1519 | 0.3456 | 8.7676 | 2.7749 | 0.4744 |
| N103 | 9.1683 | 1.4030 | 1.0086 | 0.3026 | 9.0902 | 4.6368 | 0.3257 |

Drug Combination: RUXO + 15A7H; Ratio: [1.1:1]

| | Single Treatment | | Combination Treatment | | | | |
|---|---|---|---|---|---|---|---|
| Donor | $EC50_{RUXO}$ [μM] | $EC50_{15A7H}$ [μg/ml] | $EC50_{RUXO}$ [μM] | $EC50_{15A7H}$ [μg/ml] | $DRI_{RUXO}$ | $DRI_{15A7H}$ | CI |
| N089 | 2.3633 | 0.8155 | 0.3938 | 0.3544 | 6.0012 | 2.3009 | 0.6012 |
| N084 | 4.2210 | 0.3275 | 0.2011 | 0.1810 | 20.9884 | 1.8093 | 0.6003 |
| N102 | 10.0995 | 0.9589 | 0.4993 | 0.4494 | 20.2269 | 2.1339 | 0.5181 |
| N103 | 9.1683 | 1.4030 | 0.5537 | 0.4984 | 16.5574 | 2.8153 | 0.4156 |

Drug Combination: RUXO + 15A7H; Ratio: [0.37:1]

| | Single Treatment | | Combination Treatment | | | | |
|---|---|---|---|---|---|---|---|
| Donor | $EC50_{RUXO}$ [uM] | $EC50_{15A7H}$ [ug/ml] | $EC50_{RUXO}$ [uM] | $EC50_{15A7H}$ [ug/ml] | $DRI_{RUXO}$ | $DRI_{15A7H}$ | CI |
| N102 | 10.0995 | 0.9589 | 0.1648 | 0.4450 | 61.2797 | 2.1549 | 0.4804 |
| N103 | 9.1683 | 1.4030 | 0.2664 | 0.7192 | 34.4195 | 1.9508 | 0.5417 |

DRI: The Dose-Reduction Index (DRI) is a measure of the fold the dose of each drug in a synergistic combination may be reduced at a given effect level, compared with the doses of each drug alone.

Example 2: Cell Apoptosis Assays Using Combined Treatment with an Anti-PSGL-1 Antibody and an mTOR Inhibitor The Example presented below describes an in vitro cytotoxicity study using rapamycin, an mTOR inhibitor, alone or in combination with the anti-PSGL-1 antibody 15A7H. The potent immunosuppressive drug rapamycin interferes with signal transduction pathways required for T cell activation and growth. It has been clinically approved for prophylaxis of organ rejection and some cancer indications.

Methods
Reagents

Rapamycin was obtained from AdooQ Bioscience (Cat. #A10782-5) and dissolved in dimethylsulfoxide (DMSO) according to the manufacturer's instructions.

Human T Cell Preparation

PBMCs were obtained from peripheral blood of healthy donors. Isolation was performed by density centrifugation of blood on Ficoll (GE Healthcare, Cat #17-1440-03). The harvested PBMCs were used for the generation of activated T cells by incubating with PHA (3 μg/mL, SIGMA, Cat: L2769-10 mg) in RPMI-1640 medium (10% FBS, 1% Penicillin/Streptomycin and 2-Mercaptoethanol) for 2 days, followed by maintenance in medium containing recombinant human Interleukin-2 (5 ng/mL, R&D Systems, Cat. #202-IL-050) for an additional between about 4~6 days.

Cell Apoptosis Assay

Rapamycin is a macrolide exhibiting potent immunosuppressive activity. To evaluate the drug combination effect, 1-1.5×10⁵ activated T cells were plated in 96 well and treated with 15A7H (containing cross-linker, mouse anti-human IgG antibody, Jackson, Cat #209-005-098) and rapamycin alone or in combination at the indicated concentrations for 48 hr. The cytotoxicity was assessed by the Annexin V/propidium iodide (PI) staining method to determine the apoptotic rate in drug-treated cells.

Results

Figure 3A:
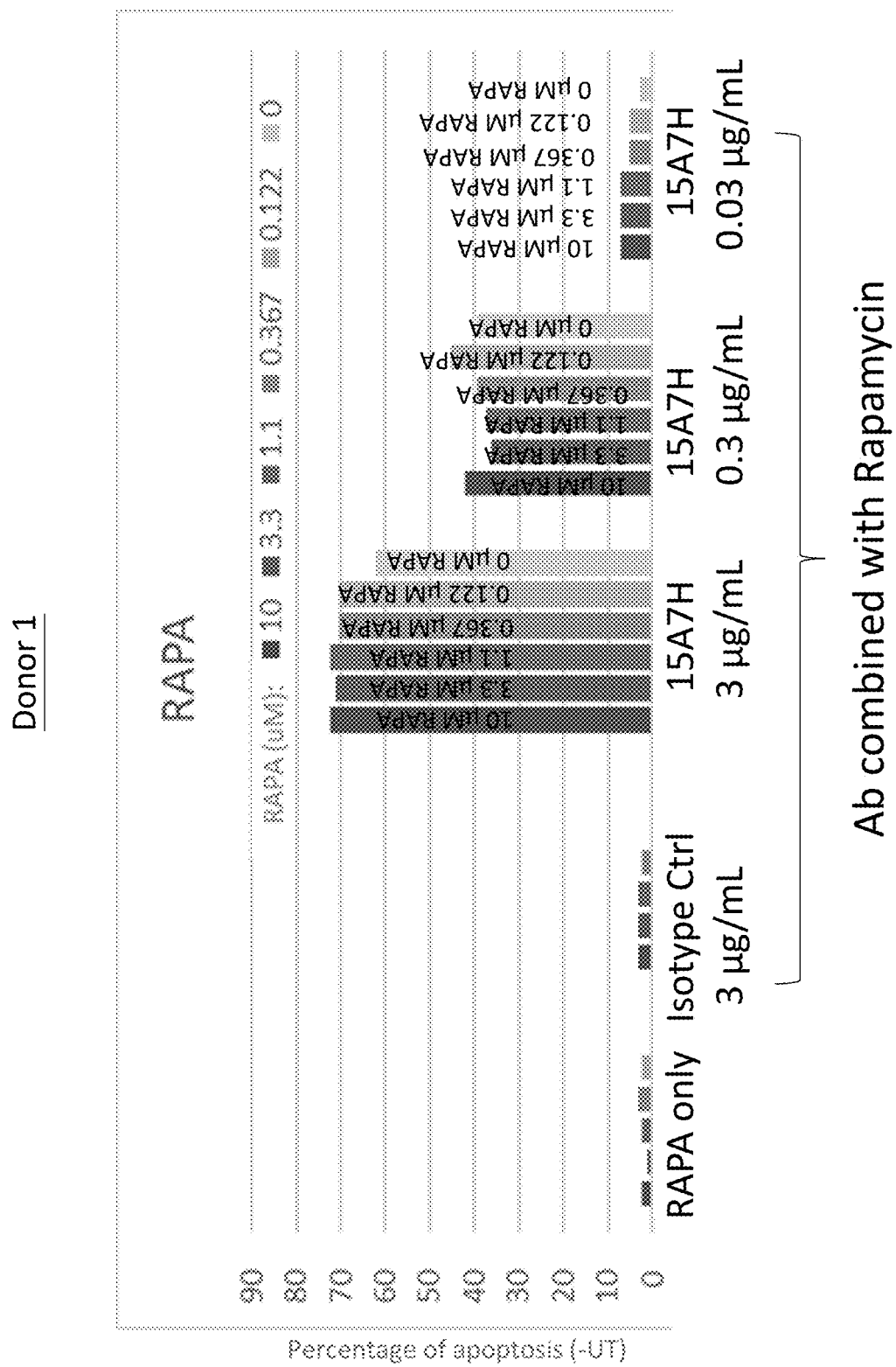
FIGS. 3A-3C provide results of T cell apoptosis assays that tested the combination of rapamycin ("RAPA") in combination with anti-PSGL-1 antibody 15A7H. Rapamycin and antibody 15A7H were tested alone or in combination at the indicated concentrations (RAPA: 10 μM, 3.3 μM, 1.1 μM, 0.367 μM, and 0.122 μM; antibody 15A7H: 0.03 μg/mL, 0.3 μg/mL, and 3 μg/mL) in activated T cells derived from peripheral blood mononuclear cells (PBMCs) from three donors (Donor 1, FIG. 3A; Donor 2.
Figure 3B:
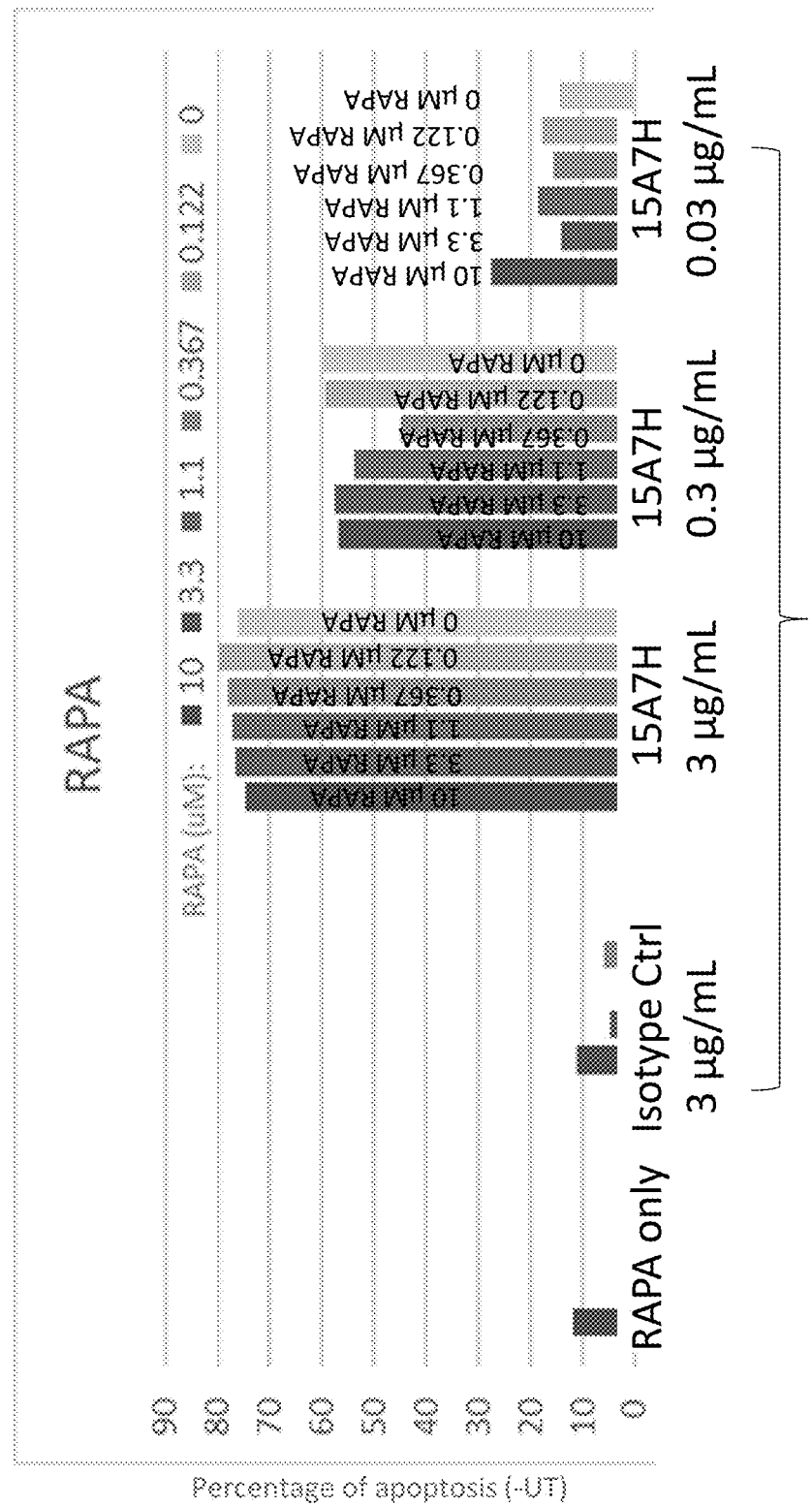
Figure 3C:
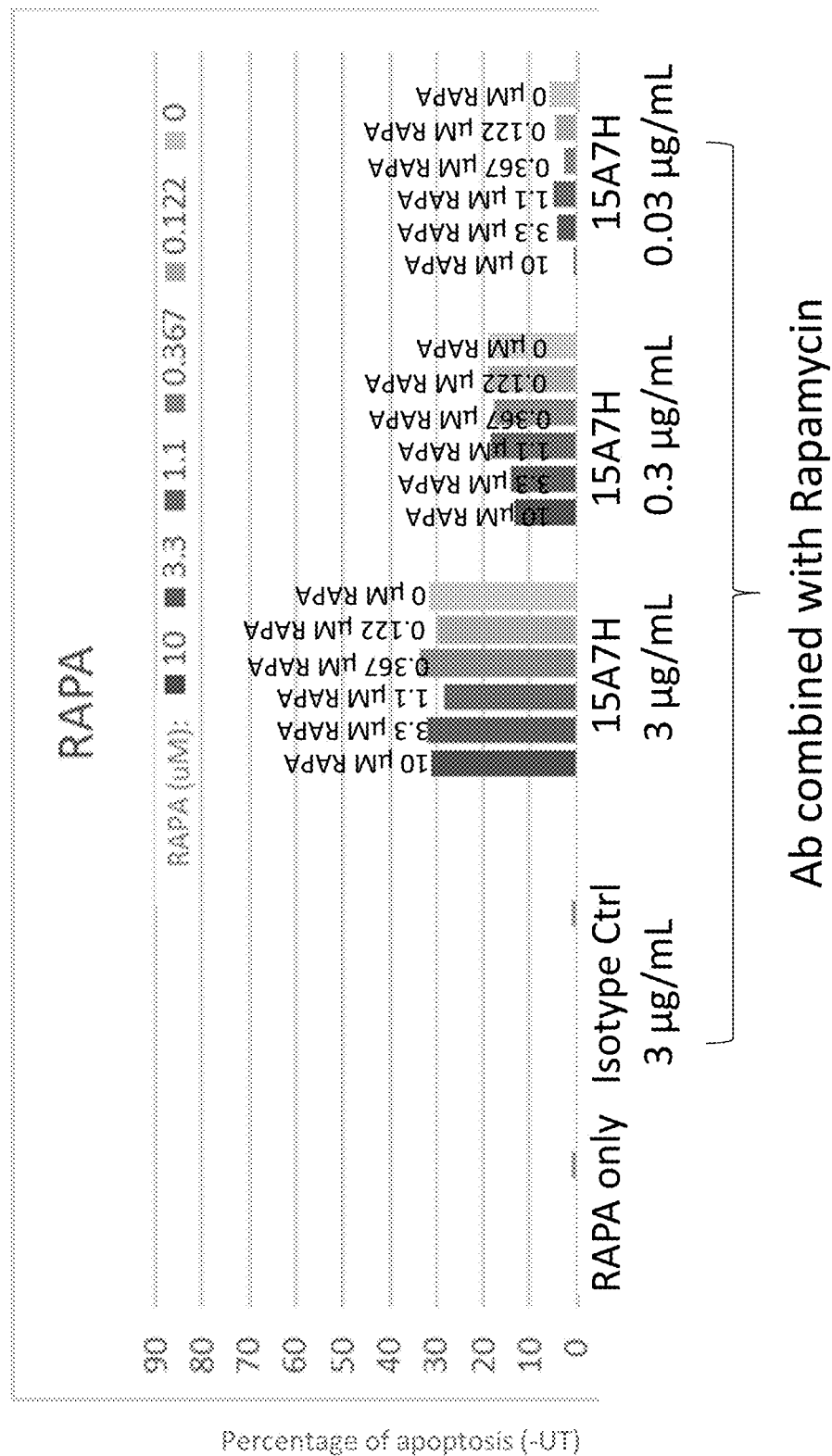

Treatment of the cells with rapamycin alone at 0.122 to 10 μM range after 48 hr did not result in any significant level of cell apoptosis (FIGS. 3A-3C). The combination treatment of rapamycin and 15A7H did not increase the level of apoptotic cells, compared to the cells treated with 15A7H alone at the same dose level. These data suggested that the treatment of 15A7H plus rapamycin did not have any additive effect on activated T cells.

Example 3: Fixed-Ratio Combination Cytotoxicity Assays Using Ruxolitinib and Anti-PSGL-1 Antibodies The Example presented below describes that in addition to 15A7H, other anti-PSGL-1 antibodies with cytotoxicity function can synergize with ruxolitinib to induce activated T cell apoptosis.

Methods
Reagents

JAK inhibitor ruxolitinib ("RUXO") was obtained from LC Laboratories (Cat. #R-6688) and dissolved in dimethylsulfoxide (DMSO) according to the manufacturer's instructions.

Human T Cell Preparation

PBMCs were obtained from peripheral blood of healthy donors. Isolation was performed by density centrifugation of blood on Ficoll (GE Healthcare, Cat #17-1440-03). The harvested PBMCs were used for the generation of activated T cells by incubating with PHA (3 µg/mL, SIGMA, Cat: L2769-10 mg) in RPMI-1640 medium (10% FBS, 1% Penicillin/Streptomycin and 2-Mercaptoethanol) for 2 days, followed by maintenance in medium containing recombinant human Interleukin-2 (5 ng/mL, R&D Systems, Cat. #202-IL-050) for an additional between about 4~6 days.

Fixed-Ratio Combination Cytotoxicity Assays

In addition to 15A7H, anti-PSGL-1 antibodies LH10, c43B6 and h9F9 were tested for the ability to induce cell death in activated T cells. The purpose of this study was to determine whether apoptosis inducing anti-PSGL-1 antibodies plus ruxolitinib would result in a better cytotoxic effect on activated T cells. The combinatorial effect was evaluated using Chou-Talalay median effect analysis using fixed ratios of antibodies and ruxolitinib in cytotoxicity assays. Activated T cells were seeded in 96-well plates at $1-1.5 \times 10^5$ cells/mL and treated with ruxolitinib and anti-PSGL1 antibodies alone, or in combination at fixed 3.3:1, 1.1:1 and 0.37:1 concentration ratio for 48 hr. The anti-PSGL-1 antibodies LH10, c43B6, and h9F9 were tested in 3-fold titration from 0.004 µg/mL to 3 µg/mL (containing cross-linker, mouse anti-human IgG antibody Jackson, Cat #209-005-098) at half of anti-PSGL-1 antibodies concentration) and ruxolitinib in 3-fold titration from 0.0015 µM to 10 µM alone or in combination, were tested in these assays.

Results

Cell apoptosis was determined as described in Example 1, and the combinatorial drug effect combination indexes (CI) were analyzed using CalcuSyn (Biosoft, Ferguson, MO, USA), which allows automated simulation of synergism or antagonism, where CI<1 indicates synergy, CI=1 indicates additivity, and CI>1 indicates antagonism. As shown in FIG. 4A (LH10), 4B (c43B6) and (h9F9), the combination of anti-PSGL-1 antibodies which had cytotoxicity ability in activated T cells, LH10, c43B6 and h9F9, synergized with ruxolitinib at the ratios of 3.3:1, 1.1:1, and 0.37:1, since most of the CI values calculated for the 35% to 85% fractions of donor T cells affected remained below 0.9.

Example 4: Fixed-Ratio Combination Cytotoxicity Assays Using Tofacitinib and Anti-PSGL-1 Antibodies The Example presented below describes studies on the use of tofacitinib, a Janus kinase (JAK) 1/3 inhibitor, in combination with the anti-PSGL-1 antibody 15A7H and LH10 to induce activated T cell apoptosis.

Methods
Reagents

JAK inhibitor tofacitinib ("TOFA") was obtained from AdooQ Bioscience (A10241-10) and dissolved in dimethylsulfoxide (DMSO) according to the manufacturer's instructions.

Human T Cell Preparation

PBMC were obtained from peripheral blood of healthy donors. Isolation was performed by density centrifugation of blood on Ficoll (GE Healthcare, Cat #17-1440-03). The harvested PBMCs were used for the generation of activated T cells by incubating with PHA (3 µg/mL, SIGMA, Cat: L2769-10 mg) in RPMI-1640 medium (10% FBS, 1% Penicillin/Streptomycin and 2-Mercaptoethanol) for 2 days, followed by maintenance in medium containing recombinant human Interleukin-2 (5 ng/mL, R&D Systems, Cat. #202-IL-050) for an additional between about 4~6 days.

Fixed-Ratio Combination Cytotoxicity Assays

Tofacitinib, a first-generation jakinib that inhibits JAK3, JAK1, and to a lesser degree JAK2, is the first JAK inhibitor developed for the treatment of inflammatory diseases including rheumatoid arthritis (RA), psoriatic arthritis and active ulcerative colitis. In this experiment, the cytotoxicity assay in activated T cells treated with tofacitinib (at concentration from 0.01 to 3 µM) and anti-PSGL-1 antibodies, 15A7H or LH10 (at concentration from 0.01 to 3 µg/mL) at a fixed ratio of 1:1 combination was performed to evaluate the combination effect. Briefly, $1-1.5 \times 10^5$ activated T cells were seeded and treated with antibody 15A7H or LH10 plus tofacitinib. Aliquots of antibodies or tofacitinib at the indicated concentrations and a cross-linker (mouse anti-human IgG antibody; Jackson, Cat #209-005-098) at half of the anti-PSGL-1 antibodies concentration, were freshly prepared in complete RPMI-1640 medium (10% PBS, 1% Penicillin/Streptomycin and 2 ng/mL Interleukin-2) and added to test wells at a final volume of 100 µL. Plates were incubated at 37° C. for 48 hours. As described in Example 1, the combinatorial effect was assessed using the Calcusyn software to calculate the combination index (CI) based on the apoptosis assay results of mono- and combined treatment. Cell apoptosis was measured using an Annexin-V FITC Apoptosis Detection Kit (Strong Biotech, AVK250), according to the manufacturer's instructions.

Results

Figure 5:
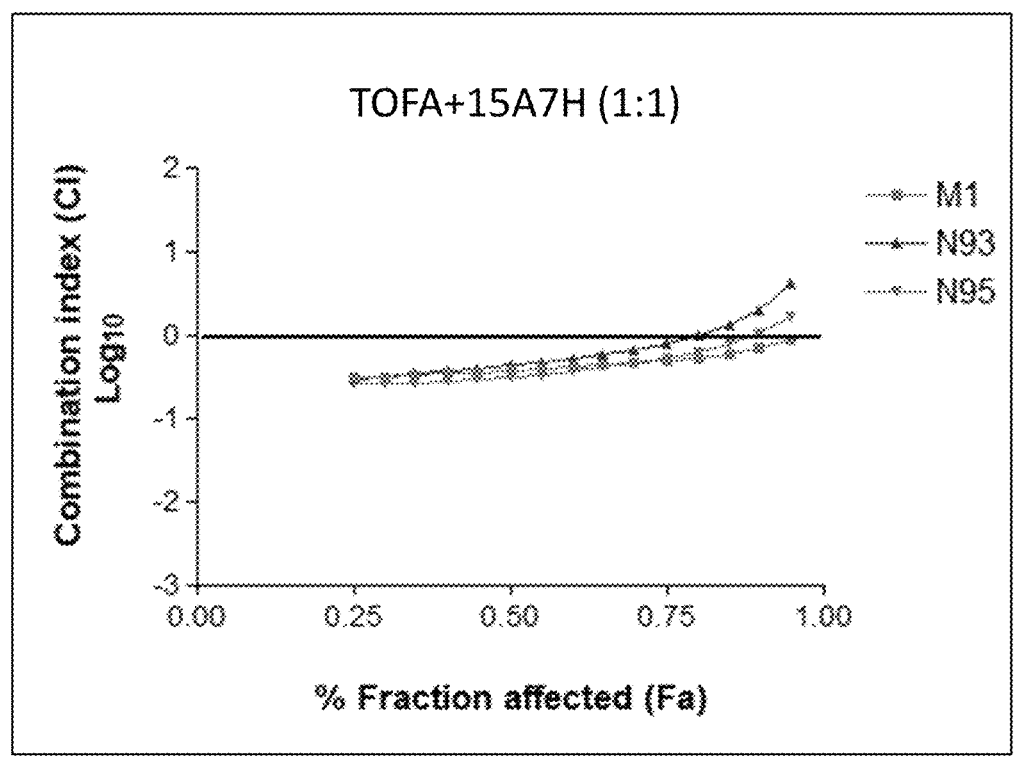
FIG. 5 provides results of experiments testing the combinatorial effect of tofacitinib ("TOFA") in combination with anti-PSGL-1 antibodies 15A7H or LH10 on activated T cell apoptosis, assessed using Chou-Talalay median effect analysis as described in Example 4 herein. Tofacitinib and antibody 15A7H or LH10 were tested at the indicated fixed ratio of 1:1 for their effect on activated T cell apoptosis in cells derived from the indicated donors (M1, N93, and N95). The x-axis shows the observed apoptosis fractions as compared to untreated control cells, and the y-axis shows the corresponding $Log_{10}$ combination index (CI). Combinatorial effects were defined as "synergistic", "additive" or "antagonistic" when the CI was <1, 1 and >1, respectively.
Figure 5:
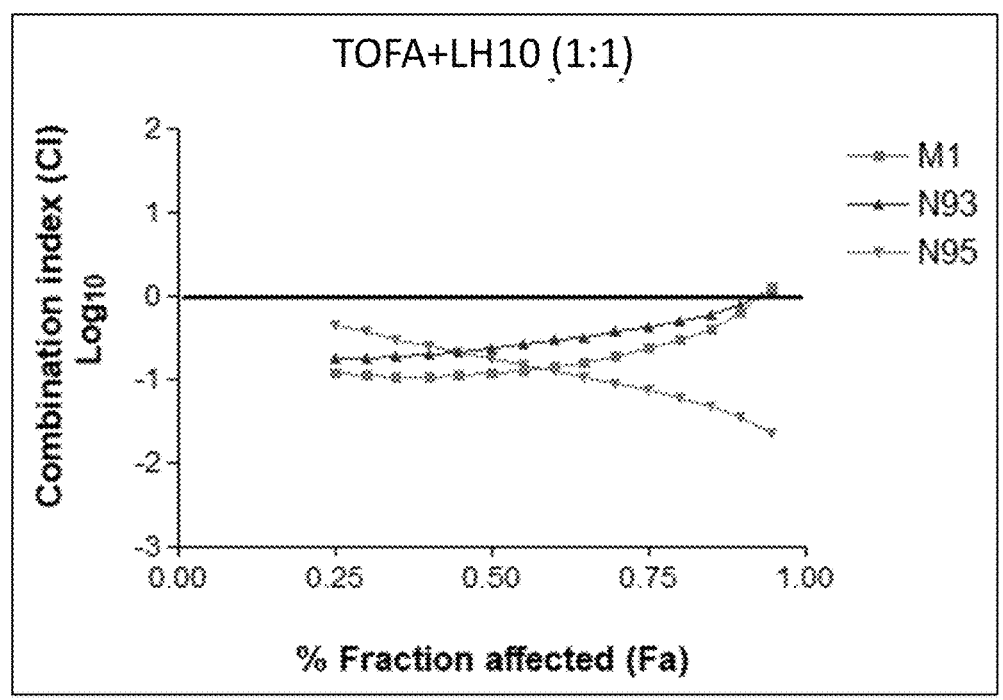

As shown in FIG. 5, the experimental results indicate that the combination of Tofacitinib plus 15A7H or LH10 developed with remarkable synergistic efficacy, since most of the CI values calculated for the 25% to 75% fractions of donor T cells affected remained below 0.5.

Example 5: Ruxolitinib and Anti-PSGL-1 Antibody Combination Treatment in a Xenogeneic Graft-Versus-Host Disease (GvHD) Mouse Model The Example presented below describes studies on the use of Ruxolitinib in combination with the anti-PS GL-1 antibody 15A7H to improve the survival of the mice with human PBMC engraftment resulted in xenogenic GvHD.

Methods
Reagents

JAK inhibitor Ruxolitinib ("RUXO") was obtained from LC Laboratories (Cat. #R-6688) and dissolved in dimethyl sulfoxide (DMSO) according to the manufacturer's instructions and formulated in 0.5% methylcellulose vehicle for oral gavage administration.

Human PBMC Preparation

PBMCs were obtained from peripheral blood of healthy donors. Isolation was performed by density centrifugation of blood on Ficoll (GE Healthcare, Cat #17-1440-03). The harvested PBMCs were washed and aliquoted in PBS.

Mouse Experiments 8-9 weeks old female Advanced Severe Immuno-Deficiency (ASID) mice (NOD.Cg-Prkdc$^{scid}$Il2rg$^{tm1Wjl}$/YckNarl; NLAC NARLabs Taiwan) received a total body irradiation dose of 2.0 Gy and were engrafted with $3 \times 10^6$ human PBMCs by tail vein injection at 24 hours post irradiation. The mice were kept under pathogen-free conditions and reared under standardized methods as temperature set at 22±1° C. with a 12-hour daylight/dark cycle and full access to food and water. Experimental animals were randomly divided into treatment groups after receiving a minimum of 3 days of acclimatization to the environment.

Figure 6:
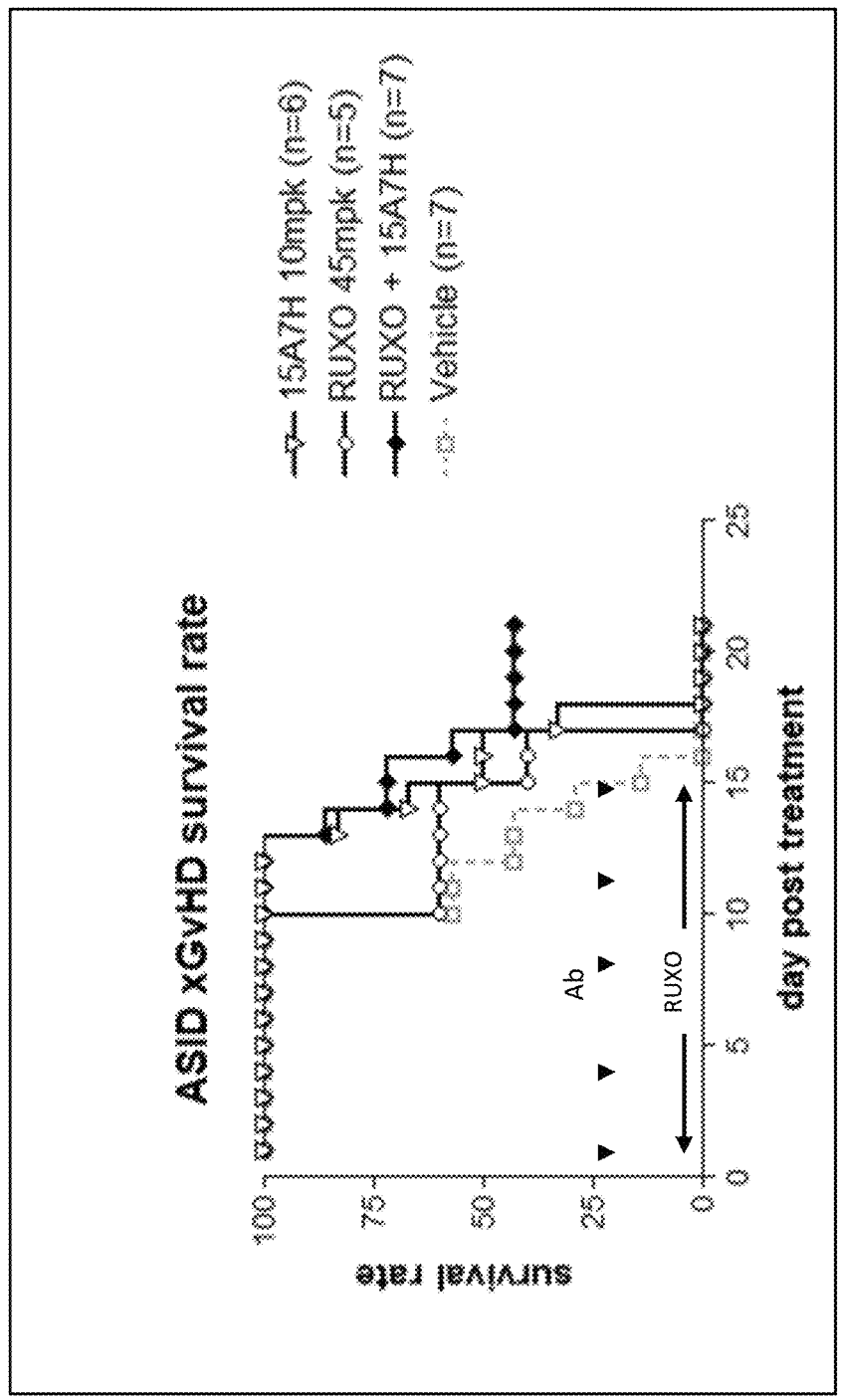
FIG. 6 provides results of experiments testing the effects of ruxolitinib, the anti-PSGL-1 antibody 15A7H, or the combination of both in a xenogeneic mouse model of graft-versus-host disease (GvHD). Advanced Severe Immuno-Deficiency (ASID) mice were irradiated and engrafted with human PBMCs to induce xenogeneic GvHD. Post 72 hours of human PBMC engraftment, the treatments were initiated (assigned as Day 1). Ruxolitinib at 45 mg/kg (45 mpk) or vehicle was orally administered twice daily for 15 days, as well as anti-PSGL-1 15A7H antibody at 10 mg/kg (10 mpk) or vehicle was intravenously administered every 3 to 4 days for total 5 doses. Mice were assessed for survival daily. Survival over time post-treatment for all 4 treatment groups is shown (n=5~7 per group). The group of combination treatment showed the best survival rate.

Xenogeneic GvHD (xGvHD) was induced in ASID mice receiving $3 \times 10^6$ human PBMCs (n=5-7 per group). Post 72 hours of human PBMC engraftment, ruxolitinib at 45 mg/kg or vehicle was orally administered twice daily for 15 days, as well as anti-PSGL-1 15A7H antibody at 10 mg/kg or vehicle was intravenously administered every 3 to 4 days for total 5 doses. Mice were assessed for survival daily. The time of the treatment initiated was designated as Day 1.
Results As shown in FIG. 6, ruxolitinib and anti-PSGL-1 antibody 15A7H alone or in combination treatment ameliorated xenogeneic GVHD induced by human lymphocytes. Moreover, whereas no animals from the vehicle-treated group (dashed line with open square) survived past day 16, mice receiving treatment of ruxolitinib (solid line with open circle) or antibody 15A7H (solid line with open triangle) alone showed a delayed mortality, yet none survived past day 18. The group of combination treatment has the best survival rate, as 43% (3 of 7) of mice stayed alive until the end of the experiment (Day 21).

Example 6: Clinical Study of an Anti-PSGL-1 Antibody in Patients with Steroid-Refractory Acute Graft-Versus-Host Disease (SR-aGVHD) or Treatment-Refractory Acute Graft-Versus-Host Disease (TR-aGVHD)

The Example presented below describes a Phase 1, open-label study of anti-PSGL-1 antibody 15A7H in patients with steroid-refractory acute graft-versus-host disease (SR-aGVHD) or treatment-refractory acute graft-versus-host disease (TR-aGVHD).
Study Design Anti-PSGL-1 antibody 15A7H was tested in patients with SR-aGVHD or TR-aGVHD using multiple doses of antibody. Study participants were assigned to receive a first dose of antibody 15A7H at 6 mg/kg, followed by weekly doses of antibody 15A7H at 4 mg/kg for 3 weeks (6-4-4-4 regimen).

This study included patients with SR-aGVHD without any prior systemic treatment other than corticosteroids, as well as patients with TR-aGVHD with one prior systemic treatment for aGVHD, including JAK inhibitors, in addition to corticosteroids. Participants treated with antibody 15A7H in combination with an additional systemic treatment were also included in the study.
Results An analysis of efficacy was conducted after enrollment of 24 participants in this study to determine the likelihood of reaching pre-established futility criteria. Of 24 participants, 12 participants were categorized as steroid refractory (SR) and 12 participants as treatment refractory (TR).

Improved clinical responses were observed in participants with TR (8/12=67% Overall Response) as compared to participants with SR (4/12=33% Overall Response). This finding was unexpected because patients that have received prior systemic therapy are believed to have more severe or progressive disease. Further analysis showed that clinical responses were improved in participants receiving concomitant JAK-inhibition therapy in addition to antibody 15A7H.

The observation of improved outcomes in patients treated with antibody 15A7H in combination with JAK-inhibition in patients with T cell-mediated disease is supported by pre-clinical experiments, e.g., as described in Example 1 herein, showing a synergistic response when antibody 15A7H was combined with JAK-inhibitors such as ruxolitinib.

Although the foregoing embodiments have been described in some detail by way of illustration and example for purposes of clarity of understanding, the descriptions and examples should not be construed as limiting the scope of the present disclosure.

What is claimed is:

1. A method of treating a T-cell mediated inflammatory disease, the method comprising administering to a subject in need thereof a therapeutically effective amount of an antibody that specifically binds to human PSGL-1 in combination with a Janus kinase (JAK) inhibitor; wherein the antibody that specifically binds to human PSGL-1 comprises a heavy chain comprising a heavy chain variable (VH) domain and a light chain comprising a light chain variable (VL) domain, wherein the VH domain comprises a CDR-H1 comprising the amino acid sequence SFGMH (SEQ ID NO:8), a CDR-H2 comprising the amino acid sequence YINGGSSTIFYANAVKG (SEQ ID NO:9), and a CDR-H3 comprising the amino acid sequence YASYGGGAMDY (SEQ ID NO:10), and wherein the VL domain comprises a CDR-L1 comprising the amino acid sequence RSSQ-SIVHNDGNTYFE (SEQ ID NO: 5), a CDR-L2 comprising the amino acid sequence KVSNRFS (SEQ ID NO:6), and a CDR-L3 comprising the amino acid sequence FQGSYVPLT (SEQ ID NO:7).

2. The method of claim 1, wherein the JAK inhibitor inhibits JAK1 and/or JAK2.

3. The method of claim 1, wherein the JAK inhibitor inhibits JAK1 and/or JAK3.

4. The method of claim 1, wherein the JAK inhibitor is ruxolitinib or tofacitinib.

5. The method of claim 1, wherein the antibody is a humanized antibody.

6. The method of claim 1, wherein the VH domain comprises the amino acid sequence of SEQ ID NO:4, and wherein the VL domain comprises the amino acid sequence of SEQ ID NO:3.

7. The method of claim 1, wherein the antibody that specifically binds to human PSGL-1 comprises a heavy chain and a light chain, and wherein the heavy chain further comprises an antibody constant domain.

8. The method of claim 7, wherein the constant domain is a human IgG4 constant domain.

9. The method of claim 8, wherein the constant domain is a human IgG4 constant domain comprising an S228P amino acid substitution at position 228, wherein the numbering is according to EU numbering.

10. The method of claim 1, wherein the antibody that specifically binds to human PSGL-1 comprises a heavy chain and a light chain, and wherein the light chain is a human kappa light chain.

11. The method of claim 1, wherein the antibody that specifically binds to human PSGL-1 comprises a heavy chain and a light chain, wherein the heavy chain comprises the amino acid sequence of SEQ ID NO:2, and wherein the light chain comprises the amino acid sequence of SEQ ID NO:1.

12. The method of claim 1, wherein the antibody that specifically binds to human PSGL-1 comprises the amino acid sequence of SEQ ID NO:23.

13. The method of claim 1, wherein the T-cell mediated inflammatory disease is graft-versus-host disease (GVHD) or transplantation rejection.

14. The method of claim 13, wherein the T-cell mediated inflammatory disease is acute GVHD, steroid-refractory acute GVHD (SR-aGVHD), treatment-refractory acute GVHD (TR-aGVHD), or chronic GVHD.

15. The method of claim 1, wherein the T-cell mediated inflammatory disease is selected from the group consisting of: a skin disorder, multiple sclerosis, rheumatoid arthritis, juvenile arthritis, type I diabetes, lupus, inflammatory bowel disease, Crohn's disease, myasthenia gravis, immunoglobulin nephropathies, myocarditis, psoriasis, ankylosing spondylitis, arthritis, diabetes mellitus, systemic lupus erythematosus, dermatitis, Sjogren's Syndrome, ulcerative colitis, asthma, allergic asthma, scleroderma, autoimmune uveitis, Stevens-Johnson syndrome, vitiligo, alopecia areata, cytokine release syndrome, hidradenitis suppurativa, sarcoidosis, primary biliary cirrhosis, uveitis posterior, allergies, and autoimmune thyroid disorder.

16. The method of claim 1, wherein human PSGL-1 comprises the amino acid sequence of SEQ ID NO:11 or SEQ ID NO:22.

17. The method of claim 1, wherein the subject is a human.

18. The method of claim 1, wherein the antibody is administered by intravenous infusion.

19. The method of claim 1, wherein the antibody is a monoclonal antibody.

20. The method of claim 1, wherein the JAK inhibitor is administered to the subject before, after, or simultaneous with administration of the antibody.

21. The method of claim 1, wherein the JAK inhibitor is administered orally to the subject.

22. The method of claim 1, wherein, prior to administration of the antibody and the JAK inhibitor, the subject has been treated with a corticosteroid.

23. The method of claim 1, wherein administration of the antibody and the JAK inhibitor results in a reduction in one or more symptoms of the T-cell mediated inflammatory disease in the subject.

* * * * *

```
                          SEQUENCE LISTING

Sequence total quantity: 39
SEQ ID NO: 1           moltype = AA  length = 219
FEATURE                Location/Qualifiers
source                 1..219
                       mol_type = protein
                       organism = synthetic construct
SEQUENCE: 1
DIQMTQSPSS LSASVGDRVT ITCRSSQSIV HNDGNTYFEW YQQKPGKAPK LLIYKVSNRF   60
SGVPSRFSGS GSGTHFTLTI SSLQPEDFAT YYCFQGSYVP LTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 2           moltype = AA  length = 446
FEATURE                Location/Qualifiers
source                 1..446
                       mol_type = protein
                       organism = synthetic construct
SEQUENCE: 2
EVQLVESGGG LVQPGGSLRL SCAASGFTFS SFGMHWVRQA PGKGLEWVAY INGGSSTIFY   60
ANAVKGRFTI SRDNAKNTLY LQMNSLRAED TAVYYCARYA SYGGGAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 3           moltype = AA  length = 112
FEATURE                Location/Qualifiers
source                 1..112
                       mol_type = protein
                       organism = synthetic construct
SEQUENCE: 3
```

```
DIQMTQSPSS LSASVGDRVT ITCRSSQSIV HNDGNTYFEW YQQKPGKAPK LLIYKVSNRF    60
SGVPSRFSGS GSGTHFTLTI SSLQPEDFAT YYCFQGSYVP LTFGQGTKVE IK           112

SEQ ID NO: 4           moltype = AA   length = 120
FEATURE                Location/Qualifiers
source                 1..120
                       mol_type = protein
                       organism = synthetic construct
SEQUENCE: 4
EVQLVESGGG LVQPGGSLRL SCAASGFTFS SFGMHWVRQA PGKGLEWVAY INGGSSTIFY    60
ANAVKGRFTI SRDNAKNTLY LQMNSLRAED TAVYYCARYA SYGGGAMDYW GQGTLVTVSS   120

SEQ ID NO: 5           moltype = AA   length = 16
FEATURE                Location/Qualifiers
source                 1..16
                       mol_type = protein
                       organism = synthetic construct
SEQUENCE: 5
RSSQSIVHND GNTYFE                                                    16

SEQ ID NO: 6           moltype = AA   length = 7
FEATURE                Location/Qualifiers
source                 1..7
                       mol_type = protein
                       organism = synthetic construct
SEQUENCE: 6
KVSNRFS                                                               7

SEQ ID NO: 7           moltype = AA   length = 9
FEATURE                Location/Qualifiers
source                 1..9
                       mol_type = protein
                       organism = synthetic construct
SEQUENCE: 7
FQGSYVPLT                                                             9

SEQ ID NO: 8           moltype = AA   length = 5
FEATURE                Location/Qualifiers
source                 1..5
                       mol_type = protein
                       organism = synthetic construct
SEQUENCE: 8
SFGMH                                                                 5

SEQ ID NO: 9           moltype = AA   length = 17
FEATURE                Location/Qualifiers
source                 1..17
                       mol_type = protein
                       organism = synthetic construct
SEQUENCE: 9
YINGGSSTIF YANAVKG                                                   17

SEQ ID NO: 10          moltype = AA   length = 11
FEATURE                Location/Qualifiers
source                 1..11
                       mol_type = protein
                       organism = synthetic construct
SEQUENCE: 10
YASYGGGAMD Y                                                         11

SEQ ID NO: 11          moltype = AA   length = 412
FEATURE                Location/Qualifiers
source                 1..412
                       mol_type = protein
                       organism = Homo sapiens
SEQUENCE: 11
MPLQLLLLLI LLGPGNSLQL WDTWADEAEK ALGPLLARDR RQATEYEYLD YDFLPETEPP    60
EMLRNSTDTT PLTGPGTPES TTVEPAARRS TGLDAGGAVT ELTTELANMG NLSTDSAAME   120
IQTTQPAATE AQTTQPVPTE AQTTPLAATE AQTTRLTATE AQTTPLAATE AQTTPPAATE   180
AQTTQPTGLE AQTTAPAAME AQTTAPAAME AQTTPPAAME AQTTQTTAME AQTTAPEATE   240
AQTTQPTATE AQTTPLAAME ALSTEPSATE ALSMEPTTKR GLFIPFSVSS VTHKGIPMAA   300
SNLSVNYPVG APDHISVKQC LLAILILALV ATIFFVCTVV LAVRLSRKGH MYPVRNYSPT   360
EMVCISSLLP DGGEGPSATA NGGLSKAKSP GLTPEPREDR EGDDLTLHSF LP           412

SEQ ID NO: 12          moltype = AA   length = 13
FEATURE                Location/Qualifiers
source                 1..13
                       mol_type = protein
                       organism = synthetic construct
```

```
SEQUENCE: 12
ESKYGPPCPP CPA                                                               13

SEQ ID NO: 13           moltype = AA  length = 23
FEATURE                 Location/Qualifiers
source                  1..23
                        mol_type = protein
                        organism = synthetic construct
SEQUENCE: 13
DIQMTQSPSS LSASVGDRVT ITC                                                    23

SEQ ID NO: 14           moltype = AA  length = 15
FEATURE                 Location/Qualifiers
source                  1..15
                        mol_type = protein
                        organism = synthetic construct
SEQUENCE: 14
WYQQKPGKAP KLLIY                                                             15

SEQ ID NO: 15           moltype = AA  length = 32
FEATURE                 Location/Qualifiers
source                  1..32
                        mol_type = protein
                        organism = synthetic construct
SEQUENCE: 15
GVPSRFSGSG SGTHFTLTIS SLQPEDFATY YC                                          32

SEQ ID NO: 16           moltype = AA  length = 10
FEATURE                 Location/Qualifiers
source                  1..10
                        mol_type = protein
                        organism = synthetic construct
SEQUENCE: 16
FGQGTKVEIK                                                                   10

SEQ ID NO: 17           moltype = AA  length = 30
FEATURE                 Location/Qualifiers
source                  1..30
                        mol_type = protein
                        organism = synthetic construct
SEQUENCE: 17
EVQLVESGGG LVQPGGSLRL SCAASGFTFS                                             30

SEQ ID NO: 18           moltype = AA  length = 14
FEATURE                 Location/Qualifiers
source                  1..14
                        mol_type = protein
                        organism = synthetic construct
SEQUENCE: 18
WVRQAPGKGL EWVA                                                              14

SEQ ID NO: 19           moltype = AA  length = 32
FEATURE                 Location/Qualifiers
source                  1..32
                        mol_type = protein
                        organism = synthetic construct
SEQUENCE: 19
RFTISRDNAK NTLYLQMNSL RAEDTAVYYC AR                                          32

SEQ ID NO: 20           moltype = AA  length = 11
FEATURE                 Location/Qualifiers
source                  1..11
                        mol_type = protein
                        organism = synthetic construct
SEQUENCE: 20
WGQGTLVTVS S                                                                 11

SEQ ID NO: 21           moltype = AA  length = 13
FEATURE                 Location/Qualifiers
source                  1..13
                        mol_type = protein
                        organism = synthetic construct
SEQUENCE: 21
ESKYGPPCPS CPA                                                               13

SEQ ID NO: 22           moltype = AA  length = 402
FEATURE                 Location/Qualifiers
source                  1..402
                        mol_type = protein
```

```
                        organism = Homo sapiens
SEQUENCE: 22
MPLQLLLLLI  LLGPGNSLQL  WDTWADEAEK  ALGPLLARDR  RQATEYEYLD  YDFLPETEPP    60
EMLRNSTDTT  PLTGPGTPES  TTVEPAARRS  TGLDAGGAVT  ELTTELANMG  NLSTDSAAME   120
IQTTQPAATE  AQTTPLAATE  AQTTRLTATE  AQTTPPAATE  AQTTPLAATE  AQTTQPTGLE   180
AQTTAPAAME  AQTTAPAAME  AQTTPAAME   AQTTQTTAME  AQTTAPEATE  AQTTQPTATE   240
AQTTPLAAME  ALSTEPSATE  ALSMEPTTKR  GLFIPFSVSS  VTHKGIPMAA  SNLSVNYPVG   300
APDHISVKQC  LLAILILALV  ATIFFVCTVV  LAVRLSRKGH  MYPVRNYSPT  EMVCISSLLP   360
DGGEGPSATA  NGGLSKAKSP  GLTPEPREDR  EGDDLTLHSF  LP                      402

SEQ ID NO: 23           moltype = AA  length = 745
FEATURE                 Location/Qualifiers
source                  1..745
                        mol_type = protein
                        organism = synthetic construct
SEQUENCE: 23
DIQMTQSPSS  LSASVGDRVT  ITCRSSQSIV  HNDGNTYFEW  YQQKPGKAPK  LLIYKVSNRF    60
SGVPSRFSGS  GSGTHFTLTI  SSLQPEDFAT  YYCFQGSYVP  LTFGQGTKVE  IKGGGGSGGG   120
GSEVQLVESG  GGLVQPGGSL  RLSCAASGFT  FSSFGMHWVR  QAPGKGLEWV  AYINGGSSTI   180
FYANAVKGRF  TISRDNAKNT  LYLQMNSLRA  EDTAVYYCAR  YASYGGGAMD  YWGQGTLVTV   240
SSGGGGSGGG  GSGGGGSGGG  GSGGGGSDIQ  MTQSPSSLSA  SVGDRVTITC  RSSQSIVHND   300
GNTYFEWYQQ  KPGKAPKLLI  YKVSNRFSGV  PSRFSGSGSG  THFTLTISSL  QPEDFATYYC   360
FQGSYVPLTF  GQGTKVEIKG  GGGSGGGGSE  VQLVESGGGL  VQPGGSLRLS  CAASGFTFSS   420
FGMHWVRQAP  GKGLEWVAYI  NGGSSTIFYA  NAVKGRFTIS  RDNAKNTLYL  QMNSLRAEDT   480
AVYYCARYAS  YGGGAMDYWG  QGTLVTVSSG  GGGSAAAESK  YGPPCPPCPA  PEFLGGPSVF   540
LFPPKPKDTL  MISRTPEVTC  VVVDVSQEDP  EVQFNWYVDG  VEVHNAKTKP  REEQFNSTYR   600
VVSVLTVLHQ  DWLNGKEYKC  KVSNKGLPSS  IEKTISKAKG  QPREPQVYTL  PPSQEEMTKN   660
QVSLTCLVKG  FYPSDIAVEW  ESNGQPENNY  KTTPPVLDSD  GSFFLYSRLT  VDKSRWQEGN   720
VFSCSVMHEA  LHNHYTQKSL  SLSLG                                           745

SEQ ID NO: 24           moltype = AA  length = 5
FEATURE                 Location/Qualifiers
source                  1..5
                        mol_type = protein
                        organism = synthetic construct
SEQUENCE: 24
AYYIH                                                                     5

SEQ ID NO: 25           moltype = AA  length = 17
FEATURE                 Location/Qualifiers
source                  1..17
                        mol_type = protein
                        organism = synthetic construct
SEQUENCE: 25
RVNPNTGGTS  YNPKFKG                                                      17

SEQ ID NO: 26           moltype = AA  length = 10
FEATURE                 Location/Qualifiers
source                  1..10
                        mol_type = protein
                        organism = synthetic construct
SEQUENCE: 26
SGSPYYRYDD                                                               10

SEQ ID NO: 27           moltype = AA  length = 445
FEATURE                 Location/Qualifiers
source                  1..445
                        mol_type = protein
                        organism = synthetic construct
SEQUENCE: 27
EVQLQQSGPD  LVKPGALVKI  SCKASGYSFT  AYYIHWVKQS  HGKSLEWIGR  VNPNTGGTSY    60
NPKFKGKAIL  NVDKSSSTAY  MELRSLTSED  SAVYYCARSG  SPYYRYDDWG  QGTTLTVSSA   120
STKGPSVFPL  APCSRSTSES  TAALGCLVKD  YFPEPVTVSW  NSGALTSGVH  TFPAVLQSSG   180
LYSLSSVVTV  PSSSLGTKTY  TCNVDHKPSN  TKVDKRVESK  YGPPCPPCPA  PEFLGGPSVF   240
LFPPKPKDTL  MISRTPEVTC  VVVDVSQEDP  EVQFNWYVDG  VEVHNAKTKP  REEQFNSTYR   300
VVSVLTVLHQ  DWLNGKEYKC  KVSNKGLPSS  IEKTISKAKG  QPREPQVYTL  PPSQEEMTKN   360
QVSLTCLVKG  FYPSDIAVEW  ESNGQPENNY  KTTPPVLDSD  GSFFLYSRLT  VDKSRWQEGN   420
VFSCSVMHEA  LHNHYTQKSL  SLSLG                                           445

SEQ ID NO: 28           moltype = AA  length = 12
FEATURE                 Location/Qualifiers
source                  1..12
                        mol_type = protein
                        organism = synthetic construct
SEQUENCE: 28
RASSTVNSTY  LH                                                           12

SEQ ID NO: 29           moltype = AA  length = 7
FEATURE                 Location/Qualifiers
```

```
source                  1..7
                        mol_type = protein
                        organism = synthetic construct
SEQUENCE: 29
GSSNLAS                                                                    7

SEQ ID NO: 30           moltype = AA   length = 9
FEATURE                 Location/Qualifiers
source                  1..9
                        mol_type = protein
                        organism = synthetic construct
SEQUENCE: 30
QQYSGYPLT                                                                  9

SEQ ID NO: 31           moltype = AA   length = 215
FEATURE                 Location/Qualifiers
source                  1..215
                        mol_type = protein
                        organism = synthetic construct
SEQUENCE: 31
ENVLTQSPAI MSASPGEKVT MTCRASSTVN STYLHWFQQK SGASPKLWIY GSSNLASGVP          60
ARFSGSGSGT SYSLTISSVE AEDAATYYCQ QYSGYPLTFG AGTTLELKRT VAAPSVFIFP         120
PSDEQLKSGT ASVVCLLNNF YPREAKVQWK VDNALQSGNS QESVTEQDSK DSTYSLSSTL         180
TLSKADYEKH KVYACEVTHQ GLSSPVTKSF NRGEC                                    215

SEQ ID NO: 32           moltype = AA   length = 5
FEATURE                 Location/Qualifiers
source                  1..5
                        mol_type = protein
                        organism = synthetic construct
SEQUENCE: 32
TNAMN                                                                      5

SEQ ID NO: 33           moltype = AA   length = 19
FEATURE                 Location/Qualifiers
source                  1..19
                        mol_type = protein
                        organism = synthetic construct
SEQUENCE: 33
RIRSKSNNYA TYYADSVKD                                                      19

SEQ ID NO: 34           moltype = AA   length = 9
FEATURE                 Location/Qualifiers
source                  1..9
                        mol_type = protein
                        organism = synthetic construct
SEQUENCE: 34
GGSYWYFDV                                                                  9

SEQ ID NO: 35           moltype = AA   length = 446
FEATURE                 Location/Qualifiers
source                  1..446
                        mol_type = protein
                        organism = synthetic construct
SEQUENCE: 35
EVQLVESGGG LVQPGGSLKL SCAASGFTFN TNAMNWVRQA PGKGLEWVAR IRSKSNNYAT          60
YYADSVKDRF TISRDDSKSI IYLQMNSLKT EDTGIYYCVR GGSYWYFDVW GTGTTVTVSS         120
ASTKGPSVFP LAPCSRSTSE STAALGCLVK DYFPEPVTVS WNSGALTSGV HTFPAVLQSS         180
GLYSLSSVVT VPSSSLGTKT YTCNVDHKPS NTKVDKRVES KYGPPCPPCP APPVAGGPSV         240
FLFPPKPKDT LMISRTPEVT CVVVDVSQED PEVQFNWYVD GVEVHNAKTK PREEQFNSTY         300
RVVSVLTVLH QDWLNGKEYK CKVSNKGLPS SIEKTISKAK GQPREPQVYT LPPSQEEMTK         360
NQVSLTCLVK GFYPSDIAVE WESNGQPENN YKTTPPVLDS DGSFFLYSRL TVDKSRWQEG         420
NVFSCSVMHE ALHNHYTQKS LSLSLG                                             446

SEQ ID NO: 36           moltype = AA   length = 16
FEATURE                 Location/Qualifiers
source                  1..16
                        mol_type = protein
                        organism = synthetic construct
SEQUENCE: 36
RSSQSIVNSN GNTYLE                                                         16

SEQ ID NO: 37           moltype = AA   length = 7
FEATURE                 Location/Qualifiers
source                  1..7
                        mol_type = protein
                        organism = synthetic construct
SEQUENCE: 37
KVSNRFS                                                                    7
```

```
SEQ ID NO: 38          moltype = AA  length = 9
FEATURE                Location/Qualifiers
source                 1..9
                       mol_type = protein
                       organism = synthetic construct
SEQUENCE: 38
FQGSHVPWT                                                                      9

SEQ ID NO: 39          moltype = AA  length = 219
FEATURE                Location/Qualifiers
source                 1..219
                       mol_type = protein
                       organism = synthetic construct
SEQUENCE: 39
DVIMTQSPLS LPVSLGQPAS ISCRSSQSIV NSNGNTYLEW YLQKPGQSPR LLIYKVSNRF   60
SGVPDRFSGS GSGTDFTLKI SRVEAEDVGV YYCFQGSHVP WTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```